US012624376B2

(12) United States Patent     (10) Patent No.:   US 12,624,376 B2

Muzzi-Erichsen     (45) Date of Patent:     May 12, 2026

(54) MUTANTS OF A FILAMENTOUS FUNGAL CELL HAVING INCREASED PRODUCTIVITY IN THE PRODUCTION OF A POLYPEPTIDE

(71) Applicant: Novozymes A/S, Bagsvaerd (DK)

(72) Inventor: Gloria Muzzi-Erichsen, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 14 days.

(21) Appl. No.: 17/794,408

(22) PCT Filed: Jan. 12, 2021

(86) PCT No.: PCT/EP2021/050464

§ 371 (c)(1),
(2) Date: Jul. 21, 2022

(87) PCT Pub. No.: WO2021/148278

PCT Pub. Date: Jul. 29, 2021

(65) Prior Publication Data

US 2023/0242960 A1     Aug. 3, 2023

Related U.S. Application Data

(60) Provisional application No. 62/965,752, filed on Jan. 24, 2020.

(51) Int. Cl.
| | |
|---|---|
| *C12P 21/02* | (2006.01) |
| *C12N 1/14* | (2006.01) |
| *C12N 9/14* | (2006.01) |
| *C12N 15/80* | (2006.01) |
| *C12R 1/885* | (2006.01) |

(52) U.S. Cl.
CPC .............. *C12P 21/02* (2013.01); *C12N 1/14* (2013.01); *C12N 9/14* (2013.01); *C12N 15/80* (2013.01); *C12R 2001/885* (2021.05); *C12Y 306/05* (2013.01)

(58) Field of Classification Search
CPC ..................................................... C12N 15/80
See application file for complete search history.

(56) References Cited

PUBLICATIONS

Arnau et al, 2020, Springer International Publishing, Chapter 7, 179-210.
Fiedler et al, 2018, Micro Cell Fac 17(1), 95.
Fitz et al, 2019, Fungal Biology and Biotechnology 6(1), 16.
He et al, 2016, Biotech 6(214), 1-10.
Virag et al, 2007, Mol Microbiol 66(6), 1579-1596.
Zhang et al, 2012, PLOS ONE 7(11), e48786.
Guan, China PHD Thesis Full Text Database, Agricultural Science and Technology Series, 2017, 1-86, Incl EnAb.
Martinez et al., NCBI Reference Sequence XM_006963997.1, 2014.
Zhang et al., GenBank AFQ23948.1, 2012.
Zhang et al., GenBank JX114948.1, 2012.

*Primary Examiner* — Suzanne M Noakes
(74) *Attorney, Agent, or Firm* — Eric J. Fechter

(57) ABSTRACT

The present invention relates to a mutant of a parent filamentous fungal cell, comprising: a polynucleotide encoding a polypeptide of interest; a racA gene encoding a Rho-GTPase RacA protein, wherein the racA gene is modified rendering the mutant partially or completely deficient in the production of the Rho-GTPase RacA protein; and a ras2 gene encoding a GTPase Ras2 protein, wherein the GTPase Ras2 protein is modified to produce a GTPase Ras2 variant comprising a substitution at a position corresponding to position 16 of SEQ ID NO: 11, wherein the combination of the modified racA gene and the Ras2 variant synergistically increases the productivity of the mutant in the production of the polypeptide of interest. The present invention also relates to a method of producing a polypeptide of interest with such a mutant.

18 Claims, 6 Drawing Sheets

Specification includes a Sequence Listing.

MUTANTS OF A FILAMENTOUS FUNGAL CELL HAVING INCREASED PRODUCTIVITY IN THE PRODUCTION OF A POLYPEPTIDE

CROSS-REFERENCE TO RELATED APPLICATIONS

This application is a 35 U.S.C. 371 national application of PCT/EP2021/050464, filed Jan. 12, 2021, which claims priority or the benefit from U.S. Provisional Application Ser. No. 62/965,752, filed Jan. 24, 2020. The contents of these applications are fully incorporated herein by reference.

REFERENCE TO A SEQUENCE LISTING

This application contains a Sequence Listing that was submitted as an txt file named 15108-US-PCT Corrected SQ ST25.txt (created on May 15, 2025, containing 78,280 bytes), which is incorporated herein by reference.

BACKGROUND OF THE INVENTION

Field of the Invention

The present invention relates to mutant filamentous fungal cells with increased productivity in the production of polypeptides.

Description of the Related Art

Filamentous fungi are widely used for producing enzymes and other biologicals for a variety of industrial applications. The productivity of a filamentous fungal cell in the production of a polypeptide of interest is dependent upon several factors, such as carbon source, nitrogen source, secretion, pH, temperature, and dissolved oxygen. In particular, the carbon source can determine which genes for secreted enzymes are induced and/or repressed and their production rates. The carbon source acts through transcription factors and their associated promoters that are either activated or repressed depending on the level of the carbon source.

It is reported that the racA gene plays a key role in hyphal growth and hyphal branching in filamentous fungi and that racA gene inactivation contributes to increase protein production because of enhanced secretion potential (Chen et al., 2016, *Biotech* 6: 214; Fitz et al., 2019, Fungal Biol. Biotechnology (2019), 6: 16; Fielder et al., 2018, *Microb. Cell.* 17: 95; Virag, 2007, *Molecular Microbiology* 66: 1579-1596).

It is also reported that the Ras GTPase ras2 gene is important for regulating morphogenesis and cellulase expression in *Trichoderma reesei* where the ras2G16V constitutively active variant increases cellulase gene transcription in *T. reesei* under inducing conditions, especially cellulase genes under control of the Xyr1, Ace2, Cre1 and Ace1 transcription factors (Zhang et al., 2012, *PLOS One* 7: e48786).

The present invention provides mutants of a filamentous fungal cell for increasing the productivity of the filamentous fungal cell in the production of a polypeptide of interest where the combination of a modified racA gene and a Ras2 variant synergistically increases the productivity of the mutant.

SUMMARY OF THE INVENTION

The present invention relates to an isolated mutant of a parent filamentous fungal cell, comprising:

(a) a polynucleotide encoding a polypeptide of interest;

(b) a racA gene encoding a Rho-GTPase RacA protein, wherein the racA gene is modified in the parent filamentous fungal cell to produce the mutant rendering the mutant partially or completely deficient in the production of the Rho-GTPase RacA protein; and (c) a ras2 gene encoding a GTPase Ras2 protein, wherein the GTPase Ras2 protein is modified in the parent filamentous fungal cell to produce a GTPase Ras2 variant comprising a substitution at a position corresponding to position 16 of SEQ ID NO: 11;

wherein the combination of the modified racA gene and the GTPase Ras2 variant synergistically increases the productivity of the mutant in the production of the polypeptide of interest.

The present invention also relates to a method of producing a polypeptide of interest, comprising cultivating such a mutant filamentous fungal cell in a medium for production of the polypeptide of interest, and optionally recovering the polypeptide of interest.

DEFINITIONS

Figure 1:
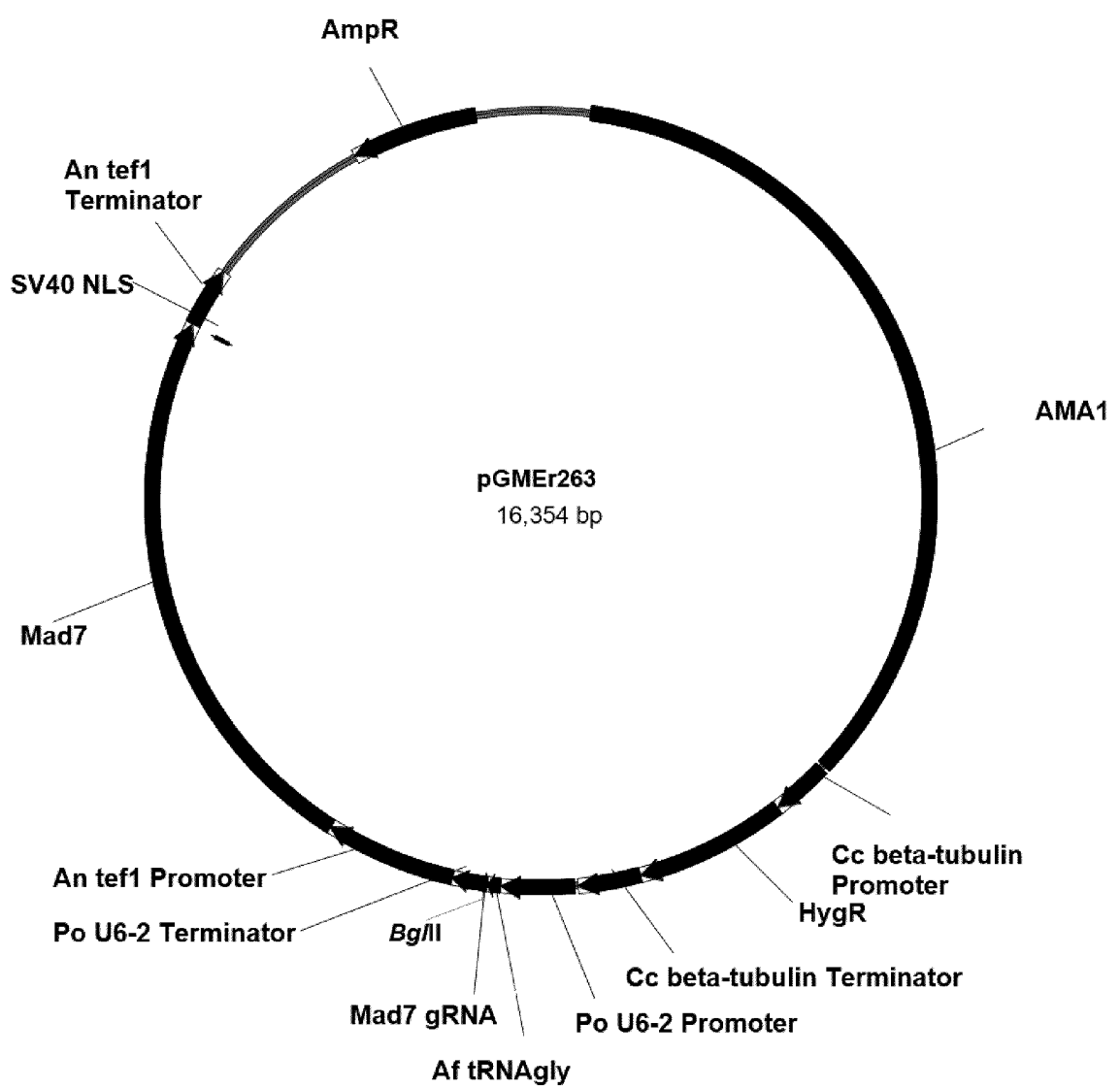
FIG. 1 shows a map of plasmid pGMEr263.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans.

Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd.) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc.).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" or "AA9 lytic polysaccharide monooxygenase" means a polypeptide classified as a lytic polysaccharide monooxygenase (Quinlan et al., 2011, *Proc. Natl. Acad. Sci. USA* 108: 15079-15084; Phillips et al., 2011, *ACS Chem. Biol.* 6: 1399-1406; Li et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., and a suitable pH, such as 4-9, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsvaerd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM MnSO$_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can be used in the presence of a soluble activating divalent metal cation according to WO 2008/151043 or WO 2012/122518, e.g., manganese or copper.

The AA9 polypeptide can also be used in the presence of a dioxy compound, a bicyclic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1—>4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that can be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279;

van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, carboxymethylcellulose, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature, such as 40° C.-80° C., and a suitable pH, such as 4-9, compared to a control hydrolysis without addition of cellulolytic enzyme protein. Typical conditions are 1 ml reactions, washed or unwashed PCS, 5% insoluble solids (dry weight), 50 mM sodium acetate pH 5, 0.1 mM $CuCl_2$, 50° C., 55° C., or 60° C., 72 hours, sugar analysis by AMINEX® HPX-87H column chromatography (Bio-Rad Laboratories, Inc., Hercules, CA, USA).

Coding sequence: The term "coding sequence" means a polynucleotide, which directly specifies the amino acid sequence of a polypeptide. The boundaries of the coding sequence are generally determined by an open reading frame, which begins with a start codon, such as ATG, GTG, or TTG, and ends with a stop codon, such as TAA, TAG, or TGA. The coding sequence can be a genomic DNA, cDNA, synthetic DNA, or a combination thereof.

Control sequences: The term "control sequences" means nucleic acid sequences necessary for expression of a coding sequence for a polypeptide. Each control sequence can be native (i.e., from the same gene) or heterologous (i.e., from a different gene) to the polynucleotide encoding the polypeptide or native or heterologous to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences can be provided with linkers for the purpose of introducing specific restriction sites facilitating ligation of the control sequences with the coding region of the polynucleotide encoding a polypeptide.

Deficient: The term "deficient" means the racA gene encoding a Rho-GTPase RacA protein of the present invention is modified in a parent filamentous fungal cell to produce a mutant rendering the mutant partially deficient (at least 25% less, more preferably at least 50% less, even more preferably at least 75% less, and most preferably at least 95% less Rho-GTPase RacA protein) or completely deficient (100% less Rho-GTPase RacA protein) in the production of the Rho-GTPase RacA protein compared to the parent filamentous fungal cell without the modification of the racA gene when cultivated under identical conditions. The level of a Rho-GTPase RacA protein produced by a filamentous fungal cell, parent or mutant, can be determined using methods described herein or known in the art.

Endoglucanase: The term "endoglucanase" means a 4-(1, 3; 1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Hemicellulolytic enzyme or hemicellulase: The term "hemicellulolytic enzyme" or "hemicellulase" means one or more enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetyl-mannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, such as 40° C.–80° C., and a suitable pH, such as 4-9.

Host cell: The term "host cell" means a mutant filamentous fungal cell comprising a modified racA gene and expressing a GTPase Rac2 variant that is susceptible to transformation, transfection, transduction, or the like with a nucleic acid construct or expression vector comprising a polynucleotide encoding a polypeptide of interest. The term "host cell" encompasses any progeny of a cell that is not identical to the cell due to mutations that occur during replication.

Increased productivity: The term "increased productivity" and variations thereof mean an increase of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, or at least 50% in the production of the amount of a polypeptide of interest by a mutant filamentous fungal cell of the present invention comprising a modified racA gene and expressing a GTPase Rac2 variant when cultivated under the same conditions of medium composition, temperature, pH, cell density, dissolved oxygen, and time as the parent filamentous fungal cell without the modified racA gene and GTPase Ras2 variant. In one aspect, the productivity of the mutant filamentous fungal cell is increased 1%, 2%, 3%, 4%, 5% 6%, 7%, 8%, 9%, 10%, 11%, 12%, 13%, 14%, 15%, 16%, 17%, 18%, 19%, 20%, 25%, 30%, 35%, 40%, 45%, or 50% in the production of the amount of the polypeptide of interest compared to the parent filamentous fungal cell.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, or peptide, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Rho-GTPase RacA protein: The term "Rho-GTPase RacA protein" means a member of the Rho-GTPase family. Rho-GTPases are signaling G proteins (guanine nucleotide-binding proteins) and function as molecular switches. Rho-GTPases are found in all eukaryotic kingdoms and have been shown to regulate intracellular actin dynamics playing a role in organelle development, cytoskeletal dynamics, cell movement, and other cellular functions.

Ras2 Protein: The term "Ras2 protein" means a member of the Ras-GTPase family. Ras-GTPases are signaling G proteins (guanine nucleotide-binding proteins) and function as molecular switches. Ras-GTPases play an important role in various signal pathways controlling cell proliferation, morphogenesis, vesicular trafficking, and gene expression. In *Trichoderma reesei* the Ras2 protein modulates cellulase gene expression under cellulase inducing conditions.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$\text{(Identical Residues} \times 100)/(\text{Length of Alignment–Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

$$\text{(Identical Deoxyribonucleotides} \times 100)/(\text{Length of Alignment–Total Number of Gaps in Alignment})$$

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Variant: The term "variant" means a GTPase Ras2 protein comprising a substitution at a position corresponding to position 16 of SEQ ID NO: 11. A substitution means replacement of the amino acid occupying a position with a different amino acid. The variants of the present invention are constitutively active under cellulase inducing conditions.

Wild-type: The term "wild-type" in reference to an amino acid sequence or nucleic acid sequence means that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects. Unless defined otherwise or clearly indicated by context, all technical and scientific terms used herein have the same meaning as commonly understood by one of ordinary skill in the art to which this invention belongs.

Conventions for Designation of Variants

For purposes of the present invention, the GTPase Ras2 protein disclosed in SEQ ID NO: 11 is used as a reference to determine the corresponding amino acid position in another GTPase Ras2 protein. The amino acid sequence of another GTPase Ras2 protein is aligned with the GTPase Ras2 protein disclosed in SEQ ID NO: 11, and based on the alignment, the amino acid position number corresponding to any amino acid residue in the polypeptide disclosed in SEQ ID NO: 11 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

In describing the GTPase Ras2 protein variants of the present invention, the nomenclature described below is adapted for ease of reference. The accepted IUPAC single letter or three letter amino acid abbreviation is employed.

For an amino acid substitution, the following nomenclature is used: Original amino acid, position, substituted amino acid. Accordingly, the substitution of glycine at position 16 with valine is designated as "Gly16Val" or "G16V".

DETAILED DESCRIPTION OF THE INVENTION

The present invention relates to an isolated mutant of a parent filamentous fungal cell, comprising:

(a) a polynucleotide encoding a polypeptide of interest;

(b) a racA gene encoding a Rho-GTPase RacA protein, wherein the racA gene is modified in the parent filamentous fungal cell to produce the mutant rendering the mutant partially or completely deficient in the production of the Rho-GTPase RacA protein; and (c) a ras2 gene encoding a GTPase Ras2 protein, wherein the GTPase Ras2 protein is modified in the parent filamentous fungal cell to produce a GTPase Ras2 variant comprising a substitution at a position corresponding to position 16 of SEQ ID NO: 11;

wherein the combination of the modified racA gene and the GTPase Ras2 variant synergistically increases the productivity of the mutant in the production of the polypeptide of interest.

An advantage of the present invention is that the combination of the modified racA gene and the GTPase Ras2 variant synergistically increases the productivity of the mutant in the production of the polypeptide of interest. In one embodiment, the combination of the modified racA gene and the GTPase Ras2 variant results in a more branched mycelial phenotype for the mutant filamentous fungal cell compared to the parent cell. In another embodiment, the combination of the modified racA gene and the GTPase Ras2 variant increases secretion of the polypeptide of interest in the mutant filamentous fungal cell compared to the parent cell. In another embodiment, the combination of the modified racA gene and the GTPase Ras2 variant increases the amount of total protein produced by for the mutant filamentous fungal cell in a fermentation compared to the parent cell. In another embodiment, the combination of the modified racA gene and the GTPase Ras2 variant increases the amount of cellulase produced by the mutant filamentous fungal cell compared to the parent cell. In a preferred embodiment, the combination of the modified racA gene and the GTPase Ras2 variant increases the amount of beta-glucosidase produced by the mutant filamentous fungal cell compared to the parent cell.

In another embodiment, the combination of the modified racA gene and the GTPase Ras2 variant reduces the viscosity of the mutant filamentous fungal cell in a fermentation compared to the parent cell. In another embodiment, the combination of the modified racA gene and the GTPase Ras2 variant increases the total amount of feed that can be fed to the mutant filamentous fungal cell during a fermentation compared to the parent cell.

Rho-GTPase RacA Proteins

In the present invention the GTPase RacA protein can be any GTPase RacA protein.

In one aspect, the GTPase RacA protein is selected from the group consisting of:

(i) a Rho-GTPase RacA protein comprising an amino acid sequence having at least 70% sequence identity to SEQ ID NO: 2, (ii) a Rho-GTPase RacA protein encoded by a polynucleotide comprising a nucleotide sequence having at least 70% sequence identity to SEQ ID NO: 1, and (iii) a Rho-GTPase RacA protein encoded by a polynucleotide comprising a nucleotide sequence that hybridizes under high stringency conditions with the full-length complement of SEQ ID NO: 1.

In another aspect, the Rho-GTPase RacA protein has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the amino acid sequence of SEQ ID NO: 2.

In one embodiment the Rho-GTPase RacA protein comprises an amino acid sequence having at least 80% sequence identity to SEQ ID NO: 2.

In one embodiment the Rho-GTPase RacA protein comprises an amino acid sequence having at least 85% sequence identity to SEQ ID NO: 2.

In one embodiment the Rho-GTPase RacA protein comprises an amino acid sequence having at least 90% sequence identity to SEQ ID NO: 2 In one embodiment the Rho-GTPase RacA protein comprises an amino acid sequence having at least 95% sequence identity to SEQ ID NO: 2.

In one embodiment the Rho-GTPase RacA protein comprises or consists of SEQ ID NO: 2.

In one embodiment, the Rho-GTPase RacA protein differs by up to 10 amino acids, e.g., 1, 2, 3, 4, 5, 6, 7, 8, 9, or 10, from the amino acid sequence of SEQ ID NO: 2.

In another embodiment, the Rho-GTPase RacA protein comprises the amino acid sequence of SEQ ID NO: 2 or an allelic variant thereof. In another embodiment, the Rho-GTPase RacA protein comprises the amino acid sequence of SEQ ID NO: 2. In another embodiment, the Rho-GTPase RacA protein consists of the amino acid sequence of SEQ ID NO: 2.

In another aspect, the Rho-GTPase RacA protein is encoded by a polynucleotide comprising a nucleotide sequence having a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO: 1, or the cDNA sequence thereof.

In one embodiment, the Rho-GTPase RacA protein is encoded by a polynucleotide comprising the nucleotide sequence of SEQ ID NO: 1. In another embodiment, the Rho-GTPase RacA protein is encoded by a polynucleotide consisting of the nucleotide sequence of SEQ ID NO: 1.

In one embodiment the Rho-GTPase RacA protein is encoded by a polynucleotide comprising a nucleotide sequence having at least 80% sequence identity to SEQ ID NO: 1.

In one embodiment the Rho-GTPase RacA protein is encoded by a polynucleotide comprising a nucleotide sequence having at least 85% sequence identity to SEQ ID NO: 1.

In one embodiment the Rho-GTPase RacA protein is encoded by a polynucleotide comprising a nucleotide sequence having at least 90% sequence identity to SEQ ID NO: 1.

In one embodiment the Rho-GTPase RacA protein is encoded by a polynucleotide comprising a nucleotide sequence having at least 95% sequence identity to SEQ ID NO: 1.

In one embodiment the Rho-GTPase RacA protein is encoded by a polynucleotide comprising or consisting of SEQ ID NO: 1.

In one embodiment the Rho-GTPase RacA protein is encoded by a polynucleotide that hybridizes under very high stringency conditions with the full-length complement of SEQ ID NO: 1.

In another aspect, the Rho-GTPase RacA protein is encoded by a polynucleotide comprising a nucleotide sequence that hybridizes under very low stringency conditions, low stringency conditions, medium stringency conditions, medium-high stringency conditions, high stringency conditions, or very high stringency conditions with (i) SEQ ID NO: 1, (ii) the cDNA sequence thereof, or (iii) the full-length complement of (i) or (ii) (Sambrook et al., 1989, *Molecular Cloning, A Laboratory Manual,* 2d edition, Cold Spring Harbor, New York).

The polynucleotide comprising the nucleotide sequence of SEQ ID NO: 1, or a subsequence thereof, as well as the polypeptide comprising the amino acid sequence of SEQ ID NO: 2, or a fragment thereof, can be used to design nucleic acid probes to identify and clone DNA encoding Rho-GTPase RacA proteins from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains can be screened for DNA that hybridizes with the probes described above and encodes a Rho-GTPase RacA protein. Genomic or other DNA from such other strains can be separated by agarose or polyacrylamide gel electrophoresis, or other separation techniques. DNA from the libraries or the separated DNA can be transferred to and immobilized on nitrocellulose or other suitable carrier material. In order to identify a clone or DNA that hybridizes with the nucleotide sequence of SEQ ID NO: 1, or a subsequence thereof, the carrier material is used in a Southern blot.

For purposes of the present invention, hybridization indicates that the polynucleotides hybridize to a labeled nucleic acid probe corresponding to (i) SEQ ID NO: 1; (ii) the cDNA sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is SEQ ID NO: 1 or the cDNA sequence thereof.

In another embodiment, the nucleic acid probe is a polynucleotide that encodes the Rho-GTPase RacA protein of SEQ ID NO: 2 or a fragment thereof.

GTPase Ras2 Proteins

In the present invention the GTPase Ras2 protein can be any GTPase Ras2 protein.

In one aspect, the GTPase Ras2 is selected from the group consisting of:

(i) a Rho-GTPase RacA protein comprising an amino acid sequence having at least 70% sequence identity to SEQ ID NO: 2,
   (ii) a Rho-GTPase RacA protein encoded by a polynucleotide comprising a nucleotide sequence having at least 70% sequence identity to SEQ ID NO: 1, and
   (iii) a Rho-GTPase RacA protein encoded by a polynucleotide comprising a nucleotide sequence that hybridizes under high stringency conditions with the full-length complement of SEQ ID NO: 1.

In another aspect, the GTPase Ras2 protein has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the amino acid sequence of SEQ ID NO: 11.

In one embodiment the GTPase Ras2 protein comprises an amino acid sequence having at least 80% sequence identity to SEQ ID NO: 11.

In one embodiment the GTPase Ras2 protein comprises an amino acid sequence having at least 85% sequence identity to SEQ ID NO: 11.

In one embodiment the GTPase Ras2 protein comprises an amino acid sequence having at least 90% sequence identity to SEQ ID NO: 11.

In one embodiment the GTPase Ras2 protein comprises an amino acid sequence having at least 95% sequence identity to SEQ ID NO: 11.

In one embodiment the GTPase Ras2 protein comprises or consists of SEQ ID NO: 11.

In one embodiment, the GTPase Ras2 protein differs by up to 10 amino acids, e.g., 1, 2, 3, 4, 5, 6, 7, 8, 9, or 10, from the amino acid sequence of SEQ ID NO: 11.

In another embodiment, the GTPase Ras2 protein comprises the amino acid sequence of SEQ ID NO: 11 or an allelic variant thereof. In another embodiment, the GTPase Ras2 protein comprises the amino acid sequence of SEQ ID NO: 11. In another embodiment, the GTPase Ras2 protein consists of the amino acid sequence of SEQ ID NO: 11.

In another aspect, the GTPase Ras2 protein is encoded by a polynucleotide comprising a nucleotide sequence having a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO: 10, or the cDNA sequence thereof.

In one embodiment the GTPase Ras2 protein is encoded by a polynucleotide comprising a nucleotide sequence having at least 80% sequence identity to SEQ ID NO: 10.

In one embodiment the GTPase Ras2 protein is encoded by a polynucleotide comprising a nucleotide sequence having at least 85% sequence identity to SEQ ID NO: 10.

In one embodiment the GTPase Ras2 protein is encoded by a polynucleotide comprising a nucleotide sequence having at least 90% sequence identity to SEQ ID NO: 10.

In one embodiment the GTPase Ras2 protein is encoded by a polynucleotide comprising a nucleotide sequence having at least 95% sequence identity to SEQ ID NO: 10.

In one embodiment the GTPase Ras2 protein is encoded by a polynucleotide comprising or consisting of SEQ ID NO: 10.

In one embodiment the GTPase Ras2 protein is encoded by a polynucleotide that hybridizes under very high stringency conditions with the full-length complement of SEQ ID NO: 10.

In one embodiment, the GTPase Ras2 protein is encoded by a polynucleotide comprising the nucleotide sequence of SEQ ID NO: 10. In another embodiment, the GTPase Ras2 protein is encoded by a polynucleotide consisting of the nucleotide sequence of SEQ ID NO: 10.

In another aspect, the GTPase Ras2 protein is encoded by a polynucleotide comprising a nucleotide sequence that hybridizes under very low stringency conditions, low stringency conditions, medium stringency conditions, medium-high stringency conditions, high stringency conditions, or very high stringency conditions with (i) SEQ ID NO: 10, (ii) the cDNA sequence thereof, or (iii) the full-length complement of (i) or (ii) (Sambrook et al., 1989, *Molecular Cloning, A Laboratory Manual,* 2d edition, Cold Spring Harbor, New York).

The polynucleotide comprising the nucleotide sequence of SEQ ID NO: 10, or a subsequence thereof, as well as the polypeptide comprising the amino acid sequence of SEQ ID NO: 11, or a fragment thereof, can be used to design nucleic acid probes to identify and clone DNA encoding GTPase Ras2 proteins from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains can be screened for DNA that hybridizes with the probes described above and encodes a GTPase Ras2 protein. Genomic or other DNA from such other strains can be separated by agarose or polyacrylamide gel electrophoresis, or other separation techniques. DNA from the libraries or the separated DNA can be transferred to and immobilized on nitrocellulose or other suitable carrier material. In order to identify a clone or DNA that hybridizes with the nucleotide sequence of SEQ ID NO: 10, or a subsequence thereof, the carrier material is used in a Southern blot.

For purposes of the present invention, hybridization indicates that the polynucleotides hybridize to a labeled nucleic acid probe corresponding to (i) SEQ ID NO: 10; (ii) the cDNA sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is SEQ ID NO: 10 or the cDNA sequence thereof.

In another embodiment, the nucleic acid probe is a polynucleotide that encodes the GTPase Ras2 protein of SEQ ID NO: 11 or a fragment thereof.

GTPase Ras2 Variants

In one aspect, the variant comprises or consists of a substitution at a position corresponding to position 16 of SEQ ID NO: 11. In another aspect, the amino acid at a position corresponding to position 16 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant comprises the substitution G16V of the polypeptide of SEQ ID NO: 11. In another aspect, the variant consists of the substitution G16V of the polypeptide of SEQ ID NO: 11.

In another aspect, the GTPase Ras2 variant has a sequence identity of at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent GTPase Ras2 protein.

In another aspect, the variant has at least 70%, e.g., at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the GTPase Ras2 protein of SEQ ID NO: 11.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

The present invention also relates to methods for obtaining a GTPase Ras2 variant, comprising: (a) introducing into a parent GTPase Ras2 protein a substitution at a position corresponding to position 16 of the polypeptide of SEQ ID NO: 11, wherein the GTPase Ras2 variant has constitutive regulatory activity under cellulase inducing conditions; and (b) recovering the variant.

The RAS GTPase ras2 variant in a filamentous fungal cell can be constructed by CRISPR genome editing, consisting of any RNA-guided DNA endonuclease using, for example, MAD7 (U.S. Pat. No. 9,982,279), MAD2 (U.S. Pat. No. 9,982,279), Cas9 (Doudna et al., 2014, Science 346: 1258096), "dead" Cas9 (dcas9; Qi et al., 2013, Cell 152(5): 1173), Cas9 nickase (Satomura et al. 2017, Sci. Rep. 7(1): 2095), or Cpf1 endonuclease (Zetsche et al. 2015, Cell 163(3): 759), directed to the nucleotide sequence of the gene by a suitably designed guide RNA and a suitably designed repair DNA.

The variants can also be prepared using any mutagenesis procedure known in the art, such as site-directed mutagenesis, synthetic gene construction, semi-synthetic gene construction, random mutagenesis, shuffling, etc.

Site-directed mutagenesis is a technique in which a mutation is introduced at a defined site in a polynucleotide encoding a parent GTPase Ras2 protein.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent GTPase Ras2 protein and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polypeptides of Interest

The polypeptide of interest can be any polypeptide native or foreign (heterologous) to the mutant filamentous fungal cell. The polypeptide can be encoded by a single gene or two or more genes. The term "heterologous polypeptide" is defined herein as a polypeptide that is not native to the cell; a native polypeptide in which structural modifications have been made to alter the native polypeptide, e.g., the protein sequence of a native polypeptide; or a native polypeptide whose expression is quantitatively altered as a result of a manipulation of the polynucleotide or host cell by recombinant DNA techniques, e.g., a different promoter, multiple copies of a DNA encoding the polypeptide. Thus, the present invention also encompasses, within the scope of the term "heterologous polypeptides," such recombinant production of native polypeptides, to the extent that such expression involves the use of genetic elements not native to the filamentous fungal cell, or use of native elements that have been manipulated to function in a manner that do not normally occur in the filamentous fungal cell.

In one aspect, the polypeptide is native to the filamentous fungal cell. In another aspect, the polypeptide is heterologous to the filamentous fungal cell.

The polypeptide can be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include fusion polypeptides, which comprise a combination of partial or complete polypeptide sequences obtained from at least two different polypeptides wherein one or more can be heterologous to the filamentous fungal cell. Polypeptides further include hybrid polypeptides comprising domains from two or more polypeptides, e.g., a binding domain from one polypeptide and a catalytic domain from another polypeptide. The domains may be fused at the N-terminus or the C-terminus.

In one aspect, the polypeptide is an antibody, an antigen, an antimicrobial peptide, an enzyme, a growth factor, a hormone, an immunomodulator, a neurotransmitter, a receptor, a reporter protein, a structural protein, or a transcription factor.

In another aspect, the polypeptide is an oxidoreductase, a transferase, a hydrolase, a lyase, an isomerase, or a ligase. In another aspect, the polypeptide is an acetylmannan esterase, acetylxylan esterase, aminopeptidase, alpha-amylase, arabinanase, arabinofuranosidase, carbohydrase, carboxypeptidase, catalase, cellobiohydrolase, cellulase, chitinase, coumaric acid esterase, cyclodextrin glycosyltransferase, cutinase, cyclodextrin glycosyltransferase, deamidase, deoxyribonuclease, dispersin, endoglucanase, esterase, feruloyl esterase, AA9 lytic polysaccharide monooxygenase, alpha-galactosidase, beta-galactosidase, glucocerebrosidase, glucose oxidase, alpha-glucosidase, beta-glucosidase, glucuronidase, glucuronoyl esterase, haloperoxidase, hemicellulase, invertase, isomerase, laccase, ligase, lipase, lysozyme, mannanase, mannosidase, mutanase, oxidase, pectinolytic enzyme, peroxidase, phosphodiesterase, phospholipase, phytase, phenoloxidase, polyphenoloxidase, proteolytic enzyme, ribonuclease, alpha-1,6-transglucosidase, transglutaminase, urokinase, xanthanase, xylanase, or beta-xylosidase.

In another aspect, the polypeptide is a cellulase. In another aspect, the cellulase is selected from the group consisting of an endoglucanase, a cellobiohydrolase, and a beta-glucosidase.

In another aspect, the polypeptide is a hemicellulase. In another aspect, the hemicellulase is selected from the group consisting of a xylanase, an acetylxylan esterase, a feruloyl esterase, an arabinofuranosidase, a xylosidase, and a glucuronidase.

In another aspect, the polypeptide is an endoglucanase. In another aspect, the polypeptide is a cellobiohydrolase. In another aspect, the polypeptide is a beta-glucosidase. In another aspect, the polypeptide is an AA9 lytic polysaccharide monooxygenase. In another aspect, the polypeptide is a xylanase. In another aspect, the polypeptide is a beta-xylosidase. In another aspect, the polypeptide is an acetyxylan esterase. In another aspect, the polypeptide is a feruloyl esterase. In another aspect, the polypeptide is an arabinofuranosidase. In another aspect, the polypeptide is a glucuronidase. In another aspect, the polypeptide is an acetylmannan esterase. In another aspect, the polypeptide is an arabinanase. In another aspect, the polypeptide is a coumaric acid esterase. In another aspect, the polypeptide is a galactosidase. In another aspect, the polypeptide is a glucuronoyl esterase. In another aspect, the polypeptide is a mannanase. In another aspect, the polypeptide is a mannosidase.

In the methods of the present invention, the mutant filamentous fungal cell is a recombinant cell, comprising a polynucleotide encoding a heterologous polypeptide, which is advantageously used in the recombinant production of the polypeptide. The cell is preferably transformed with a nucleic acid construct or an expression vector comprising the polynucleotide encoding the heterologous polypeptide followed by integration of the vector into the chromosome. "Transformation" means introducing a vector comprising the polynucleotide into a host cell so that the vector is maintained as a chromosomal integrant or as a self-replicating extra-chromosomal vector. Integration is generally considered to be an advantage as the polynucleotide is more likely to be stably maintained in the cell. Integration of the vector into the chromosome can occur by homologous recombination, non-homologous recombination, or transposition.

The polynucleotide encoding a heterologous polypeptide can be obtained from any prokaryotic, eukaryotic, or other source, e.g., archaeabacteria. For purposes of the present invention, the term "obtained from" as used herein in connection with a given source shall mean that the polypeptide is produced by the source or by a cell in which a gene from the source has been inserted.

The techniques used to isolate or clone a polynucleotide encoding a polypeptide of interest are known in the art and include isolation from genomic DNA, preparation from cDNA, or a combination thereof. The cloning of such a polynucleotide from such genomic DNA can be effected, e.g., by using the well-known polymerase chain reaction (PCR). See, for example, Innis et al., 1990, *PCR Protocols: A Guide to Methods and Application, Academic Press*, New York. The cloning procedures may involve excision and isolation of a desired nucleic acid fragment comprising the polynucleotide encoding the polypeptide, insertion of the fragment into a vector molecule, and incorporation of the recombinant vector into a mutant filamentous fungal cell of the present invention where one or more copies or clones of the polynucleotide will be replicated. The polynucleotide can be of genomic, cDNA, RNA, semisynthetic, synthetic origin, or any combinations thereof.

A polynucleotide encoding a polypeptide of interest can be introduced into a mutant filamentous fungal cell using methods standard in the art.

Parent Filamentous Fungal Cells

In the present invention, the parent filamentous fungal cell can be any filamentous fungal cell. The filamentous fungal cell can be a wild-type cell or a mutant thereof.

"Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic.

In one aspect, the parent filamentous fungal cell is an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosaperia, Magnaporthe, Melanocarpus, Meripilus, Mucor, Myceliophthora, Neocalfimasfix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* cell.

In an embodiment, the parent filamentous fungal cell is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Talaromyces emersonii, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* cell.

In another embodiment, the parent filamentous fungal cell is a *Myceliophthora thermophila* cell.

In another embodiment, the parent filamentous fungal cell is a *Talaromyces emersonii* cell.

In another embodiment, the parent filamentous fungal cell is a *Trichoderma harzianum* cell.

In another embodiment, the parent filamentous fungal cell is a *Trichoderma koningii* cell.

In another embodiment, the parent filamentous fungal cell is a *Trichoderma longibrachiatum* cell.

In another embodiment, the parent filamentous fungal cell is a *Trichoderma reesei* cell.

In another embodiment, the parent filamentous fungal cell is a *Trichoderma viride* cell.

In a preferred embodiment, the parent *Trichoderma reesei* cell is *Trichoderma reesei* Rut-C30.

In another preferred embodiment, the parent *Trichoderma reesei* cell is a mutant of *Trichoderma reesei*.

In another preferred embodiment, the parent *Trichoderma reesei* cell is a morphological mutant of *Trichoderma reesei* (see WO 97/26330).

In another preferred embodiment, the parent *Trichoderma reesei* cell is a protease-deficient mutant of *Trichoderma reesei* (see WO 2011/075677).

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and *Agricultural Research* Service Patent Culture Collection, Northern Regional Research Center (NRRL).

Mutant Filamentous Fungal Cells

A mutant filamentous fungal cell deficient in the production of a Rho-GTPase RacA protein can be constructed by reducing or eliminating (inactivating) expression of a gene encoding the Rho-GTPase RacA protein using methods well known in the art. A portion of the gene can be modified such as the coding region or a control sequence required for expression of the coding region. Such a control sequence of the gene can be a promoter sequence or a functional part thereof, i.e., a part that is sufficient for affecting expression of the gene. For example, a promoter sequence can be inactivated resulting in no expression or a weaker promoter can be substituted for the native promoter sequence to reduce expression of the coding sequence.

The mutant filamentous fungal cell can be constructed by gene deletion techniques to reduce or eliminate expression of the gene. Gene deletion techniques enable the partial or complete removal of the gene thereby reducing or eliminating its expression. In such methods, deletion of the gene is accomplished by homologous recombination using a plasmid that has been constructed to contiguously contain the 5' and 3' regions flanking the gene.

The mutant filamentous fungal cell can also be constructed by any RNA-guided DNA endonuclease using, for example, MAD7 (U.S. Pat. No. 9,982,279), MAD2 (U.S. Pat. No. 9,982,279), Cas9 (Doudna et al., 2014, *Science* 346: 1258096), "dead" Cas9 (dcas9; Qi et al., 2013, *Cell* 152(5): 1173), Cas9 nickase (Satomura et al. 2017, *Sci. Rep.* 7(1):

2095), or Cpf1 endonuclease (Zetsche et al. 2015, *Cell* 163(3): 759), directed to the nucleotide sequence of the gene by a suitably designed guide RNA.

The mutant filamentous fungal cell can also be constructed by introducing, substituting, and/or deleting one or more nucleotides in the gene or a control sequence thereof required for the transcription or translation thereof. For example, nucleotides can be inserted or removed for the introduction of a stop codon, the removal of the start codon, or a frame-shift of the open reading frame. Such a modification can be accomplished by site-directed mutagenesis or PCR generated mutagenesis in accordance with methods known in the art. See, for example, Botstein and Shortle, 1985, *Science* 229: 4719; Lo et al., 1985, *Proceedings of the National Academy of Sciences USA* 81: 2285; Higuchi et al., 1988, *Nucleic Acids Research* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The mutant filamentous fungal cell can also be constructed by gene disruption techniques by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product is the result. A disrupting construct can be simply a selectable marker gene accompanied by 5' and 3' regions homologous to the gene. The selectable marker enables identification of transformants containing the disrupted gene.

The mutant filamentous fungal cell can also be constructed by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence, which is then transformed into the filamentous fungal cell to produce a defective gene. By homologous recombination, the defective nucleotide sequence replaces the endogenous gene. It may be desirable that the defective nucleotide sequence also comprises a marker for selection of transformants containing the defective gene.

The mutant filamentous fungal cell can also be constructed by established anti-sense techniques using a nucleotide sequence complementary to the nucleotide sequence of the gene (Parish and Stoker, 1997, *FEMS Microbiology Letters* 154: 151-157). More specifically, expression of the gene can be reduced or eliminated by introducing a nucleotide sequence complementary to the nucleotide sequence of the gene, which can be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The mutant filamentous fungal cell can also be constructed by established RNA interference (RNAi) techniques (see, for example, WO 2005/056772 and WO 2008/080017).

The mutant filamentous fungal cell can be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp. 363-433, Academic Press, New York, 1970). Modification of the gene can be performed by subjecting the parent cell to mutagenesis and screening for mutant cells in which expression of the gene has been inactivated. The mutagenesis, which can be specific or random, can be performed, for example, by use of a suitable physical or chemical mutagenizing agent, use of a suitable oligonucleotide, or subjecting the DNA sequence to PCR generated mutagenesis. Furthermore, the mutagenesis can be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent cell to be mutagenized in the presence of the mutagenizing agent of choice under suitable conditions, and selecting for mutants exhibiting reduced or no expression of the gene.

Reduction or elimination of expression of a gene encoding a Rho-GTPase RacA protein can be measured by one of ordinary skill in the art through analysis of selected mRNA or transcript levels by well-known means, for example, quantitative real-time PCR (qRT-PCR), Northern blot hybridization, global gene expression profiling using cDNA or oligo array hybridization, or deep RNA sequencing (RNA-seq). Alternatively, modification of a gene encoding a Rho-GTPase RacA protein of the present invention can be determined by fungal spore PCR using a locus-specific primer as described herein.

In one aspect, the mutant is partially deficient in the production of the Rho-GTPase RacA protein compared to the parent filamentous fungal cell without the modification when cultivated under identical conditions. In a preferred aspect, the mutant produces at least 25% less, more preferably at least 50% less, even more preferably at least 75% less, and most preferably at least 95% less of the Rho-GTPase RacA protein than the parent filamentous fungal cell without the modification when cultivated under identical conditions.

In another aspect, the mutant is completely deficient in the production of the Rho-GTPase RacA protein compared to the parent filamentous fungal cell without the modification when cultivated under identical conditions. In other words, the gene encoding the Rho-GTPase RacA protein is inactivated (e.g., deletion, disruption, etc. of the gene).

A polynucleotide encoding a GTPase Ras2 variant can be introduced into the mutant filamentous fungal cell with a modified Rho-GTPase RacA gene using methods standard in the art as described herein.

Nucleic Acid Constructs

The present invention also relates to nucleic acid constructs comprising a polynucleotide encoding a polypeptide of interest operably linked to one or more control sequences that direct the expression of the coding sequence in a mutant filamentous fungal cell of the present invention under conditions compatible with the control sequences.

The polynucleotide may be manipulated in a variety of ways to provide for expression of the polypeptide of interest. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a mutant filamentous fungal cell of the present invention for expression of a polynucleotide encoding the polypeptide of interest. The promoter contains transcriptional control sequences that mediate the expression of the polypeptide of interest. The promoter may be any polynucleotide that shows transcriptional activity in the mutant cell including mutant, truncated, and hybrid promoters, and may be obtained from genes encoding extracellular or intracellular polypeptides either homologous or heterologous to the mutant cell.

Examples of suitable promoters for directing transcription of the nucleic acid constructs in the mutant filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by the mutant filamentous fungal host cell to terminate transcription. The terminator is operably linked to the 3'-terminus of the polynucleotide encoding the polypeptide of interest. Any terminator that is functional in a mutant filamentous fungal host cell of the present invention may be used.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by the mutant filamentous fungal host cell. The leader is operably linked to the 5'-terminus of the polynucleotide encoding the polypeptide of interest. Any leader that is functional in the mutant filamentous fungal host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the mutant filamentous fungal host cell as a signal to add polyadenosine residues to transcribed mRNA. Any polyadenylation sequence that is functional in the mutant filamentous fungal host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of the polypeptide of interest and directs the polypeptide of interest into the cell's secretory pathway. The 5'-end of the coding sequence of the polynucleotide may inherently contain a signal peptide coding sequence naturally linked in translation reading frame with the segment of the coding sequence that encodes the polypeptide of interest. Alternatively, the 5'-end of the coding sequence may contain a signal peptide coding sequence that is foreign (heterologous) to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide of interest. However, any signal peptide coding sequence that directs the expressed polypeptide of interest into the secretory pathway of a host cell may be used.

Effective signal peptide coding sequences for filamentous fungal host cells are the signal peptide coding sequences obtained from the genes for *Aspergillus niger* neutral amylase, *Aspergillus nigerglucoamylase, Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of the polypeptide of interest. The resultant polypeptide is known as a proenzyme or propolypeptide (or a zymogen in some cases). A propolypeptide is generally inactive and can be converted to an active polypeptide of interest by catalytic or autocatalytic cleavage of the propeptide from the propolypeptide. The propeptide coding sequence may be obtained from the genes for *Myceliophthora thermophila* laccase (WO 95/33836) and *Rhizomucor miehei* aspartic proteinase.

Where both signal peptide and propeptide sequences are present, the propeptide sequence is positioned next to the N-terminus of the polypeptide of interest and the signal peptide sequence is positioned next to the N-terminus of the propeptide sequence.

It may also be desirable to add regulatory sequences that regulate expression of the polypeptide of interest relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide of interest would be operably linked to the regulatory sequence.

Expression Vectors

The present invention also relates to recombinant expression vectors comprising a polynucleotide encoding a polypeptide of interest, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide of interest at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hpt, and pyrG genes.

The selectable marker may be a dual selectable marker system as described in WO 2010/039889. In one aspect, the dual selectable marker is a hpt-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide of interest or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the polypeptide of interest. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described herein to construct the recombinant expression vectors are well known to one skilled in the art (see, e.g., J. Sambrook, E. F. Fritsch, and T. Maniatis, 1989, *Molecular Cloning, A Laboratory Manual,* 2d edition, Cold Spring Harbor, New York).

A vector can be introduced, e.g., by transformation, into the filamentous fungal cell so that the vector is maintained as a chromosomal integrant or as a self-replicating extrachromosomal vector. Integration is generally considered to be an advantage as the nucleotide sequence is more likely to be stably maintained in the cell. Integration of the vector into the chromosome occurs by homologous recombination, non-homologous recombination, or transposition.

The introduction of an expression vector into the filamentous fungal cell may involve a process consisting of protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

Methods of Producing a Polypeptide of Interest

The present invention also relates to a method of producing a polypeptide of interest, comprising (a) cultivating a mutant filamentous fungal cell of the present invention for production of the polypeptide of interest, and optionally (b) recovering the polypeptide of interest.

The mutant filamentous fungal cell is cultivated in a nutrient medium suitable for production of the polypeptide using methods known in the art. For example, the filamentous fungal cell can be cultivated by shake flask cultivation, or small-scale or large-scale fermentation (including continuous, batch, fed-batch, or solid-state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide of interest can be detected using methods known in the art that are specific for the polypeptide. These detection methods include, but are not limited to, use of specific antibodies, formation of an enzyme product, or disappearance of an enzyme substrate. For example, an enzyme assay can be used to determine the activity of the polypeptide.

The increase in productivity of the polypeptide of interest by the mutant filamentous fungal cell can be measured using the methods above. The increase in expression of the gene encoding the polypeptide of interest can be determined by analysis of selected mRNA or transcript levels by well-known means, for example, quantitative real-time PCR (qRT-PCR), Northern blot hybridization, global gene expression profiling using cDNA or oligo array hybridization, or deep RNA sequencing (RNA-seq).

The polypeptide can be recovered using methods known in the art. For example, the polypeptide can be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

The present invention is further described by the following examples that should not be construed as limiting the scope of the invention.

EXAMPLES

Strains

*Trichoderma reesei* strain BTR213 is described in WO 2013/086633.

*Trichoderma reesei* strain O44N7J, which is a BTR213 derivative strain expressing the heterologous *Aspergillus fumigatus* cellobiohydrolase I and *Aspergillus fumigatus* beta-glucosidase genes.

Media and Solutions

COVE2 plates were composed of 30 g of sucrose, 20 ml of COVE salts solution, 10 ml 1 M acetamide, 25 g of Noble agar, and deionized water to 1 liter.

COVE salts solution was composed of 26 g of KCl, 26 g of $MgSO_4 \cdot 7H_2O$, 76 g of $KH_2PO_4$, 50 ml COVE trace metals solution, and deionized water to 1 liter.

COVE trace metals solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$. 0.7 g of $MnSO_4 \cdot H_2O$, 0.8 g of $Na_2MoO_2 \cdot 2H_2O$, 10 g of $ZnSO_4 \cdot 7H_2O$, and deionized water to 1 liter.

Fermentation batch medium was composed of 15.1 g of dextrose, 40 g of soy grits, 8 g of $(NH_4)_2SO_4$, 3 g of $K_2HPO_4$, 8 g of $K_2SO_4$, 3 g of $CaCO_3$, 8 g of $MgSO_4 \cdot 7H_2O$, 1 g of citric acid $H_2O$, 5.2 ml of 85% phosphoric acid, 1 ml of anti-foam, 14.7 ml of trace metals solution, and deionized water to 1 liter. The trace metals solution was composed of 26.1 g of $FeSO_4 \cdot 7H_2O$, 5.5 g of $ZnSO_4 \cdot 7H_2O$, 6.6 g of $MnSO_4 \cdot H_2O$, 2.6 g of $CuSO_4 \cdot 5H_2O$, 2 g of citric acid $H_2O$, and deionized water to 1 liter.

LB+Amp medium was composed of 10 g of tryptone, 5 g of yeast extract, 5 g of sodium chloride, 50 mg of ampicillin (filter sterilized, added after autoclaving), and deionized water to 1 liter.

PDA plates were composed of 39 g of potato dextrose agar (Difco) and deionized water to 1 liter.

PDA+1 M sucrose plates were composed of 39 g of potato dextrose agar (Difco), 342.30 g of sucrose, and deionized water to 1 liter.

PDA+hygromycin B overlay was composed of 175 μl of hygromycin B (Invitrogen, 50 mg/ml in PBS buffer) and 250 ml of sterile PDA plate medium.

PEG buffer was composed of 50% polyethylene glycol (PEG) 4000, 10 mM Tris-HCl pH 7.5, and 10 mM $CaCl_2$) in deionized water. The solution is filter sterilized.

Shake flask medium was composed of 20 g of glycerol, 10 g of soy grits, 10 g of $(NH_4)_2SO_4$, 2 g of $KH_2PO_4$, 4 g of $MgSO_4 \cdot 7H_2O$, 0.5 g $CaCO_3$, 0.2 ml of trace metals solution, and deionized water to 1 liter. The trace metals solution was composed of 26.1 g of $FeSO_4 \cdot 7H_2O$, 5.5 g of $ZnSO_4 \cdot 7H_2O$, 6.6 g of $MnSO_4 \cdot H_2O$, 2.6 g of $CuSO_4 \cdot 5H_2O$, 2 g of citric acid $H_2O$, and deionized water to 1 liter.

STC was composed of 1 M sorbitol, 10 mM Tris pH 7.5, and 10 mM $CaCl_2$) in deionized water.

TBE buffer was composed of 10.8 g of Tris Base, 5 g of boric acid, 4 ml of 0.5 M EDTA pH 8, and deionized water to 1 liter.

TE buffer was composed of 1 M Tris pH 8.0 and 0.5 M EDTA pH 8.0.

2×YT+Amp plates were composed of 16 g of tryptone, 10 g of yeast extract, 5 g of NaCl, 15 g of Bacto agar, 1 ml of ampicillin at 100 mg/ml (filter sterilized and added after autoclaving), and deionized water to 1 liter.

YP medium was composed of 1% yeast extract and 2% peptone in deionized water.

YPD medium was composed of 1% yeast extract, 2% peptone, and 2% glucose in deionized water.

Example 1: *Trichoderma reesei* Protoplast Generation

Protoplast preparation and transformation of *Trichoderma reesei* were performed using a protocol similar to Penttila et al., 1987, *Gene* 61: 155-164. Briefly, *T. reesei* was cultivated in two shake flasks, each containing 25 ml of YPD medium, at 27° C. for 17 hours with gentle agitation at 90 rpm. Mycelia were collected by filtration using a Vacuum Driven Disposable Filtration System (Millipore) and washed twice with deionized water and twice with 1.2 M sorbitol. Protoplasts were generated by suspending the washed mycelia in 30 ml of 1.2 M sorbitol containing 5 mg of YATALASE™ (Takara Bio USA, Inc.) per ml and 0.5 mg of chitinase (Sigma Chemical Co.) per ml for 60-75 minutes at 34° C. with gentle shaking at 90 rpm. Protoplasts were collected by centrifugation at 834×g for 7 minutes and washed twice with cold 1.2 M sorbitol. The protoplasts were counted using a hemocytometer and re-suspended to a final concentration of $1×10^8$ protoplasts per ml of STC. Aliquots (1.1 ml) of the protoplast solution were placed in a MR. FROSTY™ freezing container (Thermo Fisher Scientific) at −80° C. for later use.

Example 2: CRISPR/Mad7 Backbone Vector pGMEr263

Plasmid pGMEr263 was used as a backbone vector for genome editing in *Trichoderma reesei*, i.e., inactivation of the racA gene (SEQ ID NO: 1 for the DNA sequence and SEQ ID NO: 2 for the deduced amino acid sequence).

Plasmid pGMEr263 (SEQ ID NO: 3, FIG. 1) is a CRISPR/MAD7 expression plasmid used to clone protospacers into Bgl II digested pGMEr263 using an NEBUILDER® HiFi DNA Assembly Cloning Kit (New England Biolabs Inc.). Plasmid pGMEr263 contains a *Eubacterium* rectale Mad7 protein coding sequence (nucleotides 9663-13,478 in pGMEr263) codon-optimized for use in *Aspergillus niger* and a SV40 nuclear localization signal (NLS; nucleotides 13,455-13,478) at the 3′ end of the *E. rectale* Mad7 open reading frame to ensure that Mad7 is localized to the nucleus. Expression of the *E. rectale* Mad7 is under control of the *Aspergillus nidulans* tef1 promoter (nucleotides 8777-9662) and terminator (nucleotides 13,479-13,883) from pFC330-333 (Nødvig et al., 2015, *PLoS One* 10(7): 1-18).

Plasmid pGMEr263 also has all the elements for single guide RNA (sgRNA) expression, which consists of the *Magnaporthe oryzae* U6-2 promoter (nucleotides 7949-8448), *Aspergillus fumigatus* tRNAgly(GCC)1-6 sequence with the region downstream of the structural tRNA removed (nucleotides 8449-8539), *E. rectale* single guide RNA sequence (nucleotides 8540-8560), Bgl II restriction enzyme recognition sequence (nucleotides 8557-8562), and *M. oryzae* U6-2 terminator (nucleotides 8562-8776).

For selection in *T. reesei*, plasmid pGMEr263 contains the hygromycin phosphotransferase (hpt) gene from pHT1 (Cummings et al., 1999, *Curr. Genet.* 36: 371) (nucleotides 6475-7506), conferring resistance to hygromycin B, and the autonomous maintenance in *Aspergillus* (AMA1) sequence (Gems et al., 1991, *Gene* 98: 61-67) (nucleotides 332-6056) for extrachromosomal replication of pGMEr263 in *T. reesei*. The hygromycin resistance gene (CDS nucleotides 6475-7506) is under transcriptional control of the *Coprinus cinereus* beta-tubulin promoter (nucleotides 6082-6474) and terminator (nucleotides 7503-7929). The single guide RNA and the Mad7-SV40 NLS expression elements in pGMEr263 were confirmed by DNA sequencing with a Model 377 XL Automated DNA Sequencer (Applied Biosystems Inc.) using dye-terminator chemistry (Giesecke et al., 1992, *J. Virol. Methods* 38(1): 47-60).

Example 3: Construction of pGMEr263-racA-Proto3

Plasmid vector preparation. Plasmid pGMEr263 was digested with the restriction enzyme Bgl II (ANZA™ 19 Bgl II, Thermo Fisher Scientific). The restriction reaction contained 15 μg of pGMEr263 plasmid DNA, 1× ANZA™ buffer, 100 units of Bgl II, and sterile Milli-Q water up to 200 μl final volume. The reaction was incubated at 37° C. for 3 hours. Following restriction enzyme digestion, the digest was subjected to 0.8% agarose gel electrophoresis in TBE buffer where a band representing the digested pGMEr263 was excised from the gel and purified using a NUCLEO-SPIN® Gel and PCR Clean-up Kit (Macherey-Nagel) according to the manufacturer's instructions.

Protospacer design. A protospacer was selected by finding an appropriate protospacer adjacent motif (PAM) with the sequence TTTV in the *T. reesei* racA gene, where V represents nucleotides A, C, or G. Once an appropriate PAM site was identified, the twenty-one base-pairs immediately adjacent to the 3′ side of the PAM site were selected as the protospacer. Protospacers that contained more than three contiguous T nucleotides were rejected to avoid possible stuttering of RNA polymerase. A twenty-one base-pair protospacer, immediately adjacent to PAM TTTC, identified as racA-proto3 (SEQ ID NO: 4) was designed for the locus of the *Trichoderma reesei* racA gene to direct the Mad7 enzyme to the target site located at the 3′ end of the racA gene third exon and create a double stranded break.

```
racA-proto3:
                              (SEQ ID NO: 4)
CCCGGAGAGTACATCCCGACC
```

The protospacer with its extension sequences as shown below (oligo 1229348, SEQ ID NO: 5) was synthesized as a single-stranded oligonucleotide by Thermo Fisher Scientific, Inc. The underlined sequence in the oligonucleotide highlights the twenty-one nucleotide protospacer. The protospacer oligonucleotide was diluted to a final working concentration of 1 μM.

```
Oligo 1229348:
                              (SEQ ID NO: 5)
ATTCACGGATGATGCAGGAATTTCTACTCTTGTAGATCCCGGAGAGTAC
ATCCCGACCTTTTTTTGGCTCTTGGGTTCGAACTGCCCAAGGCCCA
```

The sequences immediately adjacent to the protospacer racA-proto3 region in oligo 1229348 represent the 5′ and the 3′ regions of homology with Bgl II linearized plasmid pGMEr263, respectively. Such regions of homology are needed to clone the protospacer racA-proto3 into plasmid pGMEr263, creating a functional Mad7 guide RNA expression cassette, targeting the racA gene.

Figure 2:
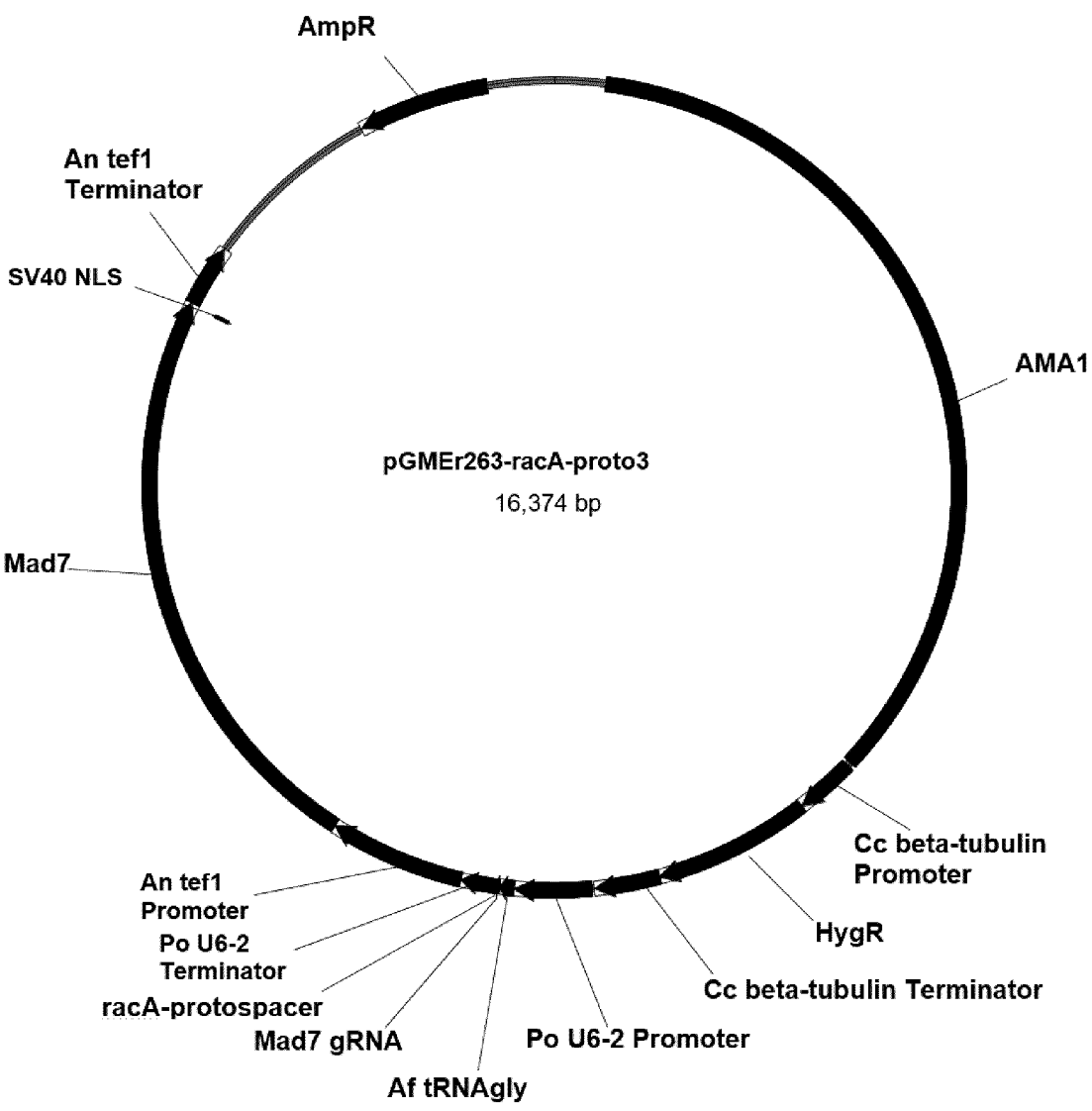
FIG. 2 shows a map of plasmid pGMEr263-racA-proto3.

Assembly of protospacers. The protospacer racA-proto3 was cloned into Bgl II linearized pGMEr263 using an NEBUILDER® HiFi DNA Assembly Master Mix Kit (New England Biolabs) in a total volume of 10 μl composed of 1×NEBUILDER® HiFi Assembly Master Mix (New England Biolabs), 0.05 μmol of Bgl II-digested pGMEr263, 1.0 μl of protospacer oligo 1229348 (1 μM), and sterile Milli-Q water to a final volume of 20 μl. The reaction was incubated at 50° C. for 15 minutes and then placed on ice. Two μl of the assembly reaction were used to transform 50 μl of STELLAR™ chemically competent E. coli cells (Clontech Laboratories, Inc.) according to the manufacturer's instructions. Each transformation reaction was spread onto two 2×YT+Amp plates and incubated at 37° C. overnight. Putative transformant colonies were isolated from the selection plates and plasmid DNA was prepared from each one using a QIAprep Spin Miniprep Kit (QIAGEN Inc.) and screened for insertion of the desired protospacer by sequencing using primer 1228659 (SEQ ID NO: 6) shown below. A plasmid having the correct protospacer sequence was designated pGMEr263-racA-proto3 (SEQ ID NO: 7, FIG. 2).

```
       Primer 1228659:
                         (SEQ ID NO: 6)
       CTTGCTTGTCAAGCAATGGC
```

Example 4: Design of the Double-Stranded Oligo Donor DNA Needed to Inactivate the racA Gene in *Trichoderma reesei*

To inactivate the racA gene (SEQ ID NO: 1) in *Trichoderma reesei* via Mad7 genome editing using CRISPR/Mad7 plasmid pGMEr263-racA-proto3, the reverse and complementary single-stranded oligos 1229227 and 1229228 shown below were synthesized by Thermo Fisher Scientific, Inc.

```
Oligo 1229227:
                         (SEQ ID NO: 8)
TTTTGCGCAGACCTGTCTTCTCATCTCGTACACGACCAATTAATGATGT

TAGTTTCGCCTCCCGATATGACACAACCAACTCTGGCTCGCGAATA

Oligo 1229228:
                         (SEQ ID NO: 9)
TATTCGCGAGCCAGAGTTGGTTGTGTCATATCGGGAGGCGAAACTAACA

TCATTAATTGGTCGTGTACGAGATGAGAAGACAGGTCTGCGCAAAA
```

The 1229227 and 1229228 oligos were annealed by a 5 minutes incubation at 98° C. in a Model C1000 TOUCH™ Thermal Cycler (Bio-Rad Laboratories), followed by a slow cool down step at room temperature. The resulting double-stranded oligo designated racA-9227/9228 was used to repair the double-stranded cut generated by the Mad7 endonuclease guided to the *Trichoderma reesei* host racA locus by the gRNA encoded in plasmid pGMEr263-racA-proto3. The racA locus genome editing results in the deletion of the PAM TTTC motif (4 nucleotides), the deletion of the protospacer region (21 nucleotides), the addition of the first stop codon TAA at position 32 and an ORF frame shift which introduces many additional stop codons in the downstream portion of the gene.

Example 5: Construction of pGMEr263-ras2G16V-Proto

Plasmid pGMEr263 was used as a backbone vector to construct plasmid pGMEr263-ras2G16V-proto for modification of the *Trichoderma reesei* ras2 gene (SEQ ID NO: 10 for the DNA sequence and SEQ ID NO: 11 for the deduced amino acid sequence).

Plasmid vector preparation. Plasmid pGMEr263 was digested with the restriction enzyme Bgl II. The restriction reaction contained 15 μg of pGMEr263 plasmid DNA, 1× ANZA™ buffer, 100 units of Bgl II, and sterile Milli-Q water up to 200 μl final volume. The reaction was incubated at 37° C. for 3 hours. Following restriction enzyme digestion, the digest was subjected to 0.8% agarose gel electrophoresis in TBE buffer where the band representing the digested pGMEr263 was excised from the gel and purified using a NUCLEOSPIN® Gel and PCR Clean-up Kit according to the manufacturer's instructions.

Protospacer design. A protospacer was selected by finding an appropriate protospacer adjacent motif (PAM) with the sequence TTTV in the *T. reesei* ras2G gene, where V represents nucleotides A, C, or G. Once an appropriate PAM site was identified, the twenty-one base-pairs immediately adjacent to the 3' side of the PAM site were selected as the protospacer. Protospacers that contained more than three contiguous T nucleotides were rejected to avoid possible stuttering of RNA polymerase. A twenty-one base-pair protospacer, identified as ras2G16V-proto shown below (SEQ ID NO: 12), was designed for the ras2 gene to direct the Mad7 endonuclease cut to the 5' end of the ras2 gene first exon. Protospacer ras2G16V-proto was selected by finding an appropriate protospacer adjacent motif (PAM) with the sequence TTTG, located eight nucleotides upstream of the ras2 gene ATG start codon. Protospacer ras2G16V-proto sits 32 nucleotides upstream of the target glycine at position 16 of SEQ ID NO: 11.

```
       ras2G16V-proto:
                         (SEQ ID NO: 12)
       CGCCCATCATGGCGGGCAGAA
```

The protospacer with its extension sequences shown below (oligo 1230370, SEQ ID NO: 13) was synthesized as a single-stranded oligonucleotide by Thermo Fisher Scientific, Inc. The underlined sequence in the oligonucleotide highlights the twenty-one nucleotide protospacer. The protospacer oligonucleotide was diluted to a final working concentration of 1 μM.

```
Oligo 1230370
                         (SEQ ID NO: 13)
ATTCACGGATGATGCAGGAATTTCTACTCTTGTAGATCGCCCATCATGG

CGGGCAGAATTTTTTTGGCTCTTGGGTTCGAACTGCCCAAGGCCCA
```

The sequences immediately adjacent to the protospacer ras2G16V-proto region in oligo 1230370 represent the 5' and the 3' regions of homology with Bgl II linearized plasmid pGMEr263, respectively. Such regions of homology are needed to clone the ras2G16V-proto protospacer into plasmid pGMEr263, creating a functional Mad7 guide RNA expression cassette, targeting the ras2 gene.

Figure 3:
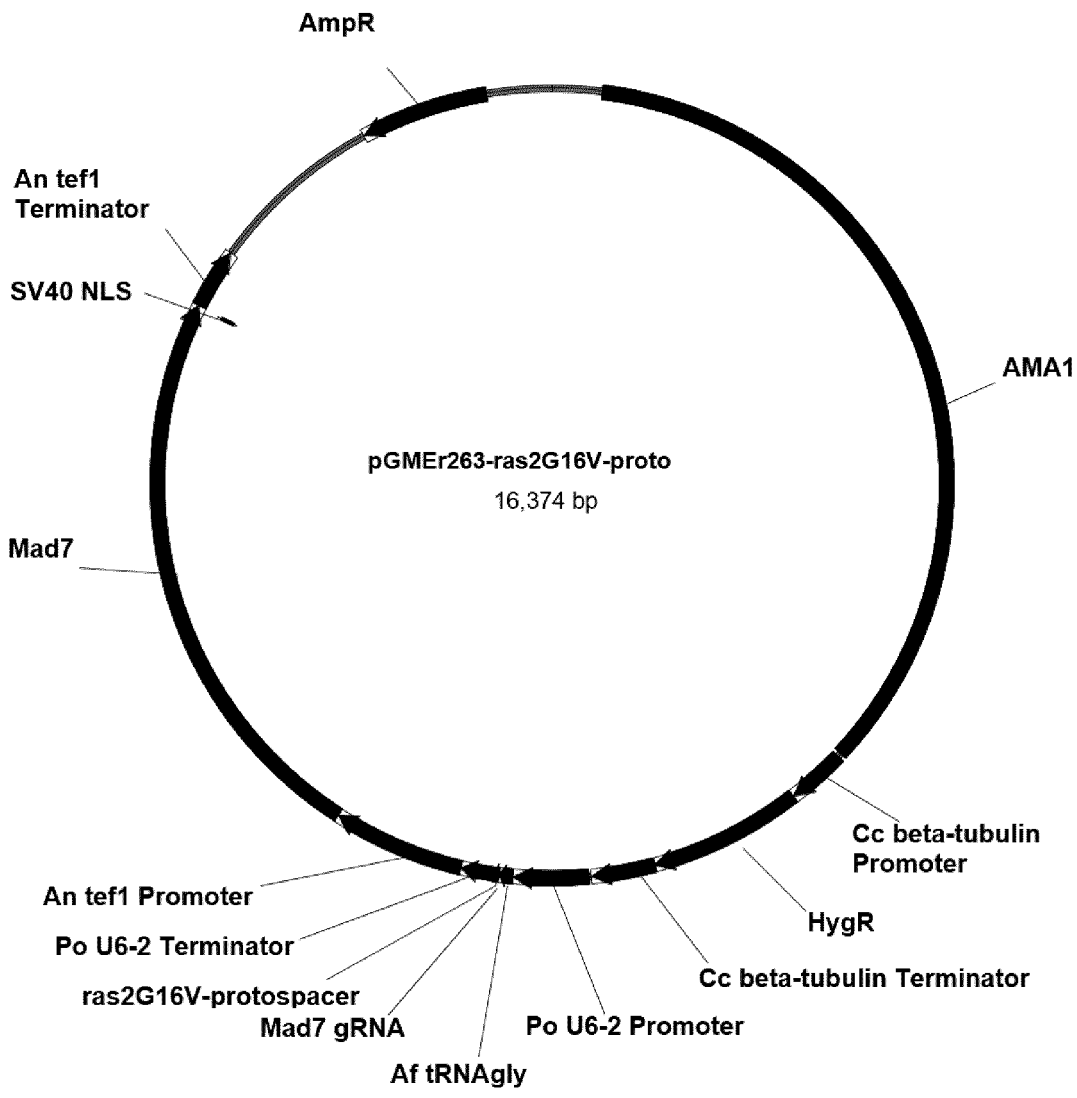
FIG. 3 shows a map of plasmid pGMEr263-ras2G16V-proto.

Assembly of protospacer. The ras2G16V-proto protospacer was cloned into Bgl II linearized pGMEr263 using an NEBuilder® HiFi DNA Assembly Master Mix in a total volume of 10 μl composed of 1× NEBuilder® HiFi Assembly Master Mix, 0.05 μmol of Bgl II-digested pGMEr263, 1.0 μl of protospacer oligo (1 μM) and sterile Milli-Q water to a final volume of 20 μl. The reaction was incubated at 50° C. for 15 minutes and then placed on ice. Two μl of the assembly reaction was used to transform 50 μl of STEL- LAR™ chemically competent *E. coli* cells according to the manufacturer's instructions. Each transformation reaction was spread onto two 2×YT+Amp plates and incubated at 37° C. overnight. Putative transformant colonies were isolated from the selection plates and plasmid DNA was prepared from each one using a QIAprep Spin Miniprep Kit (QIA-GEN Inc.). The plasmids were screened for insertion of the desired protospacer by sequencing using primer 1228659 (SEQ ID NO: 14) shown below. A plasmid having the correct protospacer sequence was designated pGMEr263-ras2G16V-proto (SEQ ID NO: 15, FIG. 3).

```
Primer 1228659:
                              (SEQ ID NO: 14)
CTTGCTTGTCAAGCAATGGC
```

Example 6: Design of the Double-Stranded Oligo Donor DNA Needed to Generate the ras2$_{G16V}$ Gene Variant in *T. reesei*

To introduce the point mutation G47T into the native *T. reesei* ras2 gene via Mad7 genome editing using CRISPR/Mad7 plasmid pGMEr263-ras2G16V-proto, the reverse and complementary single-stranded oligos ras2G16-donorF and ras2G16-donorR shown below were synthesized by IDT®, Integrated DNA Technologies

```
Oligo ras2G16-donorF:
                              (SEQ ID NO: 16)
GGTCGCTCCTCAACCGCTGACTCTTTGCGCCCATCATGGCAGGAAGGAT

GGTGCTGTACAAGCTGGTGGTGCTGGGAGACGTTGGTGTCGGTAAGACG

GCCCTGACCATCCAGCTGTGCCTGCAGCACTTCGTCGAGACG

Oligo ras2G16-donorR:
                              (SEQ ID NO: 17)
CGTCTCGACGAAGTGCTGCAGGCACAGCTGGATGGTCAGGGCCGTCTTA

CCGACACCAACGTCTCCCAGCACCACCAGCTTGTACAGCACCATCCTTC

CTGCCATGATGGGCGCAAAGAGTCAGCGGTTGAGGAGCGACC
```

The two reverse and complementary single-stranded oligos ras2G16-donorF and ras2G16-donorR were annealed by incubation at 98° C. for 5 minutes in a TOUCH™ Thermal Cycler, followed by a slow cool down step at room temperature. The resulting double-stranded oligo designated ras2$_{G16V}$-donor was used to repair the double stranded cut generated by the Mad7 endonuclease guided to the *Trichoderma reesei* host ras2 locus by the gRNA encoded in plasmid pGMEr263-ras2$_{G16V}$-proto. The ras2 locus genome editing resulted in the insertion of the point mutation G47T responsible for the amino acid change G16V (glycine at position 16 changed to valine). Furthermore, three silent mutations were also introduced at the 5' end of the ras2 CDS, in particular nucleotide 6 was changed from a G to an A, nucleotide 9 was changed from a C to an A, and nucleotide 12 was changed from an A to a G. These three silent mutations are all included in the ras2$_{G16V}$-proto region and they serve to avoid Mad7 genome re-cutting once the desired SNV at position 47 is introduced (SEQ ID NO: 18 for the DNA sequence of the mutant ras2$_{G16V}$ gene and SEQ ID NO: 19 for the deduced amino acid sequence of the ras2$_{G16V}$ variant).

Example 7: Co-Transformation of pGMEr2630racA-Proto3, pGMEr263-ras2G16V-Proto, and Double-Stranded Donor Oligonucleotides The purpose of this experiment was to introduce inactivation of the racA gene and the ras2$_{G16V}$ variant into *Trichoderma reesei*, via Mad7 genome editing, individually and in combination, to evaluate the effect on cellulase expression. The pGMEr263-racA-proto3 and the pGMEr263-ras2G16V-proto plasmids are autonomously replicating plasmids (contain AMA1) that express Mad7, a sgRNA construct that targets specific sequences of the racA locus and the ras2 locus, respectively, in *T. reesei*, and a hpt selection marker (hygromycin B resistance). The respective donor DNA fragments were racA-9227/9228 (Example 4) and ras2$_{G16V}$-donor (Example 6), and they were used as double-stranded oligos. Donor DNA racA-9227/9228, used in combination with Mad7 plasmid pGMER263-racA-proto3, replaced the PAM and the protospacer regions at the racA locus with a TAA stop codon, creating an intentional frame shift leading to the racA gene inactivation. Donor DNA ras2-donor, used in combination with Mad7 plasmid pGMER263-ras2G16V-proto, modified the Ras2 protein amino acid sequence by replacing the amino acid glycine at position 16 with the amino acid valine, making the ras2 gene constitutively active under cellulase expression inducing conditions.

Plasmid pGMEr263-racA-proto3, pGMEr263-ras2G16V-proto, donor DNA racA-9227/9228, and donor DNA ras2-donor were co-transformed into a *Trichoderma reesei* BTR213 host strain O44N7J expressing the heterologous *Aspergillus fumigatus* cellobiohydrolase I gene and *Aspergillus fumigatus* beta-glucosidase gene. O44N7J protoplasts were thawed on ice. For each transformation, approximately 2 µg of both plasmid DNAs and 6 µl of each double-stranded donor DNA molecules (50 µM) were added to 100 µl of thawed protoplast solution and mixed gently. PEG buffer (250 µl) was added, and the reaction was mixed and incubated at 34° C. for 30 minutes. Following transformation, 1 ml of STC was added to each transformation reaction and the contents were spread onto PDA+1 M sucrose plates and incubated overnight at 37° C. The next day PDA+hygromycin B overlay was added to a final concentration of 10 µg/ml hygromycin B and the plates were incubated at 30° C. for 5-7 days. Approximately, 15-20 transformants were obtained for each transformation. To determine editing frequency, a few hygromycin-resistant colonies were picked from each transformation plate and transferred to PDA plates and incubated at 30° C. for 5-7 days. For each transformant, spores were collected with a sterile 1 µl inoculation loop and suspended in 20 µl of Dilution buffer (PHIRE™ Plant Direct PCR Kit, Thermo Scientific) in a thin-walled PCR tube. A region covering the racA and the ras2 target sites was amplified using the PHIRE™ Plant Direct PCR Kit (Thermo Scientific) with primer pairs 1230867 (SEQ ID NO: 20)+1230870 (SEQ ID NO: 21) and 1230863 (SEQ ID NO: 22)+1230864 (SEQ ID NO: 23), respectively, shown below.

```
Primer 1230867:
                              (SEQ ID NO: 20)
ATGGCGCAAGCTGGAGTGCA Primer 1230870:
                              (SEQ ID NO: 21)
CGAATAGCCTCGTCAAAGAC
```

```
-continued
Primer 1230863:
                                  (SEQ ID NO: 22)
CAGCTTCCCGTCGCCGCCCA Primer 1230864:
                                  (SEQ ID NO: 23)
CTGCTTGCGGTATGAGTCCTC
```

Each PCR was composed of 1 µl of spore suspension, 10 µmol of each primer, 10 µl of 2× PHIRE™ Plant PCR Buffer (PHIRE™ Plant Direct PCR Kit, Thermo Scientific), 0.4 µl of PHIRE™ Hot Start II DNA Polymerase (PHIRE™ Plant Direct PCR Kit, Thermo Scientific), and sterile Milli-Q H$_2$O to a final volume of 20 µl. The reactions were incubated in a TOUCH™ Thermal Cycler programmed for 1 cycle at 98° C. for 3 minutes; 40 cycles each at 98° C. for 5 seconds and 72° C. for 1 minute 20 seconds; and one cycle at 72° C. for 5 minutes.

To identify edited transformants the PCR products were sequenced after a clean-up process using the ExoSAP-IT reagent (Affimetrix, Inc.). Five µl of post-PCR reaction were mixed with 2 µl of ExoSAP-IT reagent (Affimetrix, Inc.) for a combined 7 µl reaction volume. The mix was incubated at 37° C. for 15 minutes, and then incubated at 80° C. for 15 minutes to inactivate the ExoSAP-IT reagent. Each ExoSAP-IT treated PCR product was sequenced to confirm the desired genome editing, using sequencing primer 1230871 (SEQ ID NO: 24) for the racA locus and sequencing primer 1230865 (SEQ ID NO: 25) for the ras2 locus shown below.

```
Primer 1230871:
                                  (SEQ ID NO: 24)
GACCTCCTTGACGTAGTTGA Primer 1230865:
                                  (SEQ ID NO: 25)
GCTTCTGCTTCTGCTTCTGC
```

Sequencing results identified three different edited strains: single mutant *T. reesei* O83E59 (O44N7J with the racA knock-out), single mutant *T. reesei* O83E58 (O44N7J with the raS2$_{G16V}$ variant), and the double mutant *T. reesei* O838XE (O44N7J with both edited loci, racA knock-out and ras2$_{G16V}$ variant).

Example 8: Whole Genome Sequencing of Mutant *Trichoderma reesei* Strains O83E59, O83E58 and O838XE Each of the three mutant *T. reesei* strains O83E59, O83E58, and O838XE (Example 7) were grown in 5 ml of YPD medium in 14 ml tubes for 3 days at 30° C. with shaking at 300 rpm. The mycelia were collected by centrifugation and the genomic DNA was purified using a MAGMAX™ Plant DNA Kit (Thermo Scientific) in a KINGFISHEr™ Duo Prime (Thermo Scientific). The final genomic DNA concentration was measured using a Qubit Fluorometric Quantification apparatus (Thermo Scientific), and, for each mutant strain, 20 µl (5 ng/µl) of DNA solution was submitted for NGS sequencing analysis. Each genomic DNA solution was used to create paired-end sequencing libraries and sequenced using 2×150 bp chemistry on a NEXTSEQ™ 500 System (Illumina Inc.). Sequence analysis was performed with the CLC Genomics Workbench version 11.0.1 (QIAGEN Inc.). Reads were trimmed using the Trim Reads module. For each sample, 100,000 trimmed reads were sampled using the Sample Reads module. Reads were mapped to a model of the racA and the ras2 edited loci using the Map Reads to Reference module with a high-stringency setting. Overall, 85-96% of the reads were successfully mapped producing 100% coverage of the model. Editing and transfer of mutations were analyzed with the Basic Variant Detection module and the desired genomic changes were confirmed in all the mutant strains.

Example 9: Phenotypic Evaluation of the Rac/Ras Mutant *Trichoderma reesei* Strains Single mutant *T. reesei* O83E59, single mutant *T. reesei* O83E58, double mutant *T. reesei* O838XE and parent *T. reesei* strain O44N7J were grown on COVE2 agar plates and phenotypical changes were recorded. Parent strain *T. reesei* O44N7J exhibited the characteristic *T. reesei* phenotype on COVE2 plates: heavily sporulating and mycelial growth spread on the entire plate surface. Single mutant O83E58 (ras2$_{G16V}$ variant) appeared heavily sporulating but the mycelial growth did not reach the edge of the plate. Single mutant *T. reesei* O83E59 (racA knock-out) had decreased sporulation and growth was restricted to the middle of the plate. Double mutant *T. reesei* O838XE showed the most extreme phenotypical changes, which was heavily sporulating but with a severely constricted mycelial growth limited to the center of the plate.

Example 10: Fed Batch Fermentations

The mutant *T. reesei* strains O83E59, O83E58, and O838XE and parent *T. reesei* strain O44N7J were tested, at least once, in 3-liter fed-batch fermentations to evaluate strain performance and protein expression levels.

The strains were each grown on a PDA plate for 5-9 days at 28° C. Three 500 ml shake flasks each containing 100 ml of shake flask medium for each strain were inoculated with two plugs from their respective PDA plate. The shake flasks were incubated at 26° C. for 48 hours on an orbital shaker at 250 rpm. The cultures were used as seeds for larger scale fermentation.

A total of 160 ml of each seed culture was used to inoculate Applikon Biotechnology 3-liter glass jacketed fermentors containing 1.5 liters of fermentation batch medium. The fermenters were maintained at a temperature of 28° C. and pH was controlled using an Applikon control system to a set-point of 3.85+/−0.25. Air was added to the vessels at a rate of 2.5 L/min and the broths were agitated by Rushton impeller rotating at 1100 rpm. Fermentation feed medium composed of dextrose and phosphoric acid was dosed at a rate of 0 to 18 g/hour for a period of 163 hours based on a dissolved oxygen-controlled ramp. Daily samples of 1 ml were taken from each fermentor, centrifuged, and stored at −20° C.

Example 11: Assays Performed on Fermentation Samples

The samples from Example 10 were submitted for total protein assay and beta-glucosidase assay to evaluate whether the introduced mutations were beneficial to *Trichoderma reesei* performance in a 3-liter fed-batch fermentation.

Total protein assay. Day 7 fermentation samples were desalted and buffer exchanged into 50 mM sodium acetate-100 mM NaCl pH 5.0 using an ECONO-PAC® 10DG Desalting Column (Bio-Rad Laboratories, Inc.). After desalting the protein concentration of the enzyme compositions was determined using a Gallery Analyzer (Thermo Scientific). Cultures were diluted appropriately in water. An albumin standard (bovine serum albumin; BSA) was serial diluted to a concentration range of 0.66 mg/ml to 0.087 mg/ml in water. A total of 20 μl of each dilution including standard was transferred to a cuvette containing 200 μl of a bicinchoninic acid (BCA) substrate solution (Pierce BCA Protein Assay Kit; Thermo Scientific) and then incubated at 37° C. for 30 minutes. Upon completion of the incubation the optical density of 540 nm was measured for each sample. Sample concentrations were determined by extrapolation from the generated standard curve.

Figure 4:
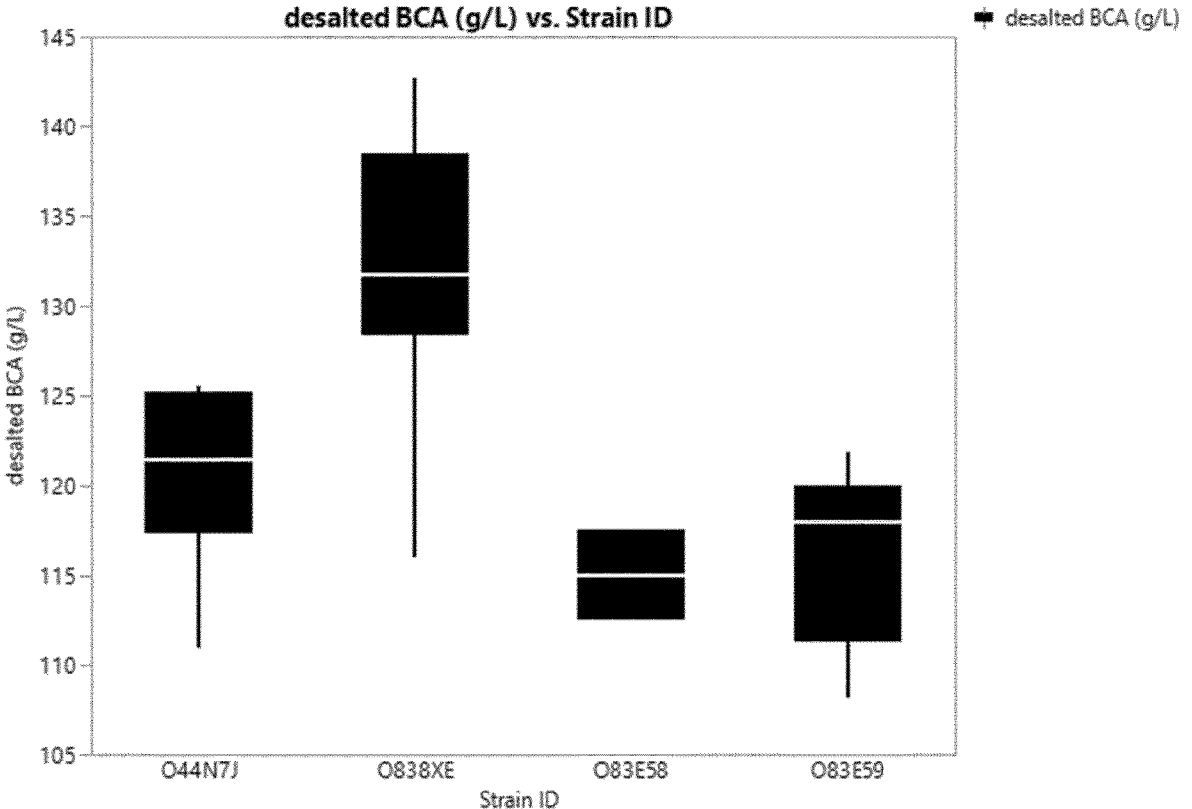
FIG. 4 shows a comparison of *T. reesei* strains O83E59, O83E58, and O838XE and parent *T. reesei* strain O44N7J vs. day 7 total protein values in a "box plot" representation. The black boxes represent the spread of data samples between the first and the third quartiles. The white lines in the middle represent the median value.

FIG. 4 shows a comparison of each strain vs. day 7 total protein values in a "box plot" representation. The black boxes represent the spread of data samples between the first and the third quartiles. The white lines in the middle represent the median values.

Based on the comparison shown in FIG. 4, T. reesei strain O838XE produced significantly higher total protein than the parent T. reesei strain O44N7J, while T. reesei strains O83E58 and O83E59 were not significantly different from the parent strain. The p-value associated with this comparison of T. reesei strain O838XE with the parent T. reesei strain O44N7J was 0.0009. On average the increase in total protein was 9.2%.

Beta-glucosidase assay. Day 2, day 3, day 4, day 5, day 6 and day 7 samples were diluted appropriately in 0.1 M succinate, 0.01% TRITON® X-100 buffer pH 5.0 (sample buffer) followed with a series dilution from 0-fold to ⅓-fold to ⅑-fold of the diluted sample. A standard curve was prepared by diluting a beta-glucosidase standard to a range of 0.2 to 0.01 cellobiase biomass unit (Biomass) CBU(B) per ml. One CBU(B) is the amount of enzyme which releases 2 μmoles of glucose per minute under the conditions defined below with cellobiose as substrate. A total of 20 μl of each dilution was transferred to a 96-well flat bottom plate. Two hundred microliters of a 1 mg/ml para-nitrophe-nyl-beta-D-glucopyranoside substrate in 0.1 M succinate pH 5.0 buffer solution were added to each well and then incubated at ambient temperature for 45 minutes. Upon completion of the incubation period 50 μl of quench solution (1 M TRIS buffer pH 9) were added per well. An endpoint was measured at an optical density of 405 nm for the 96-well plate. Sample activity was determined by extrapolating from the generated standard curve.

Figure 5:
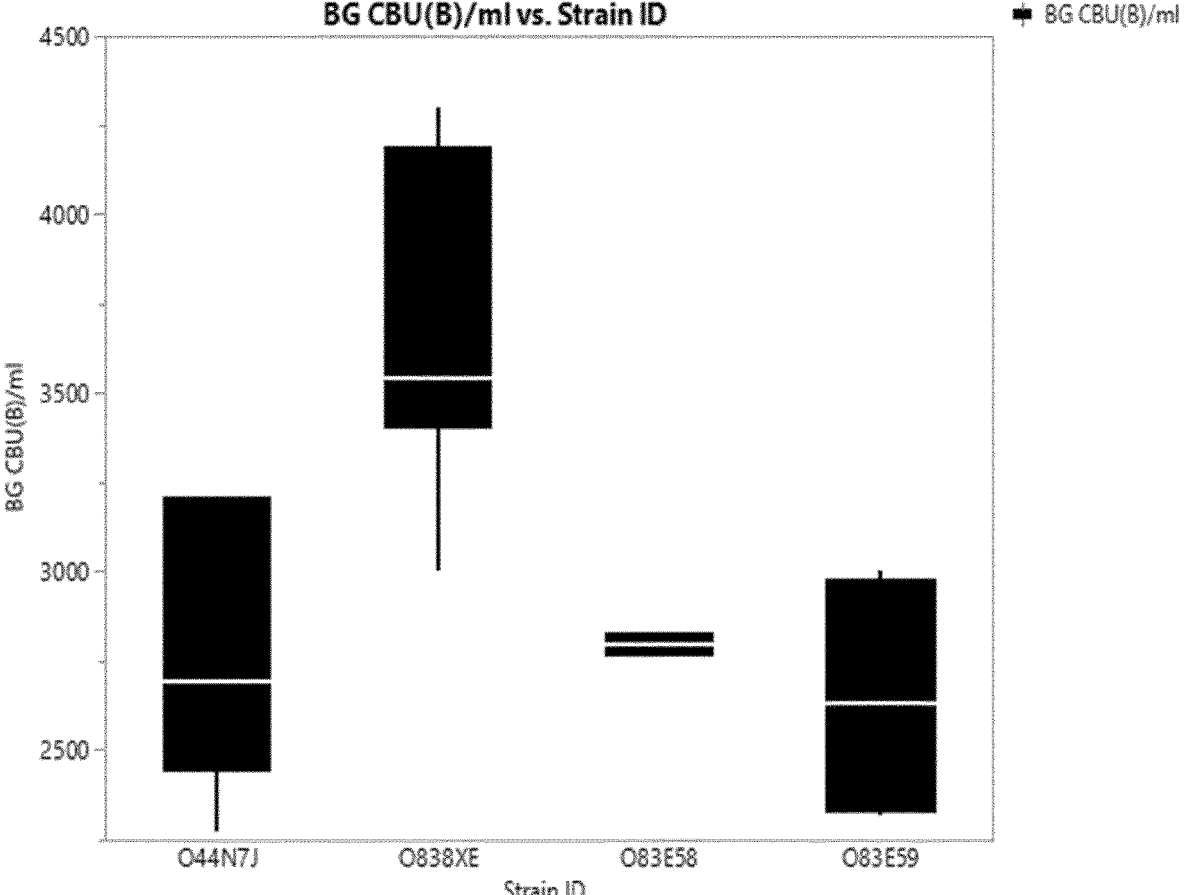
FIG. 5 shows a comparison of *T. reesei* strains O83E59, O83E58, and O838XE and parent *T. reesei* strain O44N7J vs day 7 beta-glucosidase activity values in a "box plot" representation. The black boxes represent the spread of data samples between the first and the third quartiles. The white lines in the middle represent the median values.

FIG. 5 shows a comparison of each strain vs day 7 beta-glucosidase activity values in a "box plot" representation. The black boxes represent the spread of data samples between the first and the third quartiles. The white lines in the middle represent the median values.

Based on the comparison shown in FIG. 5, T. reesei strain O838XE produced significantly higher beta-glucosidase activity than the parent T. reesei strain O44N7J, while T. reesei strain O83E58 and O83E59 were not significantly different from the parent strain. The p-value associated with this comparison of T. reesei strain O838XE with the parent T. reesei strain O44N7J was 0.0187. On average the increase in beta-glucosidase activity was 32.5%.

Figure 6:
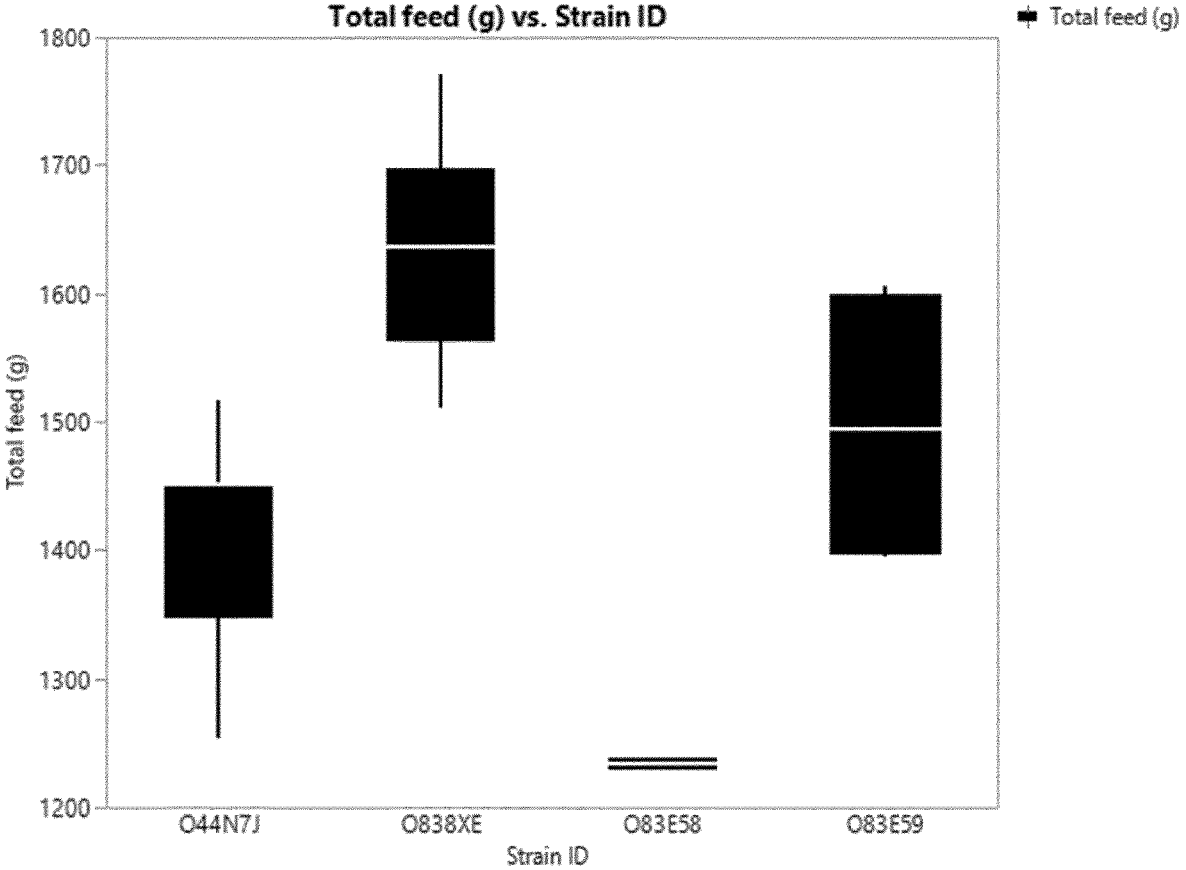
FIG. 6 shows a comparison of *T. reesei* strains O83E59, O83E58, and O838XE and parent *T. reesei* strain O44N7J vs day 7 total feed (total grams of feed used in the fermentation run) in a "box plot" representation. The black boxes represent the spread of data samples between the first and the third quartiles. The white lines in the middle represent the median values.

Decreased viscosity and total feed. FIG. 6 shows a comparison of each strain vs total feed (total grams of feed used in the fermentation run) in a "box plot" representation. The black boxes are day 7 fermentation data. The black boxes represent the spread of data samples between the first and the third quartiles. The white lines in the middle represent the median values.

Based on the comparison shown in FIG. 6, T. reesei strain O838XE used significantly higher total feed than the parent T. reesei strain O44N7J, while T. reesei strains O83E58 and O83E59 were not significantly different from the parent strain. The p-value associated with the comparison of T. reesei strain O838XE with the parent T. reesei strain O44N7J was 0.0005. On average the increase in total feed was 16.1%. Because the fermentations were run using a dissolved oxygen ramp-based feed profile the total feed was actually a proxy for viscosity. When the viscosity goes down the oxygen transfer into the fermentor is better and more feed can be added to the fermentor. When the viscosity goes up the oxygen transfer is worse so total feed would go down. Since the total feed was higher for T. reesei strain O838XE viscosity was lower.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated mutant of a parent *Trichoderma* cell, comprising:

(a) a polynucleotide encoding a polypeptide of interest;

(b) a racA gene encoding a Rho-GTPase RacA protein, wherein the racA gene is modified in the parent *Trichoderma* cell to produce the mutant rendering the mutant partially or completely deficient in the production of the Rho-GTPase RacA protein; and (c) a ras2 gene encoding a GTPase Ras2 protein, wherein the GTPase Ras2 protein is modified in the parent *Trichoderma* cell to produce a GTPase Ras2 variant comprising a substitution at a position corresponding to position 16 of SEQ ID NO: 11;

wherein the combination of the modified racA gene and the Ras2 variant synergistically increases the productivity of the mutant in the production of the polypeptide of interest.

2. The mutant of claim 1, wherein the Rho-GTPase RacA is selected from the group consisting of:

(i) a Rho-GTPase RacA protein comprising an amino acid sequence having at least 70% sequence identity to SEQ ID NO: 2, (ii) a Rho-GTPase RacA protein encoded by a polynucleotide comprising a nucleotide sequence having at least 70% sequence identity to SEQ ID NO: 1, and (iii) a Rho-GTPase RacA protein encoded by a polynucleotide comprising a nucleotide sequence that hybridizes under high stringency conditions with the full-length complement of SEQ ID NO: 1.

3. The mutant of claim 1, wherein the GTPase Ras2 is selected from the group consisting of:

(i) a GTPase Ras2 protein comprising an amino acid sequence having at least 70% sequence identity to SEQ ID NO: 11, (ii) a GTPase Ras2 protein encoded by a polynucleotide comprising a nucleotide sequence having at least 70% sequence identity to SEQ ID NO: 10, and (iii) a GTPase Ras2 protein encoded by a polynucleotide comprising a nucleotide sequence that hybridizes under high stringency conditions with the full-length complement of SEQ ID NO: 10.

4. The mutant of claim 1, wherein the GTPase Ras2 variant comprises a substitution of the amino acid residue at position 16 with valine (Val).

5. The mutant of claim 4, wherein the GTPase Ras2 variant comprises the substitution Gly16Val at position 16 of SEQ ID NO: 11 or corresponding to position 16 of SEQ ID NO: 11.

6. The mutant of claim 1, wherein the GTPase Ras2 variant has at least 85% sequence identity, but less than 100% sequence identity, to the polypeptide of SEQ ID NO: 11.

7. The mutant of claim 1, wherein the polypeptide of interest is native to the parent *Trichoderma* cell or the mutant thereof.

8. The mutant of claim 1, wherein the polypeptide of interest is heterologous to the parent *Trichoderma* cell or the mutant thereof.

9. The mutant of claim 1, wherein the polypeptide of interest is an antibody, an antigen, an antimicrobial peptide, an enzyme, a growth factor, a hormone, an immunodilator, a neurotransmitter, a receptor, a reporter protein, a structural protein, or a transcription factor.

10. The mutant of claim 1, wherein the polypeptide of interest is a cellulase.

11. The mutant of claim 10, wherein the cellulase is an endoglucanase, a cellobiohydrolase, or a beta-glucosidase.

12. The mutant of claim 1, wherein the polypeptide of interest is a hemicellulase.

13. The mutant of claim 12, wherein the hemicellulase is a xylanase, an acetylxylan esterase, a feruloyl esterase, an arabinofuranosidase, a xylosidase, or a glucuronidase.

14. The mutant of claim 1, wherein the parent filamentous fungal cell is a *Trichoderma harzianum, Trichoderma koningii, Trichoderma longibrachiatum, Trichoderma reesei*, or *Trichoderma viride* cell.

15. The mutant of claim 1, wherein the *Trichoderma* cell is a *Trichoderma reesei* cell.

16. The mutant of claim 1, wherein the productivity of the mutant in the production of the amount of the polypeptide of interest is increased compared to the parent *Trichoderma* cell.

17. A method of producing a polypeptide of interest, comprising cultivating the mutant filamentous fungal cell of claim 1 in a medium for production of the polypeptide of interest.

18. The method of claim 17, further comprising recovering the polypeptide of interest from the cultivation medium.

\* \* \* \* \*

SEQUENCE LISTING

```
<160> NUMBER OF SEQ ID NOS: 25

<210> SEQ ID NO 1
<211> LENGTH: 1054
<212> TYPE: DNA
<213> ORGANISM: Trichoderma reesei

<400> SEQUENCE: 1
atggcgcaag ctggagtgca atcgctgaag gtaatatcat tcatctgctc ctctcttcca        60
cttggggggt ttttttttc ttcttcttct cttttcttg ggccacttac tgacgcctcc       120
tgtctccttt agtgtgtcgt gaccggtgac ggtgccgtcg gcaaggtatg tcgcaaccat       180
ttctcccctc cccttcttct agttcttggt cgactaacgc atgattttgc gcagacctgt       240
cttctcatct cgtacacgac caatgctttc cccggagagt acatcccgac cgtgttagtt       300
tcgcctcccg atatgacaca accaactctg gctcgcgaat attgattgtt gactttgggt       360
```

-continued

```
cctcccgcca caggtttgac aactactctg ctagcgtcat tgttgatggc aagccgatca      420
gcctgggtct ttgggacact gcaggccagg aggattatga tagactccgg cccttgtcct      480 accccccagac cgacgtgttc ctcatctgtt tctccgtcgt gagcccgcct tcttacgata     540
acgttgccgc aaaggtatga tatgccgtcc ctccccgttc tgcttctttg ttgagcgaca      600
agagctgtac atctgacgat accccagtgg ctccccgaga tcacccacca ctcgtctgga      660
actcccatca tcctcgtcgg taccaagatc gatcttcgcg atgacccggc tacccgagcc      720
gccctgacca agcaacacat ggagccggtc aagtacgaga acgtgctcaa ctacgtcaag      780
gaggtcaaca agaccaacaa aatcatctac aaatacattg agtgttccgc cctgactcag      840
cgcaacctca agagtgtctt tgacgaggct attcggtaag caaacgcctc cagcccgcgc      900
tgttgcggct ttcagtctcg attgattcct gcctgctctc tgcctgcctc tgcccccctt      960
tgcacagcta acagttctgt ctttgatcag tgcggttctc aaccccaccc ctcaggcttc     1020
caaggccaaa aagtccaagt gctcgatcct gtaa                                  1054
```

<210> SEQ ID NO 2
<211> LENGTH: 204
<212> TYPE: PRT
<213> ORGANISM: Trichoderma reesei

<400> SEQUENCE: 2

```
Met Ala Gln Ala Gly Val Gln Ser Leu Lys Cys Val Val Thr Gly Asp
1               5                   10                  15

Gly Ala Val Gly Lys Thr Cys Leu Leu Ile Ser Tyr Thr Thr Asn Ala
            20                  25                  30

Phe Pro Gly Glu Tyr Ile Pro Thr Val Phe Asp Asn Tyr Ser Ala Ser
        35                  40                  45

Val Ile Val Asp Gly Lys Pro Ile Ser Leu Gly Leu Trp Asp Thr Ala
    50                  55                  60

Gly Gln Glu Asp Tyr Asp Arg Leu Arg Pro Leu Ser Tyr Pro Gln Thr
65                  70                  75                  80

Asp Val Phe Leu Ile Cys Phe Ser Val Val Ser Pro Pro Ser Tyr Asp
                85                  90                  95

Asn Val Ala Ala Lys Trp Leu Pro Glu Ile Thr His His Ser Ser Gly
            100                 105                 110

Thr Pro Ile Ile Leu Val Gly Thr Lys Ile Asp Leu Arg Asp Asp Pro
        115                 120                 125

Ala Thr Arg Ala Ala Leu Thr Lys Gln His Met Glu Pro Val Lys Tyr
    130                 135                 140

Glu Asn Val Leu Asn Tyr Val Lys Glu Val Asn Lys Thr Asn Lys Ile
145                 150                 155                 160

Ile Tyr Lys Tyr Ile Glu Cys Ser Ala Leu Thr Gln Arg Asn Leu Lys
                165                 170                 175

Ser Val Phe Asp Glu Ala Ile Arg Ala Val Leu Asn Pro Thr Pro Gln
            180                 185                 190

Ala Ser Lys Ala Lys Lys Ser Lys Cys Ser Ile Leu
        195                 200
```

<210> SEQ ID NO 3
<211> LENGTH: 16354
<212> TYPE: DNA
<213> ORGANISM: Artificial sequence
<220> FEATURE:
<223> OTHER INFORMATION: Synthesized in laboratory

<400> SEQUENCE: 3

```
gccattcgcc attcaggctg cgcaactgtt gggaagggcg atcggtgcgg gcctcttcgc      60
tattacgcca gctggcgaaa gggggatgtg ctgcaaggcg attaagttgg gtaacgccag     120
ggttttccca gtcacgacgt tgtaaaacga cggccagtga attcgagctc ggtacccggg     180
ctaattatgg ggtgtcgccc ttattcgact ctatagtgaa gttcctattc tctagaaagt     240
ataggaactt ctgaagtggg gatttaaatg cggccgcgct gagggtttaa tcgacgaagc     300
agctgacggc cagtgccaag cttaacgcgt accgggccca gtatatgttc cgcagatgac     360
tggagctctg ccatacgtgc cctctcaagc accatttgtt ccatctacag agactagtca     420
ccaactagtc tatcaagact cacagggtac attgctgaga ccaactgacc agaggcaggg     480
tagcggattg acggctccat ctccttcact tacaaggtct attgaaagcc ctttagcatc     540
accaagcgga gaatagattg ttaagcttat tttttgtata ctgttttgtg atagcacgaa     600
gtttttccac ggtatcttgt aaaaatatat atttgtggcg ggcttaccta catcaaatta     660
ataagagact aattataaac taaacacaca agcaagctac tttagggtaa aagtttataa     720
atgcttttga cgtataaacg ttgcttgtat ttattattac aattaaaggt ggatagaaaa     780
cctagagact agttagaaac taatctcagg tttgcgttaa actaaatcag agcccgagag     840
gttaacagaa cctagaaggg gactagatat ccgggtaggg aaacaaaaaa aaaaaacaag     900
acagccacat attagggaga ctagttagaa gctagttcca ggactaggaa aataaaagac     960
aatgatacca cagtctagtt gacaactaga tagattctag attgaggcca aagtctctga    1020
gatccaggtt agttgcaact aatactagtt agtatctagt ctcctataac tctgaagcta    1080
gaataactta ctactattat cctcaccact gttcagctgc gcaaacggag tgattgcaag    1140
gtgttcagag actagttatt gactagtcag tgactagcaa taactaacaa ggtattaacc    1200
taccatgtct gccatcaccc tgcacttcct cgggctcagc agccttttcc tcctcatttt    1260
catgctcatt ttccttgttt aagactgtga ctagtcaaag actagtccag aaccacaaag    1320
gagaaatgtc ttaccacttt cttcattgct tgtctctttt gcattatcca tgtctgcaac    1380
tagttagagt ctagttagtg actagtccga cgaggacttg cttgtctccg gattgttgga    1440
ggaactctcc agggcctcaa gatccacaac agagccttct agaagactgg tcaataacta    1500
gttggtcttt gtctgagtct gacttacgag gttgcatact cgctcccttt gcctcgtcaa    1560
tcgatgagaa aaagcgccaa aactcgcaat atggctttga accacacggt gctgagacta    1620
gttagaatct agtcccaaac tagcttggat agcttacctt tgccctttgc gttgcgacag    1680
gtcttgcagg gtatggttcc tttctcacca gctgatttag ctgccttgct accctcacgg    1740
cggatctgcc ataaagagtg gctagaggtt ataaattagc actgatccta ggtacggggc    1800
tgaatgtaac ttgcctttcc tttctcatcg cgcggcaaga caggcttgct caaattccta    1860
ccagtcacag gggtatgcac ggcgtacgga ccacttgaac tagtcacaga ttagttagca    1920
actagtctgc attgaatggc tgtacttacg ggccctcgcc attgtcctga tcatttccag    1980
cttcaccctc gttgctgcaa agtagttagt gactagtcaa ggactagttg aaatgggaga    2040
agaaactcac gaattctcga ctcccttagt attgtggtcc ttggacttgg tgctgctata    2100
tattagctaa tacactagtt agactcacag aaacttacgc agctcgcttg cgcttcttgg    2160
taggagtcgg ggttgggaga acagtgcctt caaacaagcc ttcataccat gctacttgac    2220
tagtcaggga ctagtcacca agtaatctag ataggacttg cctttggcct ccatcagttc    2280
cttcatagtg ggaggaccat tgtgcaatgt aaactccatg ccgtgggagt tcttgtcctt    2340
```

```
caagtgcttg accaatatgt ttctgttggc agagggaacc tgtcaactag ttaataacta      2400
gtcagaaact atgatagcag tagactcact gtacgcttga ggcatccctt cactcggcag      2460
tagacttcat atggatggat atcaggcacg ccattgtcgt cctgtggact agtcagtaac      2520
taggcttaaa gctagtcggg tcggcttact atcttgaaat ccggcagcgt aagctccccg      2580
tccttaactg cctcgagata gtgacagtac tctggggact ttcggagatc gttatcgtta      2640
tcgcgaatgc tcggcatact aactgttgac tagtcttgga ctagtcccga gcaaaaagga      2700
ttggaggagg aggaggaagg tgagagtgag acaaagagcg aaataagagc ttcaaaggct      2760
atctctaagc agtatgaagg ttaagtatct agttcttgac tagatttaaa agagatttcg      2820
actagttatg tacctggagt ttggatatag gaatgtgttg tggtaacgaa atgtaagggg      2880
gaggaaagaa aaagtcggtc aagaggtaac tctaagtcgg ccattccttt ttgggaggcg      2940
ctaaccataa acggcatggt cgacttagag ttagctcagg gaatttaggg agttatctgc      3000
gaccaccgag gaacggcgga atgccaaaga atcccgatgg agctctagct ggcggttgac      3060
aaccccacct tttggcgttt ctgcggcgtt gcaggcggga ctggatactt cgtagaacca      3120
gaaaggcaag gcagaacgcg ctcagcaaga gtgttggaag tgatagcatg atgtgccttg      3180
ttaactaggt caaaatctgc agtatgcttg atgttatcca aagtgtgaga gaggaaggtc      3240
caaacataca cgattgggag agggcctagg tataagagtt tttgagtaga acgcatgtga      3300
gcccagccat ctcgaggaga ttaaacacgg gccggcattt gatggctatg ttagtacccc      3360
aatggaaacg gtgagagtcc agtggtcgca gataactccc taaattccct gagctaactc      3420
taagtcgacc atgccgttta tggttagcgc ctcccaaaaa ggaatggccg acttagagtt      3480
acctcttgac cgacttttc tttcctcccc cttacatttc gttaccacaa cacattccta      3540
tatccaaact ccaggtacat aactagtcga aatctctttt aaatctagtc aagaactaga      3600
tacttaacct tcatactgct tagagatagc cttttgaagct cttatttcgc tctttgtctc      3660
actctcacct tcctcctcct cctccaatcc tttttgctcg ggactagtcc aagactagtc      3720
aacagttagt atgccgagca ttcgcgataa cgataacgat ctccgaaagt ccccagagta      3780
ctgtcactat ctcgaggcag ttaaggacgg ggagcttacg ctgccggatt tcaagatagt      3840
aagccgaccc gactagcttt aagcctagtt actgactagt ccacaggacg acaatggcgt      3900
gcctgatatc catccatatg aagtctactg ccgagtgaag ggatgcctca agcgtacagt      3960
gagtctactg ctatcatagt ttctgactag ttattaacta gttgacaggt tccctctgcc      4020
aacagaaaca tattggtcaa gcacttgaag gacaagaact cccacggcat ggagtttaca      4080
ttgcacaatg gtcctcccac tatgaaggaa ctgatggagg ccaaaggcaa gtcctatcta      4140
gattacttgg tgactagtcc ctgactagtc aagtagcatg gtatgaaggc ttgtttgaag      4200
gcactgttct cccaaccccg actcctacca agaagcgcaa gcgagctgcg taagtttctg      4260
tgagtctaac tagtgtatta gctaatatat agcagcacca agtccaagga ccacaatact      4320
aagggagtcg agaattcgtg agtttcttct cccatttcaa ctagtccttg actagtcact      4380
aactactttg cagcaacgag ggtgaagctg gaaatgatca ggacaatggc gagggcccgt      4440
aagtacagcc attcaatgca gactagttgc taactaatct gtgactagtt caagtggtcc      4500
gtacgccgtg cataccctg tgactggtag gaatttgagc aagcctgtct tgccgcgcga      4560
tgagaaagga aaggcaagtt acattcagcc ccgtacctag gatcagtgct aatttataac      4620
ctctagccac tctttatggc agatccgccg tgagggtagc aaggcagcta aatcagctgg      4680
```

-continued

```
tgagaaagga  accatacctc  gcaagacctg  tcgcaacgca  aagggcaaag  gtaagctatc  4740
caagctagtt  tgggactaga  ttctaactag  tctcagcacc  gtgtggttca  aagccatatt  4800 gcgagtttg  gcgctttttc  tcatcgattg  acgaggcaaa  gggagcgagt  atgcaacctc  4860
gtaagtcaga  ctcagacaaa  gaccaactag  ttattgacca  gtcttctaga  aggctctgtt  4920
gtggatcttg  aggccctgga  gagttcctcc  aacaatccgg  agacaagcaa  gtcctcgtcg  4980
gactagtcac  taactagact  ctaactagtt  gcagacatgg  ataatgcaaa  agagacaagc  5040
aatgaagaaa  gtggtaagac  atttctcctt  tgtggttctg  gactagtctt  tgactagtca  5100
cagtcttaaa  caaggaaaat  gagcatgaaa  atgaggagga  aaaggctgct  gagcccgagg  5160
aagtgcaggg  tgatggcaga  catggtaggt  taataccttg  ttagttattg  ctagtcactg  5220
actagtcaat  aactagtctc  tgaacacctt  gcaatcactc  cgtttgcgca  gctgaacagt  5280
ggtgaggata  atagtagtaa  gttattctag  cttcagagtt  ataggagact  agatactaac  5340
tagtattagt  tgcaactaac  ctggatctca  gagactttgg  cctcaatcta  gaatctatct  5400
agttgtcaac  tagactgtgg  tatcattgtc  ttttattttc  ctagtcctgg  aactagcttc  5460
taactagtct  ccctaatatg  tggctgtctt  gttttttttt  tttgtttccc  tacccggata  5520
tctagtcccc  ttctaggttc  tgttaacctc  tcgggctctg  atttagttta  acgcaaacct  5580
gagattagtt  tctaactagt  ctctaggttt  tctatccacc  tttaattgta  ataataaata  5640
caagcaacgt  ttatacgtca  aaagcattta  taaacttta  ccctaaagta  gcttgcttgt  5700
gtgtttagtt  tataattagt  ctcttattaa  tttgatgtag  gtaagcccgc  cacaaatata  5760
tatttttaca  agataccgtg  gaaaaacttc  gtgctatcac  aaaacagtat  acaaaaaata  5820
agcttaacaa  tctattctcc  gcttggtgat  gctaaagggc  tttcaataga  ccttgtaagt  5880
gaaggagatg  gagccgtcaa  tccgctaccc  tgcctctggt  cagttggtct  cagcaatgta  5940
ccctgtgagt  cttgatagac  tagttggtga  ctagtctctg  tagatggaac  aaatggtgct  6000
tgagagggca  cgtatggcag  agctccagtc  atctgcggaa  catatactgg  gcccggggat  6060
cctctagagt  cgacctgcag  gttcatttaa  acggcttcac  gggcagccca  gcggtcgatt  6120
tcgcttccaa  attttggggg  aaagggtccc  tgagcagcct  cacaaacgca  aacatgcgca  6180
cgcgccacac  ggaaaatgaa  gctgactttg  aattttttaag  aatcccctttt  gcccgtggca  6240 ccttctgatt  tttgtcttcg  tgtccaatcc  atctccttga  acgacaaccc  agccctttct  6300
atttcctatc  ccctaatatc  taatgtgagt  cctcatcgtc  acagacggcg  acggacgcga  6360
catttcgccc  gtgctcatcg  accgctctgc  tgtcgccaac  agaacacgcg  gttatgtcgc  6420
gttccgcttt  gtcgtaccac  tttcgcccca  caccgctgac  ctcgcgttcc  cagcatgaaa  6480
aagcctgaac  tcaccgcgac  gtctgtcgag  aagtttctga  tcgaaaagtt  cgacagcgtc  6540
tccgacctga  tgcagctctc  ggagggcgaa  gaatctcgtg  ctttcagctt  cgatgtagga  6600
gggcgtggat  atgtcctgcg  ggtaaatagc  tgcgccgatg  gtttctacaa  agatcgttat  6660
gtttatcggc  actttgcatc  ggccgcgctc  ccgattccgg  aagtgcttga  cattggggag  6720
ttcagcgaga  gcctgaccta  ttgcatctcc  cgccgtgcac  agggtgtcac  gttgcaagac  6780
ctgcctgaaa  ccgaactgcc  cgctgttctg  cagccggtcg  cggaggccat  ggatgcgatc  6840
gctgcggccg  atcttagcca  gacgagcggg  ttcggcccat  tcggaccgca  aggaatcggt  6900
caatacacta  catggcgtga  tttcatatgc  gcgattgctg  atccccatgt  gtatcactgg  6960
caaactgtga  tggacgacac  cgtcagtgcg  tccgtcgcgc  aggctctcga  tgagctgatg  7020
ctttgggccg  aggactgccc  cgaagtccgg  cacctcgtgc  acgcggattt  cggctccaac  7080
```

```
aatgtcctga cggacaatgg ccgcataaca gcggtcattg actggagcga ggcgatgttc   7140 gggggattccc aatacgaggt cgccaacatc ttcttctgga ggccgtggtt ggcttgtatg   7200
gagcagcaga cgcgctactt cgagcggagg catccggagc ttgcaggatc gccgcggctc   7260
cgggcgtata tgctccgcat tggtcttgac caactctatc agagcttggt tgacggcaat   7320
ttcgatgatg cagcttgggc gcagggtcga tgcgacgcaa tcgtccgatc cggagccggg   7380
actgtcgggc gtacacaaat cgcccgcaga agcgcggccg tctggaccga tggctgtgta   7440
gaagtactcg ccgatagtgg aaaccgacgc cccagcactc gtccgagggc aaggaatagt   7500
aaatgattcg ttagttcttt cctgaactga tgattcgcgc gattcgtatt tctctttgtt   7560
ggttgttctg atgatgatga aaatgacgca tctctttatt tgctgcactc gtacacccat   7620
cctttggaat gattaatacc cctccttttt catcgcggac ggtagtcgtt ctctttgggg   7680
ccgtgtttct tcccattcgc atgcgacctc gtggtcattg actgtctgtc ctcttcctct   7740
ccacctacct ccaccaccta cgttgactgc atatcacttt ttcaaacatt catgataata   7800
cgctaccttc tggcatgacc tttttgatgat cgcttttttac tatcctttca attacgatgt   7860
tgtcacttct atttgtcatt ttgcggaatt agtattttct ttccatcttc gatggagaga   7920
tgaatattgc ctgcaggcat gcaagctttc tgctcgaggc catctggctt ttctctgctg   7980
tctgcctcgg gaatgggatg gaataccacg tacggtattt ggcctccggt gccatccgaa   8040
gcgagatgct ttgagcttga aacccctcg gcctgcacag gtgtctcatc gtgcatttaa   8100
tccaacggcg gcgagtcaaa acatcagcta attgaccagg tttctggatt gtgaatgcca   8160
acttttgggg tcttgaggag ttgcggggtg ggaaaaaagt aaagaaattt actgaggatt   8220
ttatcattgc gactataaaa taaagcggca ttgcaaatcc ttgcgttgct actatgtaaa   8280
atggactgta gttgtgctgc tgaaaatagt ttggcgattg tggattgtgg attgtggatt   8340
gtggattatg gcaagttgtc aaggggcaag ttgacgaaaa tgattgtgtg gtgtctgcca   8400
gcaaattgag aacgtgggta tatatttcat cttttcatga ttcccttcgg cttgcttgtc   8460
aagcaatggc atcattggtc tagtggtaga attcgtcgtt gccatcgacg aggcccgtgt   8520
tcgattcacg gatgatgcag gaatttctac tcttgtagat ctttttttgg ctcttgggtt   8580
cgaactgccc aaggcccatg ttttggtcat ctttttttttt atgccccacc atttgggtca   8640
cccctgccaa tcattccatc tttgttccta cccttcacgt gtgctttccg aagccaaagt   8700
tcccattcaa caactctcct tgcgtttttt ttttcttgaa gcttgtcacc cgtcgatagt   8760
ttctgccatt tgcaatcgag acagcagaat caccgcccaa gttaagcctt tgtgctgatc   8820
atgctctcga acgggccaag ttcgggaaaa gcaaaggagc gtttagtgag gggcaatttg   8880
actcacctcc caggcaacag atgagggggg caaaaagaaa gaaattttcg tgagtcaata   8940
tggattccga gcatcatttt cttgcggtct atcttgctac gtatgttgat cttgacgctg   9000
tggatcaagc aacgccactc gctcgctcca tcgcaggctg gtcgcagaca aattaaaagg   9060
cggcaaactc gtacagccgc ggggttgtcc gctgcaaagt acagagtgat aaaagccgcc   9120
atgcgaccat caacgcgttg atgcccagct ttttcgatcc gagaatccac cgtagaggcg   9180
atagcaagta aagaaaagct aaacaaaaaa aaatttctgc ccctaagcca tgaaaacgag   9240
atggggtgga gcagaaccaa ggaaagagtc gcgctgggct gccgttccgg aaggtgttgt   9300
aaaggctcga cgcccaaggt gggagtctag gagaagaatt tgcatcggga gtggggcggg   9360
ttacccctcc atatccaatg acagatatct accagccaag ggtttgagcc cgcccgctta   9420
```

```
gtcatcgtcc tcgcttgccc ctccataaaa ggatttcccc tccccctccc acaaaatttt    9480
ctttcccttc ctctccttgt ccgcttcagt acgtatatct tcccttccct cgcttctctc    9540
ctccatcctt ctttcatcca tctcctgcta acttctctgc tcagcacctc tacgcattac    9600
tagccgtagt atctgagcac ttctcccttt tatattccac aaaacataac acaaccttca    9660
ccatgaacaa cggcacaaac aacttccaga acttcattgg aatctcgtcg ttgcagaaga    9720
ctttgcgcaa cgccctcatc cccacagaaa ctacccagca gttcattgtg aagaacggaa    9780
tcatcaagga agatgaactc cgaggcgaga accgccagat tttgaaggac atcatggatg    9840
attactaccg tggtttcatc tcggaaacgc tctcctccat tgacgacatc gattggactt    9900
cgttgttcga aaagatggaa atccagctca aaaacggcga taacaaggat accttgatca    9960
aggagcagac cgagtatcgg aaggcgatcc ataagaagtt cgccaacgat gatcggttca    10020
agaacatgtt ctcggccaag ttgatttccg acattctccc cgaattcgtg atccataaca    10080
acaactactc ggcgtcggag aaggaggaga agacgcaggt catcaagttg ttctcgaggt    10140
tcgccacatc gttcaaagac tatttttaaga atcgtgcgaa ctgtttctcg gcagatgata    10200
tctcctcgtc ctcctgtcac cgcattgtga acgacaacgc ggaaatcttc ttctcgaacg    10260
cgttggtgta taggcgcatc gtgaagtccc tctccaacga tgacatcaac aaaatctcgg    10320
gagatatgaa ggattcgctc aaggagatgt cgttggagga aatctactcc tatgagaagt    10380
atggcgagtt cattacgcag gagggcattt ccttctacaa cgacatttgt ggtaaagtca    10440
actcgttcat gaacctctac tgtcagaaaa acaaggagaa caaaaacctc tataagctcc    10500
agaagttgca taagcagatc ctctgtatcg cagacacctc gtacgaggtc ccttacaagt    10560
tcgaatccga tgaggaggtc taccagtccg tcaacggatt cttggacaac atctcctcga    10620
aacacattgt cgagcggctc cgaaagatcg gcgataacta caacggctac aacttggaca    10680
aaatctatat cgtctccaag ttctatgagt ccgtctcgca gaaaacctat cgtgattggg    10740
agactatcaa cactgcgctc gagattcact ataacaacat cttgcctggt aacggcaaat    10800
cgaaagccga caaggtgaag aaggccgtga aaaacgatct ccagaagtcg atcacagaaa    10860
tcaacgaact cgtctcgaac tacaagctct gttcggatga taacatcaag gcggaaacgt    10920
acatccatga aatctcgcat atcttgaaca acttcgaggc ccaggaactc aaatacaacc    10980
ccgagatcca cttggtcgag tcggagctca agcctcgga gttgaagaac gtcttggatg    11040
tcatcatgaa cgcattccac tggtgttccg tgttcatgac cgaggaactc gtcgataaag    11100
acaacaactt ctacgcggaa ctcgaggaaa tctacgatga aatctatccc gtgatctccc    11160
tctacaacct cgtgcgaaac tacgtcactc agaagcccta ttccaccaag aagatcaagc    11220
tcaacttcgg catccccact ctcgcagacg gttggtcgaa gtcgaaggag tactccaaca    11280
acgccattat cctcatgcga gacaacctct actacttggg tatcttcaac gcaaagaaca    11340
agccggataa gaagatcatt gaaggcaaca cttcggaaaa caagggagac tataagaaga    11400
tgatctacaa cctcctccct ggacccaaca agatgattcc taaagtgttc ctctcgtcga    11460
agactggtgt ggaaacgtat aagccgtcgg cctacatctt ggagggctac aaacagaaca    11520
agcatatcaa gtcctcgaag gacttcgaca tcactttctg tcacgacctc atcgactatt    11580
tcaagaactg tattgcaatc catccggaat ggaagaactt cggcttcgat ttctcggata    11640
cttcgacata cgaagatatc tcgggattct accgagaggt cgaattgcag ggctataaga    11700
ttgattggac ctacatctcg gaaaaggata tcgacttgct ccaggaaaag ggccagctct    11760
acctcttcca gatttacaac aaggacttct ccaagaagtc gacgggtaac gacaacttgc    11820
```

```
acacaatgta tctcaaaaac ctcttctcgg aggagaactt gaaggatatc gtgctcaaat   11880
tgaacggaga ggccgaaatc ttcttccgta agtcctccat caagaacccg atcatccata   11940
agaagggatc gatcttggtc aaccggactt acgaagcaga ggaaaaagat cagttcggaa   12000
acatccagat tgtcaggaag aacatccctg aaaacatcta tcaggagttg tataagtact   12060
tcaacgacaa gtcggataag gagctctccg acgaagcagc caaactcaag aacgtcgtcg   12120
gacaccatga agcagcaacc aacattgtga aggactaccg gtacacttac gacaagtact   12180
tcttgcacat gccgatcact atcaacttca aagccaacaa gaccggattc attaacgaca   12240
ggatcctcca gtacattgcc aaagaaaagg acctccatgt catcggtatc gataggggag   12300
aacggaacct catctacgtc tccgtgattg acacttgtgg caacattgtc gaacagaagt   12360
cgttcaacat cgtcaacggt tacgattacc agattaagtt gaaacagcag gaaggtgcga   12420
ggcagattgc gcgaaaggaa tggaaggaga ttggcaaaat caaggagatt aaggaaggct   12480
acttgtcgtt ggtcatccac gaaatctcga aaatggtgat caaatacaac gccatcatcg   12540
ccatggaaga cctctcgtac ggcttcaaaa agggacggtt caaagtggag cgtcaggtgt   12600
accagaagtt cgaaacaatg ttgatcaaca agttgaacta cttggtgttc aaggacattt   12660
ccattaccga gaacggagga ttgctcaagg gttatcagct cacgtacatc cccgacaagt   12720
tgaaaaacgt gggacaccag tgtggctgta tcttctacgt gcctgcagcc tacacgtcga   12780
aaatcgaccc tacaacagga ttcgtgaaca tcttcaagtt caaggatctc accgtcgacg   12840
cgaagcggga gttcatcaaa aagttcgact ccatccgcta tgattcggag aagaacttgt   12900
tctgtttcac attcgactac aacaacttca ttactcagaa caccgtgatg tccaaatcgt   12960
cgtggtccgt gtacacgtat ggtgtgcgca tcaaaaggcg cttcgtcaac ggtcgcttct   13020
ccaacgaatc ggacacgatc gatatcacga aagacatgga gaaaacattg gaaatgaccg   13080
acatcaactg cgtgacggc catgacctca ggcaggacat catcgattac gagatcgtcc   13140
agcacatctt cgaaatcttc cgtctcaccg tgcagatgag gaactccctc tccgagctcg   13200
aagatcggga ttacgaccgg ctcatttccc ctgtgttgaa cgagaacaac atcttctacg   13260
actcggcaaa agcgggagat gcattgccga aggacgccga tgcgaacggt gcatattgta   13320
ttgcactcaa gggtctctac gaaatcaagc agatcaccga aaactggaag gaggacggca   13380
aattctcgag ggacaagttg aagatttcga acaaggattg gttcgatttc atccagaaca   13440
agaggtactt gcctccgaag aagaagcgaa aggtgtgagc ggacattcga tttatgccgt   13500
tatgacttcc ttaaaaaagc ctttacgaat gaaagaaatg gaattagact tgttatgtag   13560
ttgattctac aatggattat gattcctgaa cttcaaatcc gctgttcatt attaatctca   13620
gctcttcccg taaagccaat gttgaaacta ttcgtaaatg tacctcgttt tgcgtgtacc   13680
ttgcttatca cgtgatatta catgacctgg acagagttct gcgcgaaagt cataacgtaa   13740
atcccgggcg gtaggtgcgt cccggccgga aggtagtttt ctcgtccacc ccaacgcgtt   13800
tatcaacctc aactttcaac aaccatcatg ccaccaaaag cgcgtaaaac aaagcgagat   13860
ttgattgagc aagagggcag gatggcgtaa tcatggtcat agctgtttcc tgtgtgaaat   13920
tgttatccgc tcacaattcc acacaacata cgagccggaa gcataaagtg taaagcctgg   13980
ggtgcctaat gagtgagcta actcacatta attgcgttgc gctcactgcc cgctttccag   14040
tcgggaaacc tgtcgtgcca gctgcattaa tgaatcggcc aacgcgcggg gagaggcggt   14100
ttgcgtattg ggcgctcttc cgcttcctcg ctcactgact cgctgcgctc ggtcgttcgg   14160
```

```
ctgcggcgag cggtatcagc tcactcaaag gcggtaatac ggttatccac agaatcaggg    14220
gataacgcag gaaagaacat gtgagcaaaa ggccagcaaa aggccaggaa ccgtaaaaag    14280
gccgcgttgc tggcgttttt ccataggctc cgcccccctg acgagcatca caaaaatcga    14340
cgctcaagtc agaggtggcg aaacccgaca ggactataaa gataccaggc gtttccccct    14400
ggaagctccc tcgtgcgctc tcctgttccg accctgccgc ttaccggata cctgtccgcc    14460
tttctccctt cgggaagcgt ggcgctttct catagctcac gctgtaggta tctcagttcg    14520
gtgtaggtcg ttcgctccaa gctgggctgt gtgcacgaac cccccgttca gcccgaccgc    14580
tgcgccttat ccggtaacta tcgtcttgag tccaacccgg taagacacga cttatcgcca    14640
ctggcagcag ccactggtaa caggattagc agagcgaggt atgtaggcgg tgctacagag    14700
ttcttgaagt ggtggcctaa ctacggctac actagaagga cagtatttgg tatctgcgct    14760
ctgctgaagc cagttacctt cggaaaaaga gttggtagct cttgatccgg caaacaaacc    14820
accgctggta gcggtggttt ttttgtttgc aagcagcaga ttacgcgcag aaaaaaagga    14880
tctcaagaag atcctttgat cttttctacg gggtctgacg ctcagtggaa cgaaaactca    14940
cgttaaggga ttttggtcat gagattatca aaaaggatct tcacctagat cctttttaaat    15000 taaaaatgaa gttttaaatc aatctaaagt atatatgagt aaacttggtc tgacagttac    15060
caatgcttaa tcagtgaggc acctatctca gcgatctgtc tatttcgttc atccatagtt    15120
gcctgactcc ccgtcgtgta gataactacg atacgggagg gcttaccatc tggccccagt    15180
gctgcaatga taccgcgaga cccacgctca ccggctccag atttatcagc aataaaccag    15240
ccagccggaa gggccgagcg cagaagtggt cctgcaactt tatccgcctc catccagtct    15300
attaattgtt gccgggaagc tagagtaagt agttcgccag ttaatagttt gcgcaacgtt    15360
gttgccattg ctacaggcat cgtggtgtca cgctcgtcgt ttggtatggc ttcattcagc    15420
tccggttccc aacgatcaag gcgagttaca tgatccccca tgttgtgcaa aaaagcggtt    15480
agctccttcg gtcctccgat cgttgtcaga agtaagttgg ccgcagtgtt atcactcatg    15540
gttatggcag cactgcataa ttctcttact gtcatgccat ccgtaagatg cttttctgtg    15600
actggtgagt actcaaccaa gtcattctga gaatagtgta tgcggcgacc gagttgctct    15660
tgcccggcgt caatacggga taataccgcg ccacatagca gaactttaaa agtgctcatc    15720
attggaaaac gttcttcggg gcgaaaactc tcaaggatct taccgctgtt gagatccagt    15780
tcgatgtaac ccactcgtgc acccaactga tcttcagcat cttttacttt caccagcgtt    15840
tctgggtgag caaaaacagg aaggcaaaat gccgcaaaaa agggaataag ggcgacacgg    15900
aaatgttgaa tactcatact cttcctttttt caatattatt gaagcattta tcagggttat    15960
tgtctcatga gcggatacat atttgaatgt atttagaaaa ataaacaaat aggggttccg    16020
cgcacatttc cccgaaaagt gccacctgac gtctaagaaa ccattattat catgacatta    16080
acctataaaa ataggcgtat cacgaggccc tttcgtctcg cgcgtttcgg tgatgacggt    16140
gaaaacctct gacacatgca gctcccggag acggtcacag cttgtctgta gcggatgcc    16200 gggagcagac aagcccgtca gggcgcgtca gcgggtgttg gcgggtgtcg gggctggctt    16260
aactatgcgg catcagagca gattgtactg agagtgcacc atatgcggtg tgaaataccg    16320
cacagatgcg taaggagaaa ataccgcatc aggc                                16354
```

<210> SEQ ID NO 4
<211> LENGTH: 21
<212> TYPE: DNA
<213> ORGANISM: Artificial sequence -continued

```
<220> FEATURE:
<223> OTHER INFORMATION: Synthesized in laboratory

<400> SEQUENCE: 4
cccggagagt acatcccgac c                                              21

<210> SEQ ID NO 5
<211> LENGTH: 95
<212> TYPE: DNA
<213> ORGANISM: Artificial sequence
<220> FEATURE:
<223> OTHER INFORMATION: Synthesized in laboratory

<400> SEQUENCE: 5
attcacggat gatgcaggaa tttctactct tgtagatccc ggagagtaca tcccgacctt     60
tttttggctc ttgggttcga actgcccaag gccca                                95

<210> SEQ ID NO 6
<211> LENGTH: 20
<212> TYPE: DNA
<213> ORGANISM: Artificial sequence
<220> FEATURE:
<223> OTHER INFORMATION: Synthesized in laboratory

<400> SEQUENCE: 6
cttgcttgtc aagcaatggc                                                20

<210> SEQ ID NO 7
<211> LENGTH: 16374
<212> TYPE: DNA
<213> ORGANISM: Artificial sequence
<220> FEATURE:
<223> OTHER INFORMATION: Synthesized in laboratory

<400> SEQUENCE: 7
gccattcgcc attcaggctg cgcaactgtt gggaagggcg atcggtgcgg gcctcttcgc     60
tattacgcca gctggcgaaa gggggatgtg ctgcaaggcg attaagttgg gtaacgccag    120
ggttttccca gtcacgacgt tgtaaaacga cggccagtga attcgagctc ggtacccggg    180
ctaattatgg ggtgtcgccc ttattcgact ctatagtgaa gttcctattc tctagaaagt    240
ataggaactt ctgaagtggg gatttaaatg cggccgcgct gagggtttaa tcgacgaagc    300
agctgacggc cagtgccaag cttaacgcgt accgggccca gtatatgttc cgcagatgac    360
tggagctctg ccatacgtgc cctctcaagc accatttgtt ccatctacag agactagtca    420
ccaactagtc tatcaagact cacagggtac attgctgaga ccaactgacc agaggcaggg    480
tagcggattg acggctccat ctccttcact tacaaggtct attgaaagcc ctttagcatc    540
accaagcgga gaatagattg ttaagcttat tttttgtata ctgttttgtg atagcacgaa    600
gtttttccac ggtatcttgt aaaaatatat atttgtggcg ggcttaccta catcaaatta    660
ataagagact aattataaac taaacacaca agcaagctac tttagggtaa aagtttataa    720
atgcttttga cgtataaacg ttgcttgtat ttattattac aattaaaggt ggatagaaaa    780
cctagagact agttagaaac taatctcagg tttgcgttaa actaaatcag agcccgagag    840
gttaacagaa cctagaaggg gactagatat ccgggtaggg aaacaaaaaa aaaaaacaag    900
acagccacat attagggaga ctagttagaa gctagttcca ggactaggaa aataaaagac    960
aatgatacca cagtctagtt gacaactaga tagattctag attgaggcca aagtctctga   1020
gatccaggtt agttgcaact aatactagtt agtatctagt ctcctataac tctgaagcta   1080
```

```
gaataactta ctactattat cctcaccact gttcagctgc gcaaacggag tgattgcaag    1140
gtgttcagag actagttatt gactagtcag tgactagcaa taactaacaa ggtattaacc    1200
taccatgtct gccatcaccc tgcacttcct cgggctcagc agccttttcc tcctcatttt    1260
catgctcatt ttccttgttt aagactgtga ctagtcaaag actagtccag aaccacaaag    1320
gagaaatgtc ttaccacttt cttcattgct tgtctctttt gcattatcca tgtctgcaac    1380
tagttagagt ctagttagtg actagtccga cgaggacttg cttgtctccg gattgttgga    1440
ggaactctcc agggcctcaa gatccacaac agagccttct agaagactgg tcaataacta    1500
gttggtcttt gtctgagtct gacttacgag gttgcatact cgctcccttt gcctcgtcaa    1560
tcgatgagaa aaagcgccaa aactcgcaat atggctttga accacacggt gctgagacta    1620
gttagaatct agtcccaaac tagcttggat agcttacctt tgccctttgc gttgcgacag    1680
gtcttgcagg gtatggttcc tttctcacca gctgatttag ctgccttgct accctcacgg    1740
cggatctgcc ataaagagtg gctagaggtt ataaattagc actgatccta ggtacggggc    1800
tgaatgtaac ttgcctttcc tttctcatcg cgcggcaaga caggcttgct caaattccta    1860
ccagtcacag gggtatgcac ggcgtacgga ccacttgaac tagtcacaga ttagttagca    1920
actagtctgc attgaatggc tgtacttacg ggccctcgcc attgtcctga tcatttccag    1980
cttcaccctc gttgctgcaa agtagttagt gactagtcaa ggactagttg aaatgggaga    2040
agaaactcac gaattctcga ctcccttagt attgtggtcc ttggacttgg tgctgctata    2100
tattagctaa tacactagtt agactcacag aaacttacgc agctcgcttg cgcttcttgg    2160
taggagtcgg ggttgggaga acagtgcctt caaacaagcc ttcataccat gctacttgac    2220
tagtcaggga ctagtcacca agtaatctag ataggacttg cctttggcct ccatcagttc    2280
cttcatagtg ggaggaccat tgtgcaatgt aaactccatg ccgtgggagt tcttgtcctt    2340
caagtgcttg accaatatgt ttctgttggc agagggaacc tgtcaactag ttaataacta    2400
gtcagaaact atgatagcag tagactcact gtacgcttga ggcatccctt cactcggcag    2460
tagacttcat atggatggat atcaggcacg ccattgtcgt cctgtggact agtcagtaac    2520
taggcttaaa gctagtcggg tcggcttact atcttgaaat ccggcagcgt aagctccccg    2580
tccttaactg cctcgagata gtgacagtac tctggggact ttcggagatc gttatcgtta    2640
tcgcgaatgc tcggcatact aactgttgac tagtcttgga ctagtcccga gcaaaaagga    2700
ttggaggagg aggaggaagg tgagagtgag acaaagagcg aaataagagc ttcaaaggct    2760
atctctaagc agtatgaagg ttaagtatct agttcttgac tagatttaaa agagatttcg    2820
actagttatg tacctggagt ttggatatag gaatgtgttg tggtaacgaa atgtaagggg    2880
gaggaaagaa aaagtcggtc aagaggtaac tctaagtcgg ccattccttt ttgggaggcg    2940
ctaaccataa acggcatggt cgacttagag ttagctcagg gaatttaggg agttatctgc    3000
gaccaccgag gaacggcgga atgccaaaga atcccgatgg agctctagct ggcggttgac    3060
aaccccacct tttggcgttt ctgcggcgtt gcaggcggga ctggatactt cgtagaacca    3120
gaaaggcaag gcagaacgcg ctcagcaaga gtgttggaag tgatagcatg atgtgccttg    3180
ttaactaggt caaaatctgc agtatgcttg atgttatcca aagtgtgaga gaggaaggtc    3240
caaacataca cgattgggag agggcctagg tataagagtt tttgagtaga acgcatgtga    3300
gcccagccat ctcgaggaga ttaaacacgg gccggcattt gatggctatg ttagtacccc    3360
aatggaaacg gtgagagtcc agtggtcgca gataactccc taaattccct gagctaactc    3420
taagtcgacc atgccgttta tggttagcgc ctcccaaaaa ggaatggccg acttagagtt    3480
```

-continued

```
acctcttgac cgactttttc tttcctcccc cttacatttc gttaccacaa cacattccta    3540
tatccaaact ccaggtacat aactagtcga aatctctttt aaatctagtc aagaactaga    3600
tacttaacct tcatactgct tagagatagc ctttgaagct cttatttcgc tctttgtctc    3660
actctcacct tcctcctcct cctccaatcc tttttgctcg ggactagtcc aagactagtc    3720
aacagttagt atgccgagca ttcgcgataa cgataacgat ctccgaaagt ccccagagta    3780
ctgtcactat ctcgaggcag ttaaggacgg ggagcttacg ctgccggatt tcaagatagt    3840
aagccgaccc gactagcttt aagcctagtt actgactagt ccacaggacg acaatggcgt    3900
gcctgatatc catccatatg aagtctactg ccgagtgaag ggatgcctca agcgtacagt    3960
gagtctactg ctatcatagt ttctgactag ttattaacta gttgacaggt tccctctgcc    4020
aacagaaaca tattggtcaa gcacttgaag gacaagaact cccacggcat ggagtttaca    4080
ttgcacaatg gtcctcccac tatgaaggaa ctgatggagg ccaaaggcaa gtcctatcta    4140
gattacttgg tgactagtcc ctgactagtc aagtagcatg gtatgaaggc ttgtttgaag    4200
gcactgttct cccaaccccg actcctacca agaagcgcaa gcgagctgcg taagtttctg    4260
tgagtctaac tagtgtatta gctaatatat agcagcacca agtccaagga ccacaatact    4320
aagggagtcg agaattcgtg agtttcttct cccatttcaa ctagtccttg actagtcact    4380
aactactttg cagcaacgag ggtgaagctg gaaatgatca ggacaatggc gagggcccgt    4440
aagtacagcc attcaatgca gactagttgc taactaatct gtgactagtt caagtggtcc    4500
gtacgccgtg catacccctg tgactggtag gaatttgagc aagcctgtct tgccgcgcga    4560
tgagaaagga aaggcaagtt acattcagcc ccgtacctag gatcagtgct aatttataac    4620
ctctagccac tctttatggc agatccgccg tgagggtagc aaggcagcta aatcagctgg    4680
tgagaaagga accataccct gcaagacctg tcgcaacgca aagggcaaag gtaagctatc    4740
caagctagtt tgggactaga ttctaactag tctcagcacc gtgtggttca aagccatatt    4800
gcgagttttg gcgctttttc tcatcgattg acgaggcaaa gggagcgagt atgcaacctc    4860
gtaagtcaga ctcagacaaa gaccaactag ttattgacca gtcttctaga aggctctgtt    4920
gtggatcttg aggccctgga gagttcctcc aacaatccgg agacaagcaa gtcctcgtcg    4980
gactagtcac taactagact ctaactagtt gcagacatgg ataatgcaaa agagacaagc    5040
aatgaagaaa gtggtaagac atttctcctt tgtggttctg gactagtctt tgactagtca    5100
cagtcttaaa caaggaaaat gagcatgaaa atgaggagga aaaggctgct gagcccgagg    5160
aagtgcaggg tgatggcaga catggtaggt taataccttg ttagttattg ctagtcactg    5220
actagtcaat aactagtctc tgaacacctt gcaatcactc cgtttgcgca gctgaacagt    5280
ggtgaggata atagtagtaa gttattctag cttcagagtt ataggagact agatactaac    5340
tagtattagt tgcaactaac ctggatctca gagactttgg cctcaatcta gaatctatct    5400
agttgtcaac tagactgtgg tatcattgtc ttttattttc ctagtcctgg aactagcttc    5460
taactagtct ccctaatatg tggctgtctt gttttttttt tttgtttccc tacccggata    5520
tctagtcccc ttctaggttc tgttaacctc tcgggctctg atttagttta acgcaaacct    5580
gagattagtt tctaactagt ctctaggttt tctatccacc tttaattgta ataataaata    5640
caagcaacgt ttatacgtca aaagcattta taaactttta ccctaaagta gcttgcttgt    5700
gtgtttagtt tataattagt ctcttattaa tttgatgtag gtaagcccgc cacaaatata    5760 tattttaca agataccgtg gaaaaacttc gtgctatcac aaaacagtat acaaaaaata    5820
```

```
agcttaacaa tctattctcc gcttggtgat gctaaagggc tttcaataga ccttgtaagt   5880
gaaggagatg gagccgtcaa tccgctaccc tgcctctggt cagttggtct cagcaatgta   5940
ccctgtgagt cttgatagac tagttggtga ctagtctctg tagatggaac aaatggtgct   6000
tgagagggca cgtatggcag agctccagtc atctgcggaa catatactgg gcccggggat   6060
cctctagagt cgacctgcag gttcatttaa acggcttcac gggcagccca gcggtcgatt   6120
tcgcttccaa attttggggg aaagggtccc tgagcagcct cacaaacgca aacatgcgca   6180
cgcgccacac ggaaaatgaa gctgactttg aatttttaag aatccccttt gcccgtggca   6240
ccttctgatt tttgtcttcg tgtccaatcc atctccttga acgacaaccc agccctttct   6300
atttcctatc ccctaatatc taatgtgagt cctcatcgtc acagacggcg acggacgcga   6360
catttcgccc gtgctcatcg accgctctgc tgtcgccaac agaacacgcg gttatgtcgc   6420
gttccgcttt gtcgtaccac tttcgcccca caccgctgac ctcgcgttcc cagcatgaaa   6480
aagcctgaac tcaccgcgac gtctgtcgag aagtttctga tcgaaaagtt cgacagcgtc   6540
tccgacctga tgcagctctc ggaggggcgaa gaatctcgtg ctttcagctt cgatgtagga   6600
gggcgtggat atgtcctgcg ggtaaatagc tgcgccgatg gtttctacaa agatcgttat   6660
gtttatcggc actttgcatc ggccgcgctc ccgattccgg aagtgcttga cattggggag   6720
ttcagcgaga gcctgaccta ttgcatctcc cgccgtgcac agggtgtcac gttgcaagac   6780
ctgcctgaaa ccgaactgcc cgctgttctg cagccggtcg cggaggccat ggatgcgatc   6840
gctgcggccg atcttagcca gacgagcggg ttcggcccat tcggaccgca aggaatcggt   6900
caatacacta catggcgtga tttcatatgc gcgattgctg atccccatgt gtatcactgg   6960
caaactgtga tggacgacac cgtcagtgcg tccgtcgcgc aggctctcga tgagctgatg   7020
ctttgggccg aggactgccc cgaagtccgg cacctcgtgc acgcggattt cggctccaac   7080
aatgtcctga cggacaatgg ccgcataaca gcggtcattg actggagcga ggcgatgttc   7140
ggggattccc aatacgaggt cgccaacatc ttcttctgga ggccgtggtt ggcttgtatg   7200
gagcagcaga cgcgctactt cgagcggagg catccggagc ttgcaggatc gccgcggctc   7260
cgggcgtata tgctccgcat tggtcttgac caactctatc agagcttggt tgacggcaat   7320
ttcgatgatg cagcttgggc gcagggtcga tgcgacgcaa tcgtccgatc cggagccggg   7380
actgtcgggc gtacacaaat cgcccgcaga agcgcggccg tctggaccga tggctgtgta   7440
gaagtactcg ccgatagtgg aaaccgacgc cccagcactc gtccgagggc aaggaatagt   7500
aaatgattcg ttagttcttt cctgaactga tgattcgcgc gattcgtatt tctctttgtt   7560
ggttgttctg atgatgatga aaatgacgca tctctttatt tgctgcactc gtacacccat   7620
cctttggaat gattaatacc cctccttttt catcgcggac ggtagtcgtt ctctttgggg   7680
ccgtgtttct tcccattcgc atgcgacctc gtggtcattg actgtctgtc ctcttcctct   7740
ccacctacct ccaccaccta cgttgactgc atatcacttt ttcaaacatt catgataata   7800
cgctaccttc tggcatgacc ttttgatgat cgcttttttac tatcctttca attacgatgt   7860
tgtcacttct atttgtcatt ttgcggaatt agtattttct ttccatcttc gatggagaga   7920
tgaatattgc ctgcaggcat gcaagctttc tgctcgaggc catctggctt ttctctgctg   7980
tctgcctcgg gaatgggatg gaataccacg tacggtattt ggcctccggt gccatccgaa   8040
gcgagatgct ttgagcttga aacccctcg gcctgcacag gtgtctcatc gtgcatttaa   8100
tccaacggcg gcgagtcaaa acatcagcta attgaccagg tttctggatt gtgaatgcca   8160
acttttgggg tcttgaggag ttgcggggtg ggaaaaaagt aaagaaattt actgaggatt   8220
```

-continued

```
ttatcattgc gactataaaa taaagcggca ttgcaaatcc ttgcgttgct actatgtaaa    8280
atggactgta gttgtgctgc tgaaaatagt ttggcgattg tggattgtgg attgtggatt    8340
gtggattatg gcaagttgtc aaggggcaag ttgacgaaaa tgattgtgtg gtgtctgcca    8400
gcaaattgag aacgtgggta tatatttcat cttttcatga ttcccttcgg cttgcttgtc    8460
aagcaatggc atcattggtc tagtggtaga attcgtcgtt gccatcgacg aggcccgtgt    8520
tcgattcacg gatgatgcag gaatttctac tcttgtagat cccggagagt acatcccgac    8580 cttttttttgg ctcttgggtt cgaactgccc aaggcccatg ttttggtcat ctttttttttt    8640 atgcccacc atttgggtca cccctgccaa tcattccatc tttgttccta cccttcacgt    8700
gtgctttccg aagccaaagt tcccattcaa caactctcct tgcgtttttt ttttcttgaa    8760
gcttgtcacc cgtcgatagt ttctgccatt tgcaatcgag acagcagaat caccgcccaa    8820
gttaagcctt tgtgctgatc atgctctcga acgggccaag ttcgggaaaa gcaaaggagc    8880
gtttagtgag gggcaatttg actcacctcc caggcaacag atgaggggg caaaaagaaa    8940 gaaattttcg tgagtcaata tggattccga gcatcatttt cttgcggtct atcttgctac    9000
gtatgttgat cttgacgctg tggatcaagc aacgccactc gctcgctcca tcgcaggctg    9060
gtcgcagaca aattaaaagg cggcaaactc gtacagccgc ggggttgtcc gctgcaaagt    9120
acagagtgat aaaagccgcc atgcgaccat caacgcgttg atgcccagct ttttcgatcc    9180
gagaatccac cgtagaggcg atagcaagta aagaaaagct aaacaaaaaa aaatttctgc    9240
ccctaagcca tgaaaacgag atggggtgga gcagaaccaa ggaaagagtc gcgctgggct    9300
gccgttccgg aaggtgttgt aaaggctcga cgcccaaggt gggagtctag gagaagaatt    9360
tgcatcggga gtggggcggg ttacccctcc atatccaatg acagatatct accagccaag    9420
ggtttgagcc cgcccgctta gtcatcgtcc tcgcttgccc ctccataaaa ggatttcccc    9480 tcccctccc acaaaatttt cttttccctttc ctctccttgt ccgcttcagt acgtatatct    9540
tcccttccct cgcttctctc ctccatcctt cttttcatcca tctcctgcta acttctctgc    9600
tcagcacctc tacgcattac tagccgtagt atctgagcac ttctcccttt tatattccac    9660
aaaacataac acaaccttca ccatgaacaa cggcacaaac aacttccaga acttcattgg    9720
aatctcgtcg ttgcagaaga ctttgcgcaa cgccctcatc cccacagaaa ctacccagca    9780
gttcattgtg aagaacggaa tcatcaagga agatgaactc cgaggcgaga accgccagat    9840
tttgaaggac atcatggatg attactaccg tggtttcatc tcggaaacgc tctcctccat    9900
tgacgacatc gattggactt cgttgttcga aaagatggaa atccagctca aaaacgcgca    9960
taacaaggat accttgatca aggagcagac cgagtatcgg aaggcgatcc ataagaagtt    10020
cgccaacgat gatcggttca agaacatgtt ctcggccaag ttgatttccg acattctccc    10080
cgaattcgtg atccataaca caactactc ggcgtcggag aaggaggaga agacgcaggt    10140
catcaagttg ttctcgaggt tcgccacatc gttcaaagac tattttaaga atcgtgcgaa    10200
ctgtttctcg gcagatgata tctcctcgtc ctcctgtcac cgcattgtga acgacaacgc    10260
ggaaatcttc ttctcgaacg cgttggtgta taggcgcatc gtgaagtccc tctccaacga    10320
tgacatcaac aaaatctcgg gagatatgaa ggattcgctc aaggagatgt cgttggagga    10380
aatctactcc tatgagaagt atggcgagtt cattacgcag gagggcattt ccttctacaa    10440
cgacatttgt ggtaaagtca actcgttcat gaacctctac tgtcagaaaa acaaggagaa    10500
caaaaacctc tataagctcc agaagttgca taagcagatc ctctgtatcg cagacacctc    10560
```

```
gtacgaggtc ccttacaagt tcgaatccga tgaggaggtc taccagtccg tcaacggatt   10620
cttggacaac atctcctcga aacacattgt cgagcggctc cgaaagatcg gcgataacta   10680
caacggctac aacttggaca aaatctatat cgtctccaag ttctatgagt ccgtctcgca   10740
gaaaacctat cgtgattggg agactatcaa cactgcgctc gagattcact ataacaacat   10800
cttgcctggt aacggcaaat cgaaagccga caaggtgaag aaggccgtga aaaacgatct   10860
ccagaagtcg atcacagaaa tcaacgaact cgtctcgaac tacaagctct gttcggatga   10920
taacatcaag gcggaaacgt acatccatga aatctcgcat atcttgaaca acttcgaggc   10980
ccaggaactc aaatacaacc ccgagatcca cttggtcgag tcggagctca aagcctcgga   11040
gttgaagaac gtcttggatg tcatcatgaa cgcattccac tggtgttccg tgttcatgac   11100
cgaggaactc gtcgataaag acaacaactt ctacgcggaa ctcgaggaaa tctacgatga   11160
aatctatccc gtgatctccc tctacaacct cgtgcgaaac tacgtcactc agaagcccta   11220
ttccaccaag aagatcaagc tcaacttcgg catccccact ctcgcagacg gttggtcgaa   11280
gtcgaaggag tactccaaca acgccattat cctcatgcga gacaacctct actacttggg   11340
tatcttcaac gcaaagaaca agccggataa gaagatcatt gaaggcaaca cttcggaaaa   11400
caagggagac tataagaaga tgatctacaa cctcctccct ggacccaaca agatgattcc   11460
taaagtgttc ctctcgtcga agactggtgt ggaaacgtat aagccgtcgg cctacatctt   11520
ggagggctac aaacagaaca agcatatcaa gtcctcgaag gacttcgaca tcactttctg   11580
tcacgacctc atcgactatt tcaagaactg tattgcaatc catccggaat ggaagaactt   11640
cggcttcgat ttctcggata cttcgacata cgaagatatc tcgggattct accgagaggt   11700
cgaattgcag ggctataaga ttgattggac ctacatctcg gaaaaggata tcgacttgct   11760
ccaggaaaag ggccagctct acctcttcca gatttacaac aaggacttct ccaagaagtc   11820
gacgggtaac gacaacttgc acacaatgta tctcaaaaac ctcttctcgg aggagaactt   11880
gaaggatatc gtgctcaaat tgaacggaga ggccgaaatc ttcttccgta agtcctccat   11940
caagaacccg atcatccata agaagggatc gatcttggtc aaccggactt acgaagcaga   12000
ggaaaaagat cagttcggaa acatccagat tgtcaggaag aacatccctg aaaacatcta   12060
tcaggagttg tataagtact tcaacgacaa gtcggataag gagctctccg acgaagcagc   12120
caaactcaag aacgtcgtcg acaccatga agcagcaacc aacattgtga aggactaccg   12180
gtacacttac gacaagtact tcttgcacat gccgatcact atcaacttca aagccaacaa   12240
gaccggattc attaacgaca ggatcctcca gtacattgcc aaagaaaagg acctccatgt   12300
catcggtatc gataggggag aacggaacct catctacgtc tccgtgattg acacttgtgg   12360
caacattgtc gaacagaagt cgttcaacat cgtcaacggt tacgattacc agattaagtt   12420
gaaacagcag gaaggtgcga ggcagattgc gcgaaaggaa tggaaggaga ttggcaaaat   12480
caaggagatt aaggaaggct acttgtcgtt ggtcatccac gaaatctcga aaatggtgat   12540
caaatacaac gccatcatcg ccatggaaga cctctcgtac ggcttcaaaa agggacggtt   12600
caaagtggag cgtcaggtgt accagaagtt cgaaacaatg ttgatcaaca agttgaacta   12660
cttggtgttc aaggacattt ccattaccga gaacggagga ttgctcaagg gttatcagct   12720
cacgtacatc cccgacaagt tgaaaaacgt gggacaccag tgtggctgta tcttctacgt   12780
gcctgcagcc tacacgtcga aaatcgaccc tacaacagga ttcgtgaaca tcttcaagtt   12840
caaggatctc accgtcgacg cgaagcggga gttcatcaaa aagttcgact ccatccgcta   12900
tgattcggag aagaacttgt tctgtttcac attcgactac aacaacttca ttactcagaa   12960
```

-continued

```
caccgtgatg tccaaatcgt cgtggtccgt gtacacgtat ggtgtgcgca tcaaaaggcg   13020
cttcgtcaac ggtcgcttct ccaacgaatc ggacacgatc gatatcacga aagacatgga   13080
gaaaacattg gaaatgaccg acatcaactg gcgtgacggc catgacctca ggcaggacat   13140
catcgattac gagatcgtcc agcacatctt cgaaatcttc cgtctcaccg tgcagatgag   13200
gaactccctc tccgagctcg aagatcggga ttacgaccgg ctcatttccc ctgtgttgaa   13260
cgagaacaac atcttctacg actcggcaaa agcgggagat gcattgccga aggacgccga   13320
tgcgaacggt gcatattgta ttgcactcaa gggtctctac gaaatcaagc agatcaccga   13380
aaactggaag gaggacggca aattctcgag ggacaagttg aagatttcga acaaggattg   13440
gttcgatttc atccagaaca agaggtactt gcctccgaag aagaagcgaa aggtgtgagc   13500
ggacattcga tttatgccgt tatgacttcc ttaaaaaagc ctttacgaat gaaagaaatg   13560
gaattagact tgttatgtag ttgattctac aatggattat gattcctgaa cttcaaatcc   13620
gctgttcatt attaatctca gctcttcccg taaagccaat gttgaaacta ttcgtaaatg   13680
tacctcgttt tgcgtgtacc ttgcttatca cgtgatatta catgacctgg acagagttct   13740
gcgcgaaagt cataacgtaa atcccgggcg gtaggtgcgt cccgggcgga aggtagtttt   13800
ctcgtccacc ccaacgcgtt tatcaacctc aactttcaac aaccatcatg ccaccaaaag   13860
cgcgtaaaac aaagcgagat ttgattgagc aagaggcag gatggcgtaa tcatggtcat   13920
agctgtttcc tgtgtgaaat tgttatccgc tcacaattcc acacaacata cgagccggaa   13980
gcataaagtg taaagcctgg ggtgcctaat gagtgagcta actcacatta attgcgttgc   14040
gctcactgcc cgctttccag tcgggaaacc tgtcgtgcca gctgcattaa tgaatcggcc   14100
aacgcgcggg gagaggcggt ttgcgtattg ggcgctcttc cgcttcctcg ctcactgact   14160
cgctgcgctc ggtcgttcgg ctgcggcgag cggtatcagc tcactcaaag gcggtaatac   14220
ggttatccac agaatcaggg gataacgcag gaaagaacat gtgagcaaaa ggccagcaaa   14280
aggccaggaa ccgtaaaaag gccgcgttgc tggcgttttt ccataggctc cgcccccctg   14340
acgagcatca caaaaatcga cgctcaagtc agaggtggcg aaacccgaca ggactataaa   14400
gataccaggc gtttccccct ggaagctccc tcgtgcgctc tcctgttccg accctgccgc   14460
ttaccggata cctgtccgcc tttctccctt cgggaagcgt ggcgctttct catagctcac   14520
gctgtaggta tctcagttcg gtgtaggtcg ttcgctccaa gctgggctgt gtgcacgaac   14580 ccccgttca gcccgaccgc tgcgccttat ccggtaacta tcgtcttgag tccaacccgg   14640
taagacacga cttatcgcca ctggcagcag ccactggtaa caggattagc agagcgaggt   14700
atgtaggcgg tgctacagag ttcttgaagt ggtggcctaa ctacggctac actagaagga   14760 cagtatttg tatctgcgct ctgctgaagc cagttacctt cggaaaaaga gttggtagct   14820
cttgatccgg caaacaaacc accgctggta gcggtggttt ttttgtttgc aagcagcaga   14880
ttacgcgcag aaaaaaagga tctcaagaag atcctttgat cttttctacg gggtctgacg   14940
ctcagtggaa cgaaaactca cgttaaggga ttttggtcat gagattatca aaaaggatct   15000
tcacctagat cctttttaaat taaaaatgaa gttttaaatc aatctaaagt atatatgagt   15060
aaacttggtc tgacagttac caatgcttaa tcagtgaggc acctatctca gcgatctgtc   15120
tatttcgttc atccatagtt gcctgactcc ccgtcgtgta gataactacg atacgggagg   15180
gcttaccatc tggccccagt gctgcaatga taccgcgaga cccacgctca ccggctccag   15240
atttatcagc aataaaccag ccagccggaa gggccgagcg cagaagtggt cctgcaactt   15300
```

```
tatccgcctc catccagtct attaattgtt gccgggaagc tagagtaagt agttcgccag    15360
ttaatagttt gcgcaacgtt gttgccattg ctacaggcat cgtggtgtca cgctcgtcgt    15420
ttggtatggc ttcattcagc tccggttccc aacgatcaag gcgagttaca tgatcccca    15480 tgttgtgcaa aaaagcggtt agctccttcg gtcctccgat cgttgtcaga agtaagttgg    15540
ccgcagtgtt atcactcatg gttatggcag cactgcataa ttctcttact gtcatgccat    15600
ccgtaagatg cttttctgtg actggtgagt actcaaccaa gtcattctga gaatagtgta    15660
tgcggcgacc gagttgctct tgcccggcgt caatacggga taataccgcg ccacatagca    15720
gaactttaaa agtgctcatc attggaaaac gttcttcggg gcgaaaactc tcaaggatct    15780
taccgctgtt gagatccagt tcgatgtaac ccactcgtgc acccaactga tcttcagcat    15840 ctttacttt caccagcgtt tctgggtgag caaaaacagg aaggcaaaat gccgcaaaaa    15900
agggaataag ggcgacacgg aaatgttgaa tactcatact cttcctttt caatattatt    15960 gaagcattta tcagggttat tgtctcatga gcggatacat atttgaatgt atttagaaaa    16020
ataaacaaat aggggttccg cgcacatttc cccgaaaagt gccacctgac gtctaagaaa    16080
ccattattat catgacatta acctataaaa ataggcgtat cacgaggccc tttcgtctcg    16140
cgcgtttcgg tgatgacggt gaaaacctct gacacatgca gctcccggag acggtcacag    16200
cttgtctgta agcggatgcc gggagcagac aagcccgtca gggcgcgtca gcgggtgttg    16260
gcgggtgtcg gggctggctt aactatgcgg catcagagca gattgtactg agagtgcacc    16320
atatgcggtg tgaaataccg cacagatgcg taaggagaaa ataccgcatc aggc          16374

<210> SEQ ID NO 8
<211> LENGTH: 95
<212> TYPE: DNA
<213> ORGANISM: Artificial sequence
<220> FEATURE:
<223> OTHER INFORMATION: Synthesized in laboratory

<400> SEQUENCE: 8
ttttgcgcag acctgtcttc tcatctcgta cacgaccaat taatgatgtt agtttcgcct       60
cccgatatga cacaaccaac tctggctcgc gaata                                   95

<210> SEQ ID NO 9
<211> LENGTH: 95
<212> TYPE: DNA
<213> ORGANISM: Artificial sequence
<220> FEATURE:
<223> OTHER INFORMATION: Synthesized in laboratory

<400> SEQUENCE: 9
tattcgcgag ccagagttgg ttgtgtcata tcgggaggcg aaactaacat cattaattgg       60
tcgtgtacga gatgagaaga caggtctgcg caaaa                                   95

<210> SEQ ID NO 10
<211> LENGTH: 994
<212> TYPE: DNA
<213> ORGANISM: Trichoderma reesei

<400> SEQUENCE: 10
atggcgggca gaatggtgct gtacaagctg gtggtgctgg agacggtgg tgtcggtaag        60 acggccctga ccatccagct gtgcctgcag cacttcgtcg agacggtaag cattcgctcc      120
ctttggatca gaaccggcat ttttgggggga ggacaacaaa gagatcaacg aagaagacaa     180
gaaacaagca gaaaggggac ggagaaccgc gggagacgaa aacagggagg agaaatcacc     240
```

```
gactcttctt cccctctcct gaccgacttg ggcggacagc ctcggcggcg gtagcgcatg      300
aggggcaggg caacatggag ctcccgtccg cccagcgctg ggcgatgcat tggacgaatg      360
aatagctaac atccgacgtc tacagtacga cccgacaatt gaggactcat accgcaagca      420
ggtcgtcatc gacggccagc cctgcatgct cgaggtcctc gacacggccg ccaggagga      480 gtacacagcg ctgcgagacc aatggatccg agacggtgag ggcttcgtcc tcgtctacag      540
catcgcatcc cgctcgtcct tcacccgcat taagcgcttc caccaccaga tccagcgcgt      600
caaggagtcg gtagcctcct cgccctcata tccgggctca cctctgtccg ccgccagccc      660
gcagctgccc gtgcccatca tgctggtcgg caacaagagc gacagggtca ccgagcgcga      720
ggtatcgacc caggaggggc acgccctcgc tcgcgagctt ggctgcgagt tgtcgaggc      780 ctcggccaag aactgcatca atgttgaaaa ggccttctac gacgtcgtca ggatcctgcg      840
ccggcagcgc cagcaggctt cgcgaccccc tgcgggcgcc agcggccgag cccgaaccag      900
caacggcgac gcgggcggag gaagccgaga cacgcaccgg taccggcgcg gcaaggacgg      960
cgagaagggc aagtccaagt gcattgtctt atga                                  994
```

<210> SEQ ID NO 11
<211> LENGTH: 219
<212> TYPE: PRT
<213> ORGANISM: Trichoderma reesei

<400> SEQUENCE: 11

```
Met Ala Gly Arg Met Val Leu Tyr Lys Leu Val Val Leu Gly Asp Gly
1               5                   10                  15

Gly Val Gly Lys Thr Ala Leu Thr Ile Gln Leu Cys Leu Gln His Phe
            20                  25                  30

Val Glu Thr Tyr Asp Pro Thr Ile Glu Asp Ser Tyr Arg Lys Gln Val
        35                  40                  45

Val Ile Asp Gly Gln Pro Cys Met Leu Glu Val Leu Asp Thr Ala Gly
    50                  55                  60

Gln Glu Glu Tyr Thr Ala Leu Arg Asp Gln Trp Ile Arg Asp Gly Glu
65                  70                  75                  80

Gly Phe Val Leu Val Tyr Ser Ile Ala Ser Arg Ser Phe Thr Arg
                85                  90                  95

Ile Lys Arg Phe His His Gln Ile Gln Arg Val Lys Glu Ser Leu Pro
            100                 105                 110

Val Pro Ile Met Leu Val Gly Asn Lys Ser Asp Arg Val Thr Glu Arg
        115                 120                 125

Glu Val Ser Thr Gln Glu Gly His Ala Leu Ala Arg Glu Leu Gly Cys
    130                 135                 140

Glu Phe Val Glu Ala Ser Ala Lys Asn Cys Ile Asn Val Glu Lys Ala
145                 150                 155                 160

Phe Tyr Asp Val Val Arg Ile Leu Arg Arg Gln Arg Gln Gln Ala Ser
                165                 170                 175

Arg Pro Pro Ala Gly Ala Ser Gly Arg Ala Arg Thr Ser Asn Gly Asp
            180                 185                 190

Ala Gly Gly Gly Ser Arg Asp Thr His Arg Tyr Arg Arg Gly Lys Asp
            195                 200                 205

Gly Glu Lys Gly Lys Ser Lys Cys Ile Val Leu
    210                 215
```

<210> SEQ ID NO 12

```
<211> LENGTH: 21
<212> TYPE: DNA
<213> ORGANISM: Artificial sequence
<220> FEATURE:
<223> OTHER INFORMATION: Synthesized in laboratory

<400> SEQUENCE: 12
cgcccatcat ggcgggcaga a                                                      21

<210> SEQ ID NO 13
<211> LENGTH: 95
<212> TYPE: DNA
<213> ORGANISM: Artificial sequence
<220> FEATURE:
<223> OTHER INFORMATION: Synthesized in laboratory

<400> SEQUENCE: 13
attcacggat gatgcaggaa tttctactct tgtagatcgc ccatcatggc gggcagaatt          60
tttttggctc ttgggttcga actgcccaag gccca                                     95

<210> SEQ ID NO 14
<211> LENGTH: 19
<212> TYPE: DNA
<213> ORGANISM: Artificial sequence
<220> FEATURE:
<223> OTHER INFORMATION: Synthesized in laboratory

<400> SEQUENCE: 14
cttcttgtca agcaatggc                                                        19

<210> SEQ ID NO 15
<211> LENGTH: 16374
<212> TYPE: DNA
<213> ORGANISM: Artificial sequence
<220> FEATURE:
<223> OTHER INFORMATION: Synthesized in laboratory

<400> SEQUENCE: 15
gccattcgcc attcaggctg cgcaactgtt gggaagggcg atcggtgcgg gcctcttcgc          60
tattacgcca gctggcgaaa gggggatgtg ctgcaaggcg attaagttgg gtaacgccag          120
ggttttccca gtcacgacgt tgtaaaacga cggccagtga attcgagctc ggtacccggg          180
ctaattatgg ggtgtcgccc ttattcgact ctatagtgaa gttcctattc tctagaaagt          240
ataggaactt ctgaagtggg gatttaaatg cggccgcgct gagggtttaa tcgacgaagc          300
agctgacggc cagtgccaag cttaacgcgt accgggccca gtatatgttc cgcagatgac          360
tggagctctg ccatacgtgc cctctcaagc accatttgtt ccatctacag agactagtca          420
ccaactagtc tatcaagact cacagggtac attgctgaga ccaactgacc agaggcaggg          480
tagcggattg acggctccat ctccttcact tacaaggtct attgaaagcc ctttagcatc          540
accaagcgga gaatagattg ttaagcttat tttttgtata ctgttttgtg atagcacgaa          600
gtttttccac ggtatcttgt aaaaatatat atttgtggcg gcttaccta catcaaatta          660 ataagagact aattataaac taaacacaca agcaagctac tttagggtaa aagtttataa         720
atgcttttga cgtataaacg ttgcttgtat ttattattac aattaaaggt ggatagaaaa         780
cctagagact agttagaaac taatctcagg tttgcgttaa actaaatcag agcccgagag         840
gttaacagaa cctagaaggg gactagatat ccgggtaggg aaacaaaaaa aaaaaacaag         900
acagccacat attagggaga ctagttagaa gctagttcca ggactaggaa aataaaagac        960
aatgatacca cagtctagtt gacaactaga tagattctag attgaggcca aagtctctga       1020
```

```
gatccaggtt agttgcaact aatactagtt agtatctagt ctcctataac tctgaagcta      1080
gaataactta ctactattat cctcaccact gttcagctgc gcaaacggag tgattgcaag      1140
gtgttcagag actagttatt gactagtcag tgactagcaa taactaacaa ggtattaacc      1200
taccatgtct gccatcaccc tgcacttcct cgggctcagc agccttttcc tcctcatttt      1260
catgctcatt ttccttgttt aagactgtga ctagtcaaag actagtccag aaccacaaag      1320
gagaaatgtc ttaccacttt cttcattgct tgtctctttt gcattatcca tgtctgcaac      1380
tagttagagt ctagttagtg actagtccga cgaggacttg cttgtctccg gattgttgga      1440
ggaactctcc agggcctcaa gatccacaac agagccttct agaagactgg tcaataacta      1500
gttggtcttt gtctgagtct gacttacgag gttgcatact cgctcccttt gcctcgtcaa      1560
tcgatgagaa aaagcgccaa aactcgcaat atggctttga accacacggt gctgagacta      1620
gttagaatct agtcccaaac tagcttggat agcttacctt tgccctttgc gttgcgacag      1680
gtcttgcagg gtatggttcc tttctcacca gctgatttag ctgccttgct accctcacgg      1740
cggatctgcc ataaagagtg gctagaggtt ataaattagc actgatccta ggtacggggc      1800
tgaatgtaac ttgcctttcc tttctcatcg cgcggcaaga caggcttgct caaattccta      1860
ccagtcacag gggtatgcac ggcgtacgga ccacttgaac tagtcacaga ttagttagca      1920
actagtctgc attgaatggc tgtacttacg ggccctcgcc attgtcctga tcatttccag      1980
cttcaccctc gttgctgcaa agtagttagt gactagtcaa ggactagttg aaatgggaga      2040
agaaactcac gaattctcga ctcccttagt attgtggtcc ttggacttgg tgctgctata      2100
tattagctaa tacactagtt agactcacag aaacttacgc agctcgcttg cgcttcttgg      2160
taggagtcgg ggttgggaga acagtgcctt caaacaagcc ttcataccat gctacttgac      2220
tagtcaggga ctagtcacca agtaatctag ataggacttg cctttggcct ccatcagttc      2280
cttcatagtg ggaggaccat tgtgcaatgt aaactccatg ccgtgggagt tcttgtcctt      2340
caagtgcttg accaatatgt ttctgttggc agagggaacc tgtcaactag ttaataacta      2400
gtcagaaact atgatagcag tagactcact gtacgcttga ggcatccctt cactcggcag      2460
tagacttcat atggatggat atcaggcacg ccattgtcgt cctgtggact agtcagtaac      2520
taggcttaaa gctagtcggg tcggcttact atcttgaaat ccggcagcgt aagctccccg      2580
tccttaactg cctcgagata gtgacagtac tctgggggact ttcggagatc gttatcgtta     2640
tcgcgaatgc tcggcatact aactgttgac tagtcttgga ctagtcccga gcaaaaagga      2700
ttggaggagg aggaggaagg tgagagtgag acaaagagcg aaataagagc ttcaaaggct      2760
atctctaagc agtatgaagg ttaagtatct agttcttgac tagatttaaa agagatttcg      2820
actagttatg tacctggagt ttggatatag gaatgtgttg tggtaacgaa atgtaagggg      2880
gaggaaagaa aaagtcggtc aagaggtaac tctaagtcgg ccattccttt ttgggaggcg      2940
ctaaccataa acggcatggt cgacttagag ttagctcagg gaatttaggg agttatctgc      3000
gaccaccgag gaacggcgga atgccaaaga atcccgatgg agctctagct ggcggttgac      3060
aaccccacct tttggcgttt ctgcggcgtt gcaggcggga ctggatactt cgtagaacca      3120
gaaaggcaag gcagaacgcg ctcagcaaga gtgttggaag tgatagcatg atgtgccttg      3180
ttaactaggt caaaatctgc agtatgcttg atgttatcca aagtgtgaga gaggaaggtc      3240
caaacataca cgattgggag agggcctagg tataagagtt tttgagtaga acgcatgtga      3300
gcccagccat ctcgaggaga ttaaacacgg gccggcattt gatggctatg ttagtacccc      3360
```

```
aatggaaacg gtgagagtcc agtggtcgca gataactccc taaattccct gagctaactc    3420
taagtcgacc atgccgttta tggttagcgc ctcccaaaaa ggaatggccg acttagagtt    3480
acctcttgac cgactttttc tttcctcccc cttacatttc gttaccacaa cacattccta    3540
tatccaaact ccaggtacat aactagtcga aatctctttt aaatctagtc aagaactaga    3600
tacttaacct tcatactgct tagagatagc cttttgaagct cttatttcgc tctttgtctc    3660
actctcacct tcctcctcct cctccaatcc tttttgctcg ggactagtcc aagactagtc    3720
aacagttagt atgccgagca ttcgcgataa cgataacgat ctccgaaagt ccccagagta    3780
ctgtcactat ctcgaggcag ttaaggacgg ggagcttacg ctgccggatt tcaagatagt    3840
aagccgaccc gactagcttt aagcctagtt actgactagt ccacaggacg acaatggcgt    3900
gcctgatatc catccatatg aagtctactg ccgagtgaag ggatgcctca agcgtacagt    3960
gagtctactg ctatcatagt ttctgactag ttattaacta gttgacaggt tccctctgcc    4020
aacagaaaca tattggtcaa gcacttgaag gacaagaact cccacggcat ggagtttaca    4080
ttgcacaatg gtcctcccac tatgaaggaa ctgatggagg ccaaaggcaa gtcctatcta    4140
gattacttgg tgactagtcc ctgactagtc aagtagcatg gtatgaaggc ttgtttgaag    4200
gcactgttct cccaaccccg actcctacca agaagcgcaa gcgagctgcg taagtttctg    4260
tgagtctaac tagtgtatta gctaatatat agcagcacca agtccaagga ccacaatact    4320
aagggagtcg agaattcgtg agtttcttct cccatttcaa ctagtccttg actagtcact    4380
aactactttg cagcaacgag ggtgaagctg gaaatgatca ggacaatggc gagggcccgt    4440
aagtacagcc attcaatgca gactagttgc taactaatct gtgactagtt caagtggtcc    4500
gtacgccgtg catacccctg tgactggtag gaatttgagc aagcctgtct tgccgcgcga    4560
tgagaaagga aaggcaagtt acattcagcc ccgtacctag gatcagtgct aatttataac    4620
ctctagccac tctttatggc agatccgccg tgagggtagc aaggcagcta aatcagctgg    4680
tgagaaagga accatacccct gcaagacctg tcgcaacgca aagggcaaag gtaagctatc    4740
caagctagtt tgggactaga ttctaactag tctcagcacc gtgtggttca aagccatatt    4800
gcgagttttg gcgctttttc tcatcgattg acgaggcaaa gggagcgagt atgcaacctc    4860
gtaagtcaga ctcagacaaa gaccaactag ttattgacca gtcttctaga aggctctgtt    4920
gtggatcttg aggccctgga gagttcctcc aacaatccgg agacaagcaa gtcctcgtcg    4980
gactagtcac taactagact ctaactagtt gcagacatgg ataatgcaaa agagacaagc    5040
aatgaagaaa gtggtaagac atttctcctt tgtggttctg gactagtctt tgactagtca    5100
cagtcttaaa caaggaaaat gagcatgaaa atgaggagga aaaggctgct gagcccgagg    5160
aagtgcaggg tgatggcaga catggtaggt taataccttg ttagttattg ctagtcactg    5220
actagtcaat aactagtctc tgaacacctt gcaatcactc cgtttgcgca gctgaacagt    5280
ggtgaggata atagtagtaa gttattctag cttcagagtt ataggagact agatactaac    5340
tagtattagt tgcaactaac ctggatctca gagactttgg cctcaatcta gaatctatct    5400
agttgtcaac tagactgtgg tatcattgtc ttttatttc ctagtcctgg aactagcttc    5460
taactagtct ccctaaatatg tggctgtctt gttttttttt tttgtttccc tacccggata    5520
tctagtcccc ttctaggttc tgttaacctc tcgggctctg atttagttta acgcaaacct    5580
gagattagtt tctaactagt ctctaggttt tctatccacc tttaattgta ataataaata    5640
caagcaacgt ttatacgtca aaagcattta taaacttta ccctaaagta gcttgcttgt    5700
gtgtttagtt tataattagt ctcttattaa tttgatgtag gtaagcccgc cacaaatata    5760
```

-continued

```
tatttttaca agataccgtg gaaaaacttc gtgctatcac aaaacagtat acaaaaaata   5820
agcttaacaa tctattctcc gcttggtgat gctaaagggc tttcaataga ccttgtaagt   5880
gaaggagatg gagccgtcaa tccgctaccc tgcctctggt cagttggtct cagcaatgta   5940
ccctgtgagt cttgatagac tagttggtga ctagtctctg tagatggaac aaatggtgct   6000
tgagagggca cgtatggcag agctccagtc atctgcggaa catatactgg gcccggggat   6060
cctctagagt cgacctgcag gttcatttaa acggcttcac gggcagccca gcggtcgatt   6120
tcgcttccaa attttggggg aaagggtccc tgagcagcct cacaaacgca aacatgcgca   6180
cgcgccacac ggaaaatgaa gctgactttg aattttttaag aatccccttt gcccgtggca   6240
ccttctgatt tttgtcttcg tgtccaatcc atctccttga acgacaaccc agccctttct   6300
atttcctatc ccctaatatc taatgtgagt cctcatcgtc acagacggcg acggacgcga   6360
catttcgccc gtgctcatcg accgctctgc tgtcgccaac agaacacgcg gttatgtcgc   6420
gttccgcttt gtcgtaccac tttcgcccca caccgctgac ctcgcgttcc cagcatgaaa   6480
aagcctgaac tcaccgcgac gtctgtcgag aagtttctga tcgaaaagtt cgacagcgtc   6540
tccgacctga tgcagctctc ggagggcgaa gaatctcgtg ctttcagctt cgatgtagga   6600
gggcgtggat atgtcctgcg ggtaaatagc tgcgccgatg gtttctacaa agatcgttat   6660
gtttatcggc actttgcatc ggccgcgctc ccgattccgg aagtgcttga cattggggag   6720
ttcagcgaga gcctgaccta ttgcatctcc cgccgtgcac agggtgtcac gttgcaagac   6780
ctgcctgaaa ccgaactgcc cgctgttctg cagccggtcg cggaggccat ggatgcgatc   6840
gctgcggccg atcttagcca cacgagcggg ttcggcccat tcggaccgca aggaatcggt   6900
caatacacta catggcgtga tttcatatgc gcgattgctg atccccatgt gtatcactgg   6960
caaactgtga tggacgacac cgtcagtgcg tccgtcgcgc aggctctcga tgagctgatg   7020
ctttgggccg aggactgccc cgaagtccgg cacctcgtgc acgcggattt cggctccaac   7080
aatgtcctga cggacaatgg ccgcataaca gcggtcattg actggagcga ggcgatgttc   7140 gggattccc aatacgaggt cgccaacatc ttcttctgga ggccgtggtt ggcttgtatg   7200
gagcagcaga cgcgctactt cgagcggagg catccggagc ttgcaggatc gccgcggctc   7260
cgggcgtata tgctccgcat tggtcttgac caactctatc agagcttggt tgacggcaat   7320
ttcgatgatg cagcttgggc gcagggtcga tgcgacgcaa tcgtccgatc cggagccggg   7380
actgtcgggc gtacacaaat cgcccgcaga agcgcggccg tctggaccga tggctgtgta   7440
gaagtactcg ccgatagtgg aaaccgacgc cccagcactc gtccgagggc aaggaatagt   7500
aaatgattcg ttagttcttt cctgaactga tgattcgcgc gattcgtatt tctctttgtt   7560
ggttgttctg atgatgatga aaatgacgca tctctttatt tgctgcactc gtacacccat   7620
cctttggaat gattaatacc cctccttttt catcgcggac ggtagtcgtt ctctttgggg   7680
ccgtgtttct tcccattcgc atgcgacctc gtggtcattg actgtctgtc ctcttcctct   7740
ccacctacct ccaccaccta cgttgactgc atatcacttt ttcaaacatt catgataata   7800
cgctaccttc tggcatgacc ttttgatgat cgctttttac tatcctttca attacgatgt   7860
tgtcacttct atttgtcatt ttgcggaatt agtattttct ttccatcttc gatggagaga   7920
tgaatattgc ctgcaggcat gcaagctttc tgctcgaggc catctggctt ttctctgctg   7980
tctgcctcgg gaatgggatg gaataccacg tacggtattt ggcctccggt gccatccgaa   8040
gcgagatgct ttgagcttga aaccccctcg gcctgcacag gtgtctcatc gtgcatttaa   8100
```

```
tccaacggcg gcgagtcaaa acatcagcta attgaccagg tttctggatt gtgaatgcca    8160 acttttttggg tcttgaggag ttgcggggtg ggaaaaaagt aaagaaattt actgaggatt    8220
ttatcattgc gactataaaa taaagcggca ttgcaaatcc ttgcgttgct actatgtaaa    8280
atggactgta gttgtgctgc tgaaaatagt ttggcgattg tggattgtgg attgtggatt    8340
gtggattatg gcaagttgtc aaggggcaag ttgacgaaaa tgattgtgtg gtgtctgcca    8400
gcaaattgag aacgtgggta tatatttcat cttttcatga ttcccttcgg cttgcttgtc    8460
aagcaatggc atcattggtc tagtggtaga attcgtcgtt gccatcgacg aggcccgtgt    8520
tcgattcacg gatgatgcag gaatttctac tcttgtagat cgcccatcat ggcgggcaga    8580
atttttttgg ctcttgggtt cgaactgccc aaggcccatg ttttggtcat cttttttttt    8640
atgccccacc atttgggtca cccctgccaa tcattccatc tttgttccta cccttcacgt    8700
gtgctttccg aagccaaagt tcccattcaa caactctcct tgcgtttttt ttttcttgaa    8760
gcttgtcacc cgtcgatagt ttctgccatt tgcaatcgag acagcagaat caccgcccaa    8820
gttaagcctt tgtgctgatc atgctctcga acgggccaag ttcgggaaaa gcaaaggagc    8880
gtttagtgag gggcaatttg actcacctcc caggcaacag atgagggggg caaaaagaaa    8940
gaaattttcg tgagtcaata tggattccga gcatcatttt cttgcggtct atcttgctac    9000
gtatgttgat cttgacgctg tggatcaagc aacgccactc gctcgctcca tcgcaggctg    9060
gtcgcagaca aattaaaagg cggcaaactc gtacagccgc ggggttgtcc gctgcaaagt    9120
acagagtgat aaaagccgcc atgcgaccat caacgcgttg atgcccagct ttttcgatcc    9180
gagaatccac cgtagaggcg atagcaagta aagaaaagct aaacaaaaaa aaatttctgc    9240
ccctaagcca tgaaaacgag atggggtgga gcagaaccaa ggaaagagtc gcgctgggct    9300
gccgttccgg aaggtgttgt aaaggctcga cgcccaaggt gggagtctag gagaagaatt    9360
tgcatcggga gtggggcggg ttacccctcc atatccaatg acagatatct accagccaag    9420
ggtttgagcc cgcccgctta gtcatcgtcc tcgcttgccc ctccataaaa ggatttcccc    9480 tcccctccc acaaaatttt ctttcccttc ctctccttgt ccgcttcagt acgtatatct    9540
tcccttccct cgcttctctc ctccatcctt ctttcatcca tctcctgcta acttctctgc    9600
tcagcacctc tacgcattac tagccgtagt atctgagcac ttctcccttt tatattccac    9660
aaaacataac acaaccttca ccatgaacaa cggcacaaac aacttccaga acttcattgg    9720
aatctcgtcg ttgcagaaga ctttgcgcaa cgccctcatc cccacagaaa ctacccagca    9780
gttcattgtg aagaacggaa tcatcaagga agatgaactc cgaggcgaga accgccagat    9840
tttgaaggac atcatggatg attactaccg tggtttcatc tcggaaacgc tctcctccat    9900
tgacgacatc gattggactt cgttgttcga aaagatggaa atccagctca aaaacgcgca    9960
taacaaggat accttgatca aggagcagac cgagtatcgg aaggcgatcc ataagaagtt   10020
cgccaacgat gatcggttca agaacatgtt ctcggccaag ttgatttccg acattctccc   10080
cgaattcgtg atccataaca acaactactc ggcgtcggaa aaggaggaga agacgcaggt   10140
catcaagttg ttctcgaggt tcgccacatc gttcaaagac tattttaaga atcgtgcgaa   10200
ctgtttctcg gcagatgata tctcctcgtc ctcctgtcac cgcattgtga acgacaacgc   10260
ggaaatcttc ttctcgaacg cgttggtgta taggcgcatc gtgaagtccc tctccaacga   10320
tgacatcaac aaaatctcgg gagatatgaa ggattcgctc aaggagatgt cgttggagga   10380
aatctactcc tatgagaagt atggcgagtt cattacgcag gagggcatttt ccttctacaa   10440 cgacatttgt ggtaaagtca actcgttcat gaacctctac tgtcagaaaa acaaggagaa   10500
```

-continued

```
caaaaacctc tataagctcc agaagttgca taagcagatc ctctgtatcg cagacacctc    10560
gtacgaggtc ccttacaagt tcgaatccga tgaggaggtc taccagtccg tcaacggatt    10620
cttggacaac atctcctcga aacacattgt cgagcggctc cgaaagatcg gcgataacta    10680
caacggctac aacttggaca aaatctatat cgtctccaag ttctatgagt ccgtctcgca    10740
gaaaacctat cgtgattggg agactatcaa cactgcgctc gagattcact ataacaacat    10800
cttgcctggt aacggcaaat cgaaagccga caaggtgaag aaggccgtga aaaacgatct    10860
ccagaagtcg atcacagaaa tcaacgaact cgtctcgaac tacaagctct gttcggatga    10920
taacatcaag gcggaaacgt acatccatga aatctcgcat atcttgaaca acttcgaggc    10980
ccaggaactc aaatacaacc ccgagatcca cttggtcgag tcggagctca aagcctcgga    11040
gttgaagaac gtcttggatg tcatcatgaa cgcattccac tggtgttccg tgttcatgac    11100
cgaggaactc gtcgataaag acaacaactt ctacgcggaa ctcgaggaaa tctacgatga    11160
aatctatccc gtgatctccc tctacaacct cgtgcgaaac tacgtcactc agaagcccta    11220
ttccaccaag aagatcaagc tcaacttcgg catccccact ctcgcagacg gttggtcgaa    11280
gtcgaaggag tactccaaca acgccattat cctcatgcga gacaacctct actacttggg    11340
tatcttcaac gcaaagaaca agccggataa gaagatcatt gaaggcaaca cttcggaaaa    11400
caagggagac tataagaaga tgatctacaa cctcctccct ggacccaaca agatgattcc    11460
taaagtgttc ctctcgtcga agactggtgt ggaaacgtat aagccgtcgg cctacatctt    11520
ggagggctac aaacagaaca agcatatcaa gtcctcgaag gacttcgaca tcactttctg    11580
tcacgacctc atcgactatt tcaagaactg tattgcaatc catccggaat ggaagaactt    11640
cggcttcgat ttctcggata cttcgacata cgaagatatc tcgggattct accgagaggt    11700
cgaattgcag ggctataaga ttgattggac ctacatctcg gaaaaggata tcgacttgct    11760
ccaggaaaag ggccagctct acctcttcca gatttacaac aaggacttct ccaagaagtc    11820
gacgggtaac gacaacttgc acacaatgta tctcaaaaac ctcttctcgg aggagaactt    11880
gaaggatatc gtgctcaaat tgaacggaga ggccgaaatc ttcttccgta agtcctccat    11940
caagaacccg atcatccata agaagggatc gatcttggtc aaccggactt acgaagcaga    12000
ggaaaaagat cagttcggaa acatccagat tgtcaggaag aacatccctg aaaacatcta    12060
tcaggagttg tataagtact tcaacgacaa gtcggataag gagctctccg acgaagcagc    12120
caaactcaag aacgtcgtcg acaccatga agcagcaacc aacattgtga aggactaccg    12180
gtacacttac gacaagtact tcttgcacat gccgatcact atcaacttca aagccaacaa    12240
gaccggattc attaacgaca ggatcctcca gtacattgcc aaagaaaagg acctccatgt    12300
catcggtatc gataggggag aacggaacct catctacgtc tccgtgattg acacttgtgg    12360
caacattgtc gaacagaagt cgttcaacat cgtcaacggt tacgattacc agattaagtt    12420
gaaacagcag gaaggtgcga ggcagattgc gcgaaaggaa tggaaggaga ttggcaaaat    12480
caaggagatt aaggaaggct acttgtcgtt ggtcatccac gaaatctcga aaatggtgat    12540
caaatacaac gccatcatcg ccatggaaga cctctcgtac ggcttcaaaa agggacggtt    12600
caaagtggag cgtcaggtgt accagaagtt cgaaacaatg ttgatcaaca agttgaacta    12660
cttggtgttc aaggacattt ccattaccga gaacggagga ttgctcaagg gttatcagct    12720
cacgtacatc cccgacaagt tgaaaaacgt gggacaccag tgtggctgta tcttctacgt    12780
gcctgcagcc tacacgtcga aaatcgaccc tacaacagga ttcgtgaaca tcttcaagtt    12840
```

-continued

```
caaggatctc accgtcgacg cgaagcggga gttcatcaaa aagttcgact ccatccgcta    12900
tgattcggag aagaacttgt tctgtttcac attcgactac aacaacttca ttactcagaa    12960
caccgtgatg tccaaatcgt cgtggtccgt gtacacgtat ggtgtgcgca tcaaaaggcg    13020
cttcgtcaac ggtcgcttct ccaacgaatc ggacacgatc gatatcacga aagacatgga    13080
gaaaacattg gaaatgaccg acatcaactg gcgtgacggc catgacctca ggcaggacat    13140
catcgattac gagatcgtcc agcacatctt cgaaatcttc cgtctcaccg tgcagatgag    13200
gaactccctc tccgagctcg aagatcggga ttacgaccgg ctcatttccc ctgtgttgaa    13260
cgagaacaac atcttctacg actcggcaaa agcgggagat gcattgccga aggacgccga    13320
tgcgaacggt gcatattgta ttgcactcaa gggtctctac gaaatcaagc agatcaccga    13380
aaactggaag gaggacggca aattctcgag ggacaagttg aagatttcga acaaggattg    13440
gttcgatttc atccagaaca agaggtactt gcctccgaag aagaagcgaa aggtgtgagc    13500
ggacattcga tttatgccgt tatgacttcc ttaaaaaagc ctttacgaat gaaagaaatg    13560
gaattagact tgttatgtag ttgattctac aatggattat gattcctgaa cttcaaatcc    13620
gctgttcatt attaatctca gctcttcccg taaagccaat gttgaaacta ttcgtaaatg    13680
tacctcgttt tgcgtgtacc ttgcttatca cgtgatatta catgacctgg acagagttct    13740
gcgcgaaagt cataacgtaa atcccgggcg gtaggtgcgt cccgggcgga aggtagtttt    13800
ctcgtccacc ccaacgcgtt tatcaacctc aactttcaac aaccatcatg ccaccaaaag    13860
cgcgtaaaac aaagcgagat ttgattgagc aagagggcag gatggcgtaa tcatggtcat    13920
agctgtttcc tgtgtgaaat tgttatccgc tcacaattcc acacaacata cgagccggaa    13980
gcataaagtg taaagcctgg ggtgcctaat gagtgagcta actcacatta attgcgttgc    14040
gctcactgcc cgctttccag tcgggaaacc tgtcgtgcca gctgcattaa tgaatcggcc    14100
aacgcgcggg gagaggcggt ttgcgtattg ggcgctcttc cgcttcctcg ctcactgact    14160
cgctgcgctc ggtcgttcgg ctgcggcgag cggtatcagc tcactcaaag gcggtaatac    14220
ggttatccac agaatcaggg gataacgcag gaaagaacat gtgagcaaaa ggccagcaaa    14280
aggccaggaa ccgtaaaaag gccgcgttgc tggcgttttt ccataggctc cgcccccctg    14340
acgagcatca caaaaatcga cgctcaagtc agaggtggcg aaacccgaca ggactataaa    14400
gataccaggc gtttccccct ggaagctccc tcgtgcgctc tcctgttccg accctgccgc    14460
ttaccggata cctgtccgcc tttctccctt cgggaagcgt ggcgctttct catagctcac    14520
gctgtaggta tctcagttcg gtgtaggtcg ttcgctccaa gctgggctgt gtgcacgaac    14580
cccccgttca gcccgaccgc tgcgccttat ccggtaacta tcgtcttgag tccaacccgg    14640
taagacacga cttatcgcca ctggcagcag ccactggtaa caggattagc agagcgaggt    14700
atgtaggcgg tgctacagag ttcttgaagt ggtggcctaa ctacggctac actagaagga    14760
cagtatttgg tatctgcgct ctgctgaagc cagttacctt cggaaaaaga gttggtagct    14820
cttgatccgg caaacaaacc accgctggta gcggtggttt ttttgtttgc aagcagcaga    14880
ttacgcgcag aaaaaaagga tctcaagaag atcctttgat cttttctacg gggtctgacg    14940
ctcagtggaa cgaaaactca cgttaaggga ttttggtcat gagattatca aaaaggatct    15000
tcacctagat ccttttaaat taaaaatgaa gttttaaatc aatctaaagt atatatgagt    15060
aaacttggtc tgacagttac caatgcttaa tcagtgaggc acctatctca gcgatctgtc    15120
tatttcgttc atccatagtt gcctgactcc ccgtcgtgta gataactacg atacgggagg    15180
gcttaccatc tggccccagt gctgcaatga taccgcgaga cccacgctca ccggctccag    15240
```

-continued

```
atttatcagc aataaaccag ccagccggaa gggccgagcg cagaagtggt cctgcaactt   15300
tatccgcctc catccagtct attaattgtt gccgggaagc tagagtaagt agttcgccag   15360
ttaatagttt gcgcaacgtt gttgccattg ctacaggcat cgtggtgtca cgctcgtcgt   15420
ttggtatggc ttcattcagc tccggttccc aacgatcaag gcgagttaca tgatccccca   15480
tgttgtgcaa aaaagcggtt agctccttcg gtcctccgat cgttgtcaga agtaagttgg   15540
ccgcagtgtt atcactcatg gttatggcag cactgcataa ttctcttact gtcatgccat   15600
ccgtaagatg cttttctgtg actggtgagt actcaaccaa gtcattctga gaatagtgta   15660
tgcggcgacc gagttgctct tgcccggcgt caatacggga taataccgcg ccacatagca   15720
gaactttaaa agtgctcatc attggaaaac gttcttcggg gcgaaaactc tcaaggatct   15780
taccgctgtt gagatccagt tcgatgtaac ccactcgtgc acccaactga tcttcagcat   15840
cttttacttt caccagcgtt tctgggtgag caaaaacagg aaggcaaaat gccgcaaaaa   15900
agggaataag ggcgacacgg aaatgttgaa tactcatact cttccttttt caatattatt   15960
gaagcattta tcagggttat tgtctcatga gcggatacat atttgaatgt atttagaaaa   16020
ataaacaaat aggggttccg cgcacatttc cccgaaaagt gccacctgac gtctaagaaa   16080
ccattattat catgacatta acctataaaa ataggcgtat cacgaggccc tttcgtctcg   16140
cgcgtttcgg tgatgacggt gaaaacctct gacacatgca gctcccggag acggtcacag   16200
cttgtctgta agcggatgcc gggagcagac aagcccgtca gggcgcgtca gcgggtgttg   16260
gcgggtgtcg gggctggctt aactatgcgg catcagagca gattgtactg agagtgcacc   16320
atatgcggtg tgaaataccg cacagatgcg taaggagaaa ataccgcatc aggc          16374
```

```
<210> SEQ ID NO 16
<211> LENGTH: 140
<212> TYPE: DNA
<213> ORGANISM: Artificial sequence
<220> FEATURE:
<223> OTHER INFORMATION: Synthesized in laboratory

<400> SEQUENCE: 16
ggtcgctcct caaccgctga ctctttgcgc ccatcatggc aggaaggatg gtgctgtaca      60
agctggtggt gctgggagac gttggtgtcg gtaagacggc cctgaccatc cagctgtgcc     120
tgcagcactt cgtcgagacg                                                 140
```

```
<210> SEQ ID NO 17
<211> LENGTH: 140
<212> TYPE: DNA
<213> ORGANISM: Artificial sequence
<220> FEATURE:
<223> OTHER INFORMATION: Synthesized in laboratory

<400> SEQUENCE: 17
cgtctcgacg aagtgctgca ggcacagctg gatggtcagg gccgtcttac cgacaccaac      60
gtctcccagc accaccagct tgtacagcac catccttcct gccatgatgg gcgcaaagag     120
tcagcggttg aggagcgacc                                                 140
```

```
<210> SEQ ID NO 18
<211> LENGTH: 994
<212> TYPE: DNA
<213> ORGANISM: Trichoderma reesei

<400> SEQUENCE: 18
```

```
atggcaggaa ggatggtgct gtacaagctg gtggtgctgg gagacgttgg tgtcggtaag      60
acggccctga ccatccagct gtgcctgcag cacttcgtcg agacggtaag cattcgctcc     120
ctttggatca gaaccggcat ttttggggga ggacaacaaa gagatcaacg aagaagacaa     180
gaaacaagca gaaaggggac ggagaaccgc gggagacgaa aacagggagg agaaatcacc     240
gactcttctt cccctctcct gaccgacttg ggcggacagc ctcggcggcg gtagcgcatg     300
aggggcaggg caacatggag ctcccgtccg cccagcgctg ggcgatgcat tggacgaatg     360
aatagctaac atccgacgtc tacagtacga cccgacaatt gaggactcat accgcaagca     420
ggtcgtcatc gacggccagc cctgcatgct cgaggtcctc gacacggccg gccaggagga     480
gtacacagcg ctgcgagacc aatggatccg agacggtgag ggcttcgtcc tcgtctacag     540
catcgcatcc cgctcgtcct tcacccgcat taagcgcttc caccaccaga tccagcgcgt     600
caaggagtcg gtagcctcct cgccctcata tccgggctca cctctgtccg ccgccagccc     660
gcagctgccc gtgcccatca tgctggtcgg caacaagagc gacagggtca ccgagcgcga     720
ggtatcgacc caggaggggc acgccctcgc tcgcgagctt ggctgcgagt ttgtcgaggc     780
ctcggccaag aactgcatca atgttgaaaa ggccttctac gacgtcgtca ggatcctgcg     840
ccggcagcgc cagcaggctt cgcgaccccc tgcgggcgcc agcggccgag cccgaaccag     900
caacggcgac gcgggcggag gaagccgaga cacgcaccgg taccggcgcg gcaaggacgg     960
cgagaagggc aagtccaagt gcattgtctt atga                                 994
```

<210> SEQ ID NO 19
<211> LENGTH: 219
<212> TYPE: PRT
<213> ORGANISM: Trichoderma reesei

<400> SEQUENCE: 19

```
Met Ala Gly Arg Met Val Leu Tyr Lys Leu Val Val Leu Gly Asp Val
1               5                   10                  15

Gly Val Gly Lys Thr Ala Leu Thr Ile Gln Leu Cys Leu Gln His Phe
            20                  25                  30

Val Glu Thr Tyr Asp Pro Thr Ile Glu Asp Ser Tyr Arg Lys Gln Val
        35                  40                  45

Val Ile Asp Gly Gln Pro Cys Met Leu Glu Val Leu Asp Thr Ala Gly
    50                  55                  60

Gln Glu Glu Tyr Thr Ala Leu Arg Asp Gln Trp Ile Arg Asp Gly Glu
65                  70                  75                  80

Gly Phe Val Leu Val Tyr Ser Ile Ala Ser Arg Ser Ser Phe Thr Arg
                85                  90                  95

Ile Lys Arg Phe His His Gln Ile Gln Arg Val Lys Glu Ser Leu Pro
            100                 105                 110

Val Pro Ile Met Leu Val Gly Asn Lys Ser Asp Arg Val Thr Glu Arg
        115                 120                 125

Glu Val Ser Thr Gln Glu Gly His Ala Leu Ala Arg Glu Leu Gly Cys
    130                 135                 140

Glu Phe Val Glu Ala Ser Ala Lys Asn Cys Ile Asn Val Glu Lys Ala
145                 150                 155                 160

Phe Tyr Asp Val Val Arg Ile Leu Arg Arg Gln Arg Gln Gln Ala Ser
                165                 170                 175

Arg Pro Pro Ala Gly Ala Ser Gly Arg Ala Arg Thr Ser Asn Gly Asp
            180                 185                 190

Ala Gly Gly Gly Ser Arg Asp Thr His Arg Tyr Arg Arg Gly Lys Asp
```

-continued

```
        195                 200                 205

Gly Glu Lys Gly Lys Ser Lys Cys Ile Val Leu
    210                 215

<210> SEQ ID NO 20
<211> LENGTH: 20
<212> TYPE: DNA
<213> ORGANISM: Artificial sequence
<220> FEATURE:
<223> OTHER INFORMATION: Synthesized in laboratory

<400> SEQUENCE: 20
atggcgcaag ctggagtgca                                                20

<210> SEQ ID NO 21
<211> LENGTH: 20
<212> TYPE: DNA
<213> ORGANISM: Artificial sequence
<220> FEATURE:
<223> OTHER INFORMATION: Synthesized in laboratory

<400> SEQUENCE: 21
cgaatagcct cgtcaaagac                                                20

<210> SEQ ID NO 22
<211> LENGTH: 20
<212> TYPE: DNA
<213> ORGANISM: Artificial sequence
<220> FEATURE:
<223> OTHER INFORMATION: Synthesized in laboratory

<400> SEQUENCE: 22
cagcttcccg tcgccgccca                                                20

<210> SEQ ID NO 23
<211> LENGTH: 21
<212> TYPE: DNA
<213> ORGANISM: Artificial sequence
<220> FEATURE:
<223> OTHER INFORMATION: Synthesized in laboratory

<400> SEQUENCE: 23
ctgcttgcgg tatgagtcct c                                              21

<210> SEQ ID NO 24
<211> LENGTH: 20
<212> TYPE: DNA
<213> ORGANISM: Artificial sequence
<220> FEATURE:
<223> OTHER INFORMATION: Synthesized in laboratory

<400> SEQUENCE: 24
gacctccttg acgtagttga                                                20

<210> SEQ ID NO 25
<211> LENGTH: 20
<212> TYPE: DNA
<213> ORGANISM: Artificial sequence
<220> FEATURE:
<223> OTHER INFORMATION: Synthesized in laboratory

<400> SEQUENCE: 25
gcttctgctt ctgcttctgc                                                20
```